United States Patent [19]

Minamida et al.

[11] Patent Number: 6,124,297
[45] Date of Patent: Sep. 26, 2000

[54] α-UNSATURATED AMINES, THEIR PRODUCTION AND USE

[75] Inventors: Isao Minamida, Hyogo; Koichi Iwanaga; Tetsuo Okauchi, both of Osaka, all of Japan

[73] Assignee: Takeda Chemical Industries, Ltd., Osaka, Japan

[21] Appl. No.: 09/227,538

[22] Filed: Jan. 11, 1999

Related U.S. Application Data

[62] Division of application No. 08/957,749, Oct. 24, 1997, Pat. No. 5,935,981, which is a division of application No. 07/225,367, Jul. 28, 1988, Pat. No. 5,849,768.

[30] Foreign Application Priority Data

| Aug. 1, 1987 | [JP] | Japan | 62-192793 |
| Oct. 13, 1987 | [JP] | Japan | 62-258856 |
| Jan. 26, 1988 | [JP] | Japan | 63-16259 |
| Mar. 17, 1988 | [JP] | Japan | 63-64885 |

[51] Int. Cl.[7] .................................................. A61K 31/495
[52] U.S. Cl. ......................... 514/255; 514/247; 514/256; 544/398; 544/402
[58] Field of Search ..................... 544/398, 402; 514/255

[56] References Cited

U.S. PATENT DOCUMENTS 4,567,188  1/1986  Niemers et al. ........................ 514/332
4,918,086  4/1990  Gsell ....................................... 514/255

FOREIGN PATENT DOCUMENTS 0002930  7/1979  European Pat. Off. ............... 546/330

OTHER PUBLICATIONS

Chemical Abstracts, vol. 94, No. 2, col. 2, Abstract No. 64642j, p. 637, Mar. 2, 1981.

*Primary Examiner*—Zinna Northington Davis
*Attorney, Agent, or Firm*—Foley & Lardner

[57] ABSTRACT

α-Unsaturated amines of the formula:

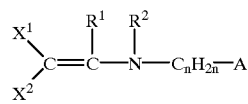

wherein $X^1$ and $X^2$ are such that one is an electron-attracting group with the other being a hydrogen atom or an electron-attracting group; $R^1$ is a group attached through a nitrogen atom; $R^2$ is a hydrogen atom or a group attached through a carbon, nitrogen or oxygen atom; n is an integer equal to 0, 1 or 2; A is a heterocyclic group or a cyclic hydrocarbon group, and salts thereof and their agrochemical use as insecticidal and/or miticidal agents are described.

5 Claims, No Drawings

α-UNSATURATED AMINES, THEIR PRODUCTION AND USE

This application is a divisional of application Ser. No. 08/957,749, filed Oct. 24, 1997 now U.S. Pat. No. 5,935,981 now which is in turn a divisional of application Ser. No. 07/225,367, filed Jul. 28, 1988 now U.S. Pat. No. 5,849,768.

This invention relates to agrochemically useful α-unsaturated amines having insecticidal/miticidal activity, their production and use.

Among α-unsaturated amines, such compounds as (i) cimetidine (described for example in Journal of Medicinal Chemistry 24, 913, 1981), (ii) ranitidine (described for example in Agents Actions 11, 160, 1981) and (iii) famotidine (described for example in Journal of Medicinal Chemistry 27, 849, 1984) are known as histamine $H_2$ receptor antagonists.

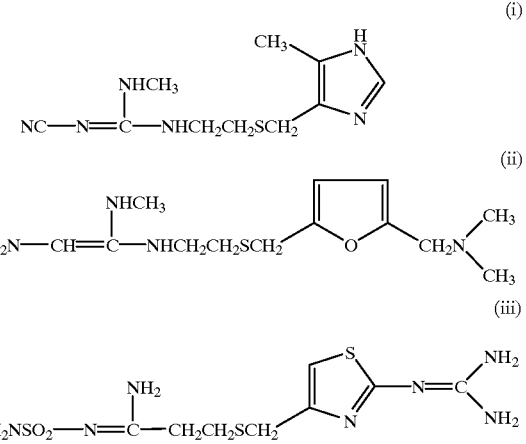

As agricultural insecticide/miticides, organo-phosphorus or carbamate pesticides which are highly toxic to warm-blooded animals have heretofore been employed. However, there has been an emergence of noxious insects, particularly of the order "Hemiptera", which are resistant to these pesticides, and there has been a long-standing need for the development of a pesticide effective against these resistant pests.

Getting impetus from the aforementioned histamine $H_2$ receptor antagonists, the present inventors synthesized various α-unsaturated amines and investigated their activities. As a result, we discovered surprisingly that compounds of the invention which have no alkylene group or only a short alkylene group in the side chain have agriculturally useful insecticidal/miticidal activity.

Based on the above finding, the present inventors conducted further research and have come up with the present invention.

The invention is, thus, concerned with:

(1) novel α-unsaturated amines of the formula:

[I°]

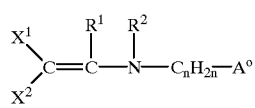

wherein $X^1$ and $X^2$ are such that one is an electron-attracting group with the other being a hydrogen atom or an electron-attracting group; $R^1$ is a group attached through a nitrogen atom; $R^2$ is a hydrogen atom or a group attached through a carbon, nitrogen or oxygen atom; n is an integer equal to 0, 1 or 2; $A°$ is a heterocyclic group, with the proviso that when $R^2$ is a hydrogen atom, $R^1$ is a group of the formula:

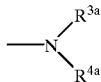

wherein $R^{3a}$ is a hydrogen atom, $C_{1-4}$ alkyl, $C_{7-9}$ aralkyl or $C_{1-4}$ acyl and $R^{4a}$ is a hydrogen atom, $C_{1-4}$ alkyl, $C_{1-4}$ alkoxy-$C_{1-4}$ alkyl, (di-$C_{1-4}$ alkylainino)-$C_{1-4}$ alkyl, tri-$C_{1-4}$ alkylsiolyl-$C_{1-4}$ alkyl, $C_{2-4}$ alkenyl, or pyridylor thiazolyl-$C_{1-2}$alkyl wherein the pyridyl or thiazolyl moiety may optionally be substituted with a halogen atom, or $R^{3a}$ and $R^{4a}$ taken together with the adjacent nitrogen atom constitute pyrrolidino and $A°$ is pyridyl, pyrazinyl or thiazolyl which may optionally be substituted with a halogen $C_{1-4}$ alkyl, $C_{1-4}$ alkylthio or $C_{1-4}$ alkoxy, , or a salt thereof, and (2) insecticidal/pesticidal compositions containing an α-unsaturated amine of the formula:

[I]

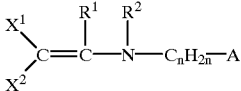

wherein $X^1$ and $X^2$ are such that one is an electron-attracting group with the other being a hydrogen atom or an electron-attracting group; $R^1$ is a group attached through a nitrogen atom; $R^2$ is a hydrogen atom or a group attached through a carbon, nitrogen or oxygen atom; n is an integer equal to 0, 1 or 2; A is a heterocyclic group or a cyclic hydrocarbon group, with the proviso that when $R^1$ is β-N-pyrrolidinoethylamino and $R^2$ is a hydrogen atom, A is a group of the formula:

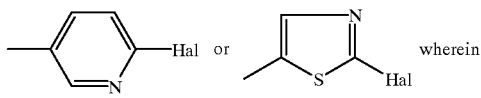

Hal is a halogen atom (e.g. Cl, Br, F, etc.), or a salt thereof, and their production.

Referring to the above formulas [I°] and [I], one of $X^1$ and $X^2$ is an electron-attracting group with the other being a hydrogen atom or an electron-attracting group. The electron-attracting group represented by $X^1$ and $X^2$ includes, among others, cyano, nitro, $C_{1-4}$alkoxy-carbonyl (e.g. methoxycarbonyl, ethoxycarbonyl, etc.), hydroxycarbonyl, $C_{6-10}$aryloxy-carbonyl (e.g. phenoxycarbonyl etc.), heterocycleoxycarbonyl wherein the heterocycle moiety is as mentioned below (e.g. pyridyloxycarbonyl, thienyloxycarbonyl, etc.), $C_{1-4}$alkylsulfonyl which may be substituted with halogen (e.g. methylsulofonyl, trifluoromethylsulfonyl, ethylsulfonyl, etc.), aminosulfonyl, di-$C_{1-4}$alkoxyphosphoryl (e.g. diethoxyphosphoryl, etc.), $C_{1-4}$acyl which may be substituted with halogen (e.g. a $C_{1-4}$alkylcarbonyl such as acetyl, trichloroacetyl, trifluoroacetyl, etc.), $C_{1-4}$alkylsulfonylthiocarbamoyl (e.g. methylsulfonylthiocarbamoyl, etc.), carbamoyl and so on. One of $X^1$ and $X^2$ may be a halogen atom such as fluorine, chlorine, bromine or iodine, and $X^1$ and $X^2$ may join together with the adjacent carbon atom to form a ring such as, for example,

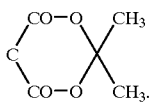

Preferred examples of the group

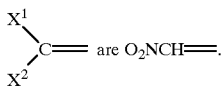

are O₂NCH=.

Referring to the above formulas [I°] and [I], $R^1$ may be a group attached through a carbon, oxygen or sulfur atom, but a group attached through a nitrogen atom is preferred. Thus, for example, a group of the formula

can be used. In the above formula, $R^3$ is for example a hydrogen atom, an alkyl group (for example, a $C_{1-6}$ alkyl groups such as methyl, ethyl, n-propyl, i-propyl, n-butyl, i-butyl, n-hexyl, etc.), an $C_{6-10}$aryl group (for example, phenyl, etc.), an $C_{7-9}$ aralkyl group (for example a phenylalkyl such as benzyl, etc.), a heterocyclic group as mentioned below (for example, pyridyl, etc.), a $C_{1-4}$acyl group (for example, formyl, acetyl, propionyl, etc.), a $C_{6-10}$ arylcarbonyl (for example, benzoyl, etc.), an alkoxycarbonyl group (for example, $C_{1-4}$ alkoxycarbonyl groups such as methoxycarbonyl, ethoxycarbonyl, etc.), a $C_{6-10}$ aryloxycarbonyl group (for example, phenoxycarbonyl, etc.), a heterocycleoxycarbonyl group wherein the heterocycle moiety is as mentioned below (for example, furyloxycarbonyl, etc.), a $C_{6-10}$ arylsulfonyl group (for example, phenylsulfonyl, etc.), an alkylsulfonyl group (for example, $C_{1-4}$ alkylsulfonyl groups such as methylsulfonyl, etc.), a dialkoxyphosphoryl group (for example, di-$C_{1-4}$ alkoxyphosphoryl groups such as diethoxyphosphoryl, etc.), an alkoxy group (for example, $C_{1-4}$ alkoxy groups such as methoxy, ethoxy, etc.), a hydroxy group, an amino group, a dialkylamino group (for example, di-$C_{1-4}$ alkylamino group such as dimethylamino, diethylamino, etc.), an acylamino group (for example, $C_{1-4}$ acylamino groups such as formylamino, acetylamino, propionylamino, etc.), an alkoxycarbonylamino groups (for example, $C_{1-4}$ alkoxycarbonylamino groups such as methoxycarbonylamino, etc.), an alkylsulfonylamino group (for example, $C_{1-4}$ alkylsulfonylamino groups such as methylsulfonylamino, etc.), a di-alkoxyphosphoroylamino group (for example, di-$C_{1-4}$ alkoxyphosphorylamino groups such as diethoxyphosphorylamino, etc.), an $C_{7-9}$ aralkyloxy group (for example, benzyloxy, etc.), an alkoxycarbonylalkyl group (for example, $C_{1-4}$ alkoxy-carbonyl-$C_{1-4}$ alkyl groups such as methoxycarbonylmethyl, etc.) or the like. $R^4$ is for example a hydrogen atom, or an alkyl (for example, $C_{1-4}$ alkyl groups such as methyl, ethyl, etc.), cycloalkyl (for example, $C_{3-6}$ cycloalkyl groups such as cyclohexyl, etc.), alkenyl (for example, $C_{2-4}$ alkenyl groups such as vinyl, allyl, etc.), cycloalkenyl (e.g. $C_{3-6}$ cycloalkenyl groups such as cyclohexenyl, etc.) or alkynyl (for example, $C_{2-4}$ alkynyl groups such as ethynyl, etc.) group which may optionally be substituted by 1 to 3 substituents (e.g. hydroxyl, $C_{1-4}$ alkoxy such as methoxy, halogen such as fluorine, di-$C_{1-4}$ alkylamino such as dimethylamino, $C_{1-4}$ alkylthio such as i-propylthio and n-propylthio, $C_{1-3}$ acylamino such as acetylamino, $C_{1-4}$ alkylsulfonyolamino such as methylsulfonylamino, tri-$C_{1-4}$ alkylsilyl such as trimethylsilyl, pyridyl or thiazolyl which may optionally be substituted with a halogen atom, etc.). Furthermore, $R^3$ and $R^4$ may, taken together with the adjacent nitrogen atom, constitute a 5- or 6-membered cyclic amino group such as

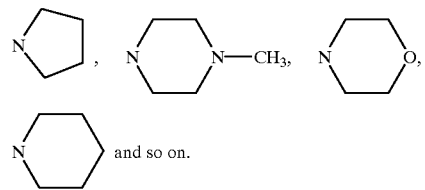

and so on.

The group attached through a nitrogen atom, represented by $R^1$, includes an amino group which may optionally be substituted (for example by any of the alkyl, aryl, aralkyl, heterocyclic, acyl, alkoxycarbonyl, aryloxycarbonyl, heterocycleoxycarbonyl, arylsulfonyl, alkylsulfonyl, dialkoxyphosphoryl, cycloalkyl, alkenyl, cycloalkenyl and alkynyl groups mentioned in the above definition of $R^3$ and $R^4$) such as di-substituted amino groups, e.g. di-$C_{1-6}$ alkylamino, N-$C_{1-6}$ alkyl-N-formylamino, etc., mono-substituted amino groups, e.g. mono-$C_{1-6}$ alkylamino etc., and unsubstituted amino, a hydrazino group which may optionally be substituted (for example by any of the alkyl, acyl, alkoxycarbonyl, alkylsulfonyl, dialkoxyphosphoryl and other groups mentioned in the above definition of $R^3$) or a hydroxyamino group which may optionally be substituted (for example by any of the alkyl, aralkyl and other groups mentioned in the above description of $R^3$).

$R^2$ is a hydrogen atom or a group attached through a carbon, nitrogen or oxygen atom. The group attached through a carbon atom, $R^2$, includes, among others, $C_{1-4}$ acyl (for example, formyl, acetyl, propionyl, etc.), alkyl (for example, $C_{1-4}$ alkyl groups such as methyl, ethyl, n-propyl, i-propyl, n-butyl, i-butyl, sec-butyl, etc.), alkenyl (for example, $C_{2-4}$ alkenyl groups such as vinyl, allyl, etc.), cycloalkyl (for example, $C_{3-6}$ cycloalkyl groups such as cyclopentyl, cyclohexyl, etc.), $C_{6-10}$ aryl (for example, phenyl, naphthyl, etc.), $C_{7-9}$ aralkyl (for example phenylalkyl such as benzyl, etc.) and heterocyclic as mentioned below which has a free bond on a carbon atom thereof (for example, 3- or 4-pyridyl, etc.). These groups may each be substituted by 1 to 3 substituents (for example, $C_{1-4}$ alkylthio groups such as methylthio, ethylthio, etc., $C_{1-4}$ alkoxy groups such as methoxy, ethoxy, etc., mono- or di-$C_{1-4}$ alkylamino groups such as methylamino, dimethylamino, etc., $C_{1-4}$ alkoxy-carbonyl groups such as methoxycarbonyl, ethoxycarbonyl, etc., $C_{1-4}$ alkylsulfonyl groups such as methylsulfonyl, ethylsulfonyl, etc., halogen atoms such as fluorine, chlorine, bromine iodine, etc., $C_{1-4}$ acyl groups including alkanoyls such as acetyl, etc., benzoyl, phenylsulfonyl, pyridyl and so on). The group attached through a nitrogen atom, $R^2$, includes, among others, the groups mentioned in the definition of $R^1$. The group attached through an oxygen atom, $R^2$, includes, among others, alkoxy (for example, $C_{1-4}$ alkoxy groups such as methoxy, ethoxy, etc.), cycloalkoxy (for example, $C_{3-6}$ cycloalkoxy groups such as cyclohexyloxy etc.), alkenyloxy (for example, $C_{2-4}$ alkenyloxy groups such as vinyloxy, allyloxy, etc.), cycloalkenyloxy (for example, $C_{3-6}$ cycloalkenyloxy groups such as cyclohexenyloxy etc.), alkynyloxy (for example, ethynyloxy etc.), $C_{6-10}$ aryloxy (for example, phenoxy, etc.), heterocycleoxy wherein the heterocycle moiety is as mentioned below (for example, thienyloxy etc.) and hydroxyl. These groups may each have 1 to 3 substituents (for example, halogen such as fluorine, chlorine, bromine, phenyl and so on). $R^2$ is preferably a group attached through a carbon, nitrogen or oxygen group, such as formyl, an alkyl group (particularly $C_{1-4}$ alkyl groups such as methyl, ethyl, etc.) which may optionally be substituted (for example by the $C_{1-4}$ alkylthio, $C_{1-4}$ alkoxy, mono- or di-$C_{1-4}$ alkylamino, $C_{1-4}$ alkoxycarbonyl, $C_{1-4}$ alkylsulfonyl, acetyl, benzoyl, phenylsulfonyl, pyridyl, etc.), an amino group- which may optionally be substituted (for example, those mentioned in the definition of $R^1$) and a hydroxyl group which may optionally be substituted) for example by the above-mentioned $C_{1-4}$ alkyl, $C_{3-6}$ cycloalkyl, $C_{2-4}$ alkenyl, $C_{3-6}$ cycloalkenyl, $C_{2-4}$ alkynyl, $C_{6-10}$ aryl and heterocyclic groups (particularly $C_{1-4}$ alkoxy groups such as methoxy and so on). The symbol n means 0, 1 or 2. Therefore, —$C_nH_{2n}$— in the formulas [I°] and [I] represents a single bond, —$CH_2$—,

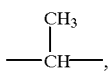

although the single bond or —$CH_2$— is preferred. The symbols A° and A mean a heterocyclic group as mentioned below (such as 3-pyridyl, 6-chloro-3-pyridyl, 6-methoxy-3-pyridyl, 6-methyl-3-pyridyl, 3-quinolyl, etc.), preferably one which may optionally be substituted with one to three of the choices (i), (iv), (Viii), (XVii), (XLVi), (XLViii) and so on as mentioned below, or a cyclic hydrocarbon group as mentioned below (such as cyclopropyl, cyclohexyl, phenyl, p-chlorophenyl and so on), preferably one which may optionally be substituted with one or two of the choice (XVii) as mentioned below, The heterocyclic group of A° or A is more preferably a pyridyl or thiazolyl group which may optionally be substituted, such as 3-pyridyl, 6-chloro-3-pyridyl,6-brono-3-pyridyl, 2-chloro-5-thiazolyl and so on. The cyclic hydrocarbon group A is more preferably a halophenyl group such as p-chlorophenyl and so on.

As the alkyl, cycloalkyl, alkenyl, cycloalkenyl, alkynyl, aryl, aralkyl, heterocyclic and cyclic hydrocarbon groups in the definitions of $X^1$, $X^2$, $R^1$, $R^2$, $R^3$, $R^4$, A° and A, the following groups, among others, may be employed and each of these groups may have 1 to 5 substituents such as (i) through (Lii) which appear hereinafter.

The alkyl group preferably contains 1 to 20 carbon atoms and is more preferably a group of 1 to 8 carbon atoms. This alkyl group may be straight-chain or branched. Specific examples of the alkyl group include methyl, ethyl, propyl, isopropyl, butyl, isobutyl, sec-butyl, tert-butyl, pentyl, hexyl, heptyl, octyl, nonyl, 2-ethylhexyl, decyl, undecyl, dodecyl, tridecyl, tetradecyl, pentadecyl, hexadecyl, octadecyl, nonadecyl, eicosyl and so on.

The cycloalkyl group is preferably a group of 3 to 6 carbon atoms, such as cyclopropyl, cyclobutyl, cyclopentyl, cyclohexyl and so on.

The alkenyl group is preferably a group of 2 to 6 carbon atoms. Specific examples of such alkenyl group include vinyl, allyl, isopropenyl, methallyl, 1,1-dimethylallyl, 2-butenyl, 3-butenyl, 2-pentenyl, 4-pentenyl, 5-hexenyl and so on.

The cycloalkenyl group is preferably a group of 3 to 6 carbon atoms, such as 1-cyclopropenyl, 2-cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl, 1,3-cyclohexadien-1-yl, 1,4-cyclohexadien-1-yl, 1,3-cyclopentadien-1-yl, 2,4-cyclopentadien-1-yl and so on.

The alkynyl group is preferably a group of 2 to 6 carbon atoms, such as ethynyl, propargyl, 2-butyn-1-yl, 3-butyn-1-yl, 3-butyn-2-yl, 1-pentyn-3-yl, 3-pentyn-1-yl, 4-pentyn-2-yl, 3-hexyn-1-yl and so on.

The aryl group may for example be phenyl or naphthyl.

The aralkyl group may for example be benzyl, phenethyl, naphthylmethyl or the like.

The heterocyclic group includes, among others, 5- to 8-membered rings each containing 1 to 5 hetero atoms such as oxygen, sulfur and nitrogen or fused rings derived therefrom, such as 2- or 3- thienyl, 2- or 3- furyl, 2- or 3- pyrrolyl, 2-, 3- or 4- pyridyl, 2-, 4- or 5- oxazolyl, 2-, 4- or 5- thiazolyl, 3-, 4- or 5- pyrazolyl, 2-, 4- or 5- imidazolyl, 3-, 4- or 5- isoxazolyl, 3-, 4- or 5- isothlazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H tetrazolyl, N-oxido- 2-, 3- or 4- pyridyl, 2-, 4- or 5-pyrimidinyl, N-oxido-2-, 4- or 5- pyrimidinyl, 3- or 4-pyridazinyl, pyrazinyl, N-oxido-3- or 4-pyridazinyl, benzofuryl, benzothiazolyl, benzoxazolyl, triazinyl, oxotriazinyl, tetrazolo[1,5-b]pyridazinyl, triazolo[4,5-b] pyridazinyl, oxoimidazinyl, dioxotriazinyl, pyrrolidinyl, piperidionyl, pyranyl, thiopyranyl, 1,4-oxazinyl, morpholinyl, 1,4-thiazinyl, 1,3-thiazinyl, piperazinyl, benzimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl, phenoxazinyl and so on.

The cyclic hydrocarbon group includes, among others, $C_{3-6}$ cycloalkyl groups such as cyclopropyl, cyclobutyl, cyclopentyl, cyclohexyl, etc., $C_{3-6}$ cycloalkenyl groups such as 1-cyclopropenyl, 2-cyclobutenyl, 1-cyclohexenyl, 2-cyclohexenyl, 1,3-cyclohexadien-1-yl, etc., and $C_{6-10}$ aryl groups such as phenyl, naphthyl and so on.

(i) $C_{1-4}$ Alkyl groups such as methyl, ethyl, propyl, isopropyl, butyl, isobutyl, sec-butyl, tert-butyl, etc. are used.

(ii) $C_{3-6}$ Cycloalkyl groups such as cyclopropyl, cyclobutyl, cyclopentyl, cyclohexyl, etc. are used.

(iii) $C_{6-10}$ Aryl groups such as phenyl, naphthyl, etc. are used.

(iv) $C_{1-4}$ Alkoxy groups such as methoxy, ethoxy, propoxy, isopropoxy, butoxy, tert-butoxy, etc. are used.

(v) $C_{3-6}$ Cycloalkyloxy groups such as cyproopyloxy, cyclopentyloxy, cyclohexyloxy, etc. are used.

(vi) $C_{6-10}$ Aryloxy groups such as phenoxy, naphthyloxy, etc. are used.

(vii) $C_{7-12}$ Aralkyloxy groups such as benzyloxy, 2-phenethyloxy, 1-phenethyloxy, etc. are used.

(viii) C1-4 Alkylthio groups such as methylthio, ethylthio, propylthio, butylthio, etc. are used.

(ix) $C_{3-6}$ Cycloalkylthio groups such as cyclopropylthio, cyclopentylthio, cyclohexylthio, etc. are used.

(x) $C_{6-10}$ Arylthio groups such as phenylthio, naphthylthio, etc. are used.

(xi) $C_{7-12}$ Aralkylthio groups such as benzylthio, 2-phenethylthio, 1-phenethylthio, etc. are used.

(xii) Mono-$C_{1-4}$ alkylamino groups such as methylamino, ethylamino, propylamino, isopropylamino, butylamino, isobutylamino, tert-butylaminio, etc. are used.

(xiii) Di-$C_{1-4}$ alkylamino groups such as dimethylamino, diethylamino, dipropylamino, dibutylamino, N-methyl-N-ethylamino, N-methyl-N-propylamino, N-methyl-N-butyl-amino, etc. are used.

(xiv) $C_{3-6}$ Cycloalkylamino groups such as cyclopropylamino, cyclopentylamino, cyclohexylamino, etc. are used.

(xv) $C_{6-10}$ Arylamino groups such as anilino etc. are used.

(xvi) $C_{7-12}$ Aralkylamino groups such as benzylamino, 2-phenethylamino, 1-phenethylamino, etc. are used.

(xvii) Halogen atoms such as fluorine, chlorine, bromine and iodine are used.

(xviii) $C_{1-4}$ Alkoxycarbonyl groups such as methoxycarbonyl, ethoxycarbonyl, propoxycarbonyl, isopropoxycarboyl, butoxycarbonyl, tert-butoxycarbonyl, isobutoxycarbonyl, etc. are used.

(xix) $C_{6-10}$ Aryloxycarbonyl groups such as phenoxycarbonyl etc. are used.

(xx) $C_{3-6}$ Cycloalkyloxycarbonyl groups such as cyclopropyloxycarbonyl, cyclopentyloxycarbonyl, cyclohexyloxycarbonyl, etc. are used.

(xxi) $C_{7-12}$ Aralkyloxycarbonyl groups such as benzyloxycarbonyl, 1-phenethyloxycarbonyl, 2-phenethyloxycarbonyl, etc. are used.

(xxii) $C_{1-5}$ Alkanoyl groups such as formyl, acetyl, propionyl, butyryl, pivaloyl, etc. are used.

(xiii) $C_{1-15}$ Alkanoyloxy groups such as formyloxy, acetoxy, butyryloxy, pivaloyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, etc. are used.

(xxiv) Carbamoyl groups which may optionally be substituted, such as carboaomoyl, N-methylcarbamoyl, N,N-dimethylcarbamoyl, N-ethylcarboamoyl, N,N-diethylcarbamoyl, N-phenylcarboaomoyl, pyrrolidinocarbamoyl, piperidinocarbamoyl, piperazinocarbamoyl, morpholinocarbamoyl, N-benzylcarbamoyl, etc. are used.

(xxv) Substituted carbamoyloxy groups such as N-methylcarbamoyloxy, N,N-dimethylcarbamoyloxy, N-ethylcarbamoyloxy, N-benzylcarbamoyloxy, N,N-dibenzylcarboaomoyloxy, N-phenylcarbamoyloxy, etc. are used.

(xxvi) $C_{1-4}$ Alkanoylamino groups such as formylamino, acetamido, propionamide, butyramido, etc. are used.

(xxvii) $C_{6-10}$ Arylcarbonylamino groups such as benzamido etc. are used.

(xxviii) $C_{1-4}$ Alkoxycarbonylamino groups such as methoxycarbonylamino, ethoxycarbonylamino, butoxycarbonylamino, tert-butoxycarbonylamino, etc. are used.

(xxix) $C_{7-12}$ Aralkyloxycarbonylamino groups such as benzyloxycarbonylamino, 4-methoxybenzyloxycarbonylamino, 4-nitrobenzyloxycarbonylamino, 4-chlorobenzyloxycarbonylamino, etc. are used.

(xxx) Substituted sulfonylamino groups such as methanesulfonylamino, ethanesulfonylamino, butanesulfonylamino, benzensulfonylamino, toluenesulfonylamino, naphthalenesulfonylamino, trifluoromethanesulfonylamino, 2-chloroethanesulfonylamino, 2,2,2-trifluoromethanesulfonylamino, etc. are used.

(xxxi) Heterocyclic groups nuclearly containing 1 to 5 hetero atoms of N, O and/or S, such as pyrrolidinyl, pyrrolyl, pyrazolyl, imidazolyl, furyl, thienyl, oxazolyl, isoxazolyl, isothiazolyl, thiazolyl, piperidinyl, pyridyl, piperazinyl, pyrimidinyl, pyranyl, tetrahydropyranyl, tetrahydrofuryl, indolyl, quinolyl, 1,3,4-oxadiazolyl, thieno[2,3-d]pyridyl, 1,2,3-thiadiazolyl, 1,3,4-thladiazolyl, 1,2,3-triazolyl, 1,2,4-triazolyl, 1,3,4-triazolyl, tetrazolyl, 4,5-dihydro-1,3-dioxazolyl, tetrazolo[1,5-b]pyridazinyl, benzothiazolyl, benzoxazolyl, benzimidazolyl, benzothienyl, etc. are used.

(xxxii) Heterocyclethio, heterocycleoxy, heterocycleamino, and heterocyclecarbonylamino groups and groups derived therefrom by attachment of any of heterocyclic groups (xxxi) to the S, O, N atom or the carbonylamino group are used.

(xxxiii) Di-$C_{1-4}$ alkylphosphinothioylamino groups such as dimethylphosphinothioylamino, diethylphosphinothioylamino, etc. are used.

(xxxiv) Alkoxyimino groups such as methoxyimino, ethoxyimino, 2-fluoroethoxyimino, carboxymethoxyimino, 1-carboxy-1-methylethoxyimino, 2,2,2-trichloroethoxycarbonylmethoxyimino, 1-(2,2,2-trichloroethoxycarbonyl)-1-methylethoxyimino, (2-aminothiazol-4-yl)methoxyimino, (1H-imidazol-4-yl)methoxyimino, etc. are used.

(xxxy) $C_{1-4}$ Alkylsulfonyloxy groups such as methanesulfonyloxy, ethanesulfonyloxy, butanesulfonyloxy, etc. are used.

(xxxvi) $C_{6-10}$ Arylsulfonyloxy groups such as benzenesulfonyloxy, toluenesulfonyloxy, etc. are used.

(xxxvii) Di-$C_{6-10}$ arylphosphinothioylamino groups such as diphenylphosphinothioylamino, etc. are used.

(xxxviii) Thiocarbamoylthio groups which may optionally be substituted, such as thiocarbamoylthio, N-methylthiocarbamoylthio, N,N-dimethylthiocarbamoylthio, N-ethylthiocarbamoylthio, N-benzylthiocarbamoylthio, N,N-dibenzylthiocarbanoylthio, N-phenylthiocarbamoylthio, etc. are used.

(xxxix) Silyloxy groups such as trimethylsilyloxy, t-butyldimethylsilyloxy, t-butyldiphenylsilyloxy, dimethylphenylsilyloxy, etc. are used.

(xL) Silyl groups such as trimethylsilyl, t-butyldimethylsilyl, t-butyldiphenylsilyl, dimethylphenylsilyl, etc. are used.

(xLi) $C_{1-4}$ Alkylsulfinyl groups such as methylsulfinyl, ethylsulfinyl, propylsulfinyl, butylsulfinyl, etc. are used.

(xLii) $C_{6-10}$ Arylsulfinyl groups such as phenylsulfinyl, naphthylsulfinyl, etc. are used.

(xLiii) $C_{1-4}$ Alkylsulfonyl groups such as methanesulfonyl, ethanesulfonyl, butanesulfonyl, etc. are used.

(xLiv) $C_{6-10}$ Arylsulfonyl groups such as benzenesulfonyl, toluenesulfonyl, etc. are used.

(xLv) $C_{1-4}$ Alkoxycarbonyloxy groups such as methoxycarbonyloxy, ethoxycarbonyloxy, tert-butoxycarbonyloxy, etc. are used.

(xLvi) Halo-$C_{1-4}$ alkyl groups such as trifluoromethyl, 1,1,2,2-tetrafluoroethyl, difluoromethyl, monofluoromethyl, trichloromethyl, dichloromethyl, monochloromethyl, etc. are used.

(xLvii) Halo-$C_{1-4}$ alkoxy, halo-$C_{1-4}$ alkylthio, halo-$C_{1-4}$ alkylsulfinyl and halo-$C_{1-4}$ alkylsulfonyl groups as well as groups derived therefrom by attachement of any of halo-$C_{1-4}$ alkyl groups (xLvi) to the O, S, sulfinyl and sulfonyl moieties thereof are used.

(xLviii) Cyano, nitro, hydroxy, carboxyl, sulfo and phosphono groups are used.

(xLix) $C_{1-4}$ Alkyloxysulfonyl groups such as methoxysulfonyl, ethoxysulfonyl, butoxysulfonyl, etc. are used.

(L) $C_{6-10}$ Aryloxysulfonyl groups such as phenoxysulfonyl, tolyloxysulfonyl, etc. are used.

(Li) $C_{7-12}$ Aralkyloxysulfonyl groups such as benzyloxysulfonyl, 2-phenethyloxysulfonyl, 1-phenethyloxysulfonyl, etc. are used.

(Lii) Di-$C_{1-4}$-alkyloxyphosphoryl groups such as dimethoxyphosphoryl, diethoxyphosphoryl, dibutoxyohosohoryl, etc. are used.

Preferred examples of the unsaturated amines of formulas [I°] and [I] or salts thereof include:

The α-unsaturated amines of the formula:

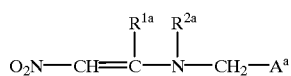

[$I^a$]

wherein $R^{1a}$ is a mono-$C_{1-6}$ alkylamino group, an N-$C_{1-6}$ alkyl-N-formylamino group or an amino group; $R^{2a}$ is an $C_{1-4}$ alkyl group or an $C_{1-4}$ alkoxy group; $A^a$ is a chloropyridyl group, or salts thereof;

the α-unsaturated amines of the formula:

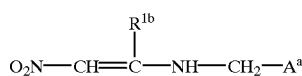

[$I^b$]

wherein $R^{1b}$ is a mono-$C_{1-6}$ alkylamino group or an N-$C_{1-6}$ alkyl-N-formylamino group; $A^a$ has the meaning defined hereinbefore, or salts thereof;

the α-unsaturated amines of the formula:

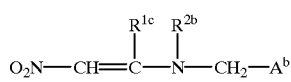

[$I^c$]

wherein $R^{1c}$ is a di-$C_{1-6}$ alkylamino group; $R^{2b}$ is a hydrogen atom, a formyl group or an $C_{1-4}$ alkyl group; $A^b$ is a pyridyl group or a chloropyridyl group, or salts thereof; and the α-unsaturated amines of the formula:

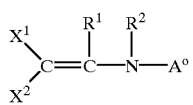

[$I^d$]

wherein the symbols have the meanings defined hereinbefore, or salts thereof.

Referring to the above formulas [$I^a$], [$I^b$] and [$I^c$], the mono-$C_{1-6}$ alkylamino group represented by $R^{1a}$ or $R^{1b}$ includes, among others, monomethylamino, monoethylamino, mono-n-propylamino, mono-i-proonylamino, mono-n-butylamino, mono-i-butylamino, mono-n-hexylamino, etc. and preferably mono-$C_{1-4}$-alkyl amino groups such as mono-methylamino, monoethylamino and so on. The N-$C_{1-6}$ alkyl-N-formylamino group represented by $R^{1a}$ or $R^{1b}$ includes, among others, N-methyl-N-formylamino, N-ethyl-N-formylamino, N-n-propyl-N-formylamino, N-i-propyl-N-formylamino, N-n-butyl-N-formylamino, N-n-hexyl-N-foromylamino, etc. and preferably N-$C_{1-4}$ alkyl-N-formylamino groups such as N-methyl-N-formylamino, N-ethyl-N-formylamino and so on. The di-$C_{1-6}$ alkylamino group represented by $R^{1c}$ includes, among others, dimethylamino, N-ethyl-N-methylamino, diethylamino, di-n-propylamino, di-i-propylamino, di-n-butylamino, di-i-butylamino, di-n-pentylamino, di-i-pentylamino, di-n-hexylamino, etc. and preferably di-$C_{1-4}$ alkylamino groups such as dimethylamino, N-ethyl-N-methyhylamionio and diethylamino.

The $C_{1-4}$ alkyl group represented by $R^{2a}$ or $R^{2c}$ includes, among others, the alkyl groups mentioned in the definition of $R^2$ above and preferably methyl, ethyl and so on. The $C_{1-4}$ alkoxy group represented by $R^{2a}$ includes, among others, the alkoxy groups mentioned in the definition of $R^2$ above and preferably methoxy, ethoxy and so on. The chloropyridyl group represented by $A^a$ or $A^b$ includes, among others, 2-chloro-3-pyridyl, 4-chloro-3-pyridyl, 5-chloro-3-pyridyl, 6-chloro-3-pyridyl, 3-chloro-4-pyridyl, etc. and preferably 6-chloro-3-pyridyl and so on. The pyridyl group represented by $A^b$ includes 3-pyridyl, 4-pyridyl, etc. and preferably 3-pyridyl.

Typical α-unsaturated amines of formulas [I°] and [I] or salts thereof include:

The α-unsaturated amines of the formula:

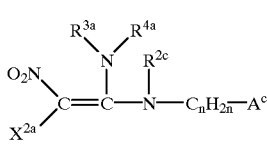

[$I^e$]

wherein $X^{2a}$ is a hydrogen atom, $C_{1-4}$ alkoxycarbonyl or $C_{1-4}$ alkylsulfonylthiocarbamoyl; $R^{2c}$ is a hydrogen atom, $C_{1-3}$ acyl, $C_{1-4}$ alkyl, mono- or di- $C_{1-4}$ alkoxy-$C_{1-4}$ alkyl, $C_{7-9}$ aralkyl, mono- or di- $C_{1-4}$ alkylamino or $C_{1-4}$ alkoxy; $A^c$ is 3- or 4- pyridyl, pyrazinyl or 4- or 5- thiazolyl which may optionally be substituted with halogen, $C_{1-4}$ alkyl or $C_{1-4}$ alkoxy; and $R^{3a}$, $R^{4a}$ and n are as defined above, or salts thereof;

the α-unsaturated amines of the formula:

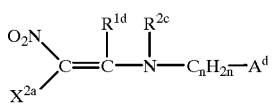
[I$^f$]

wherein X$^{2a}$ is a hydrogen atom, C$_{1-4}$ alkoxycarbonyl or C$_{1-4}$ alkylsulfonylthiocarbamoyl; R$^{1d}$ is amino, mono- or di-C$_{1-4}$ alkylamino, N- C$_{1-4}$ alkyl- N- C$_{1-3}$ acylamino, C$_{7-9}$ aralkylamino, halogenothiazolyl- C$_{1-2}$ alkylamino or C$_{1-4}$ alkoxy -C$_{1-2}$ alkylamino; R$^{2c}$ is a hydrogen atom, C$_{1-3}$ acyl, C$_{1-4}$ alkyl, mono- or di- C$_{1-4}$ alkoxy- C$_{1-4}$ alkyl, C$_{7-9}$ aralkyl, mono- or di-C$_{1-4}$ alkylamino or C$_{1-4}$ alkoxy;

n is an integer equal to 0, 1 or 2; and A$^d$ is 3- or 4-pyridyl, pyrazinyl or 5-thiazolyl which may optionally be substituted with halogen, C$_{1-4}$ alkyl or C$_{1-4}$ alkoxy, or salts thereof;

the α-unsaturated amines of the formula:

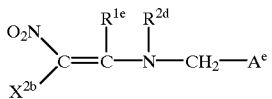
[I$^g$]

wherein X$^{2b}$ is a hydrogen atom or C$_{1-2}$alkylsulfonylthiocarbamoyl; R$^{1e}$ is amino, mono- or di-C$_{1-2}$alkylamino or N-C$_{1-2}$alkyl-N-formylamino; R$^{2d}$ is a hydrogen atom, C$_{1-2}$alkyl or C$_{1-3}$acyl; and A$^e$ is a group of the formula:

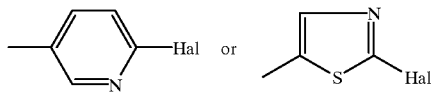

wherein Hal is a halogen atom, or salts thereof;

the α-unsaturated amines of the formula:

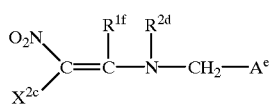
[I$^h$]

wherein X$^{2c}$ is a hydrogen atom or methylsulfonylthiocarbamoyl; R$^{1f}$ is amino, methylamino, dimethylamino or N-methyl-N-formylamino ; R$^{2d}$ is a hydrogen atom, formyl or C$_{1-2}$alkyl ; and A$^e$ is a group of the formula:

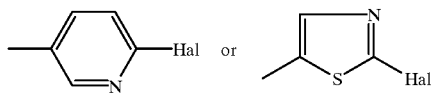

wherein Hal is a halogen atom, or salts thereof; and the α-unsaturated amines of the formula:

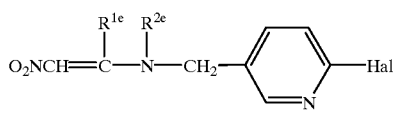
[I$^i$]

wherein R$^{1e}$ is amino, mono- or di-C$_{1-2}$alkylamino or N-C$_{1-2}$alkyl-N-formylamino ; R$^{2e}$ is C$_{1-2}$alkyl or formyl and Hal is a halogen atom, or salts thereof.

In the above formulas [I$^e$] to [I$^i$], the groups represented by X$^{2a}$, X$^{2b}$ and X$^{2c}$, the groups represented by R$^{1d}$, R$^{1e}$ and R$^{1f}$, the groups represented by R$^{2c}$, R$^{2d}$ and R$^{2e}$, and the groups represented by A$^c$, A$^d$ and A$^e$ are as mentioned above in the case of X$^2$, R$^1$, R$^2$, A° and A.

The compound [I]or its salt can be produced by the analogous known processes and further by the following processes, for instance.

Process 1)

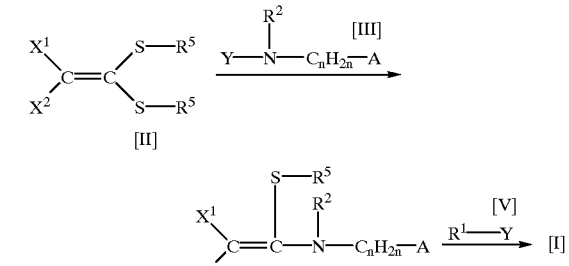

or

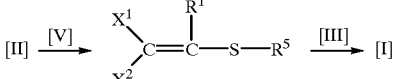

wherein X$^1$, X$^2$, R$^1$, R$^2$, n and A have the meanings defined hereinbefore; R$^5$ is an C$_{1-4}$ alkyl group such as methyl, ethyl, etc. or an C$_{7-9}$aralkyl group such as benzyl etc.; Y is a hydrogen atom or an alkali metal such as sodium, potassium, etc.

Process 2)

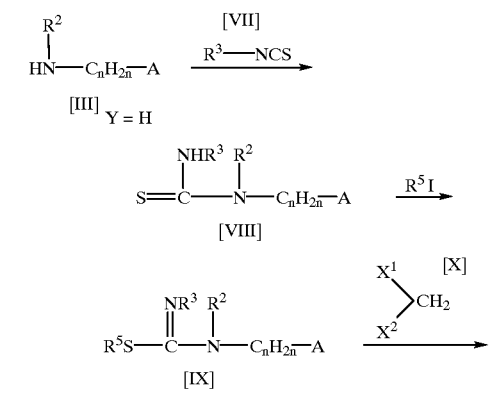

-continued $$\underset{X^2}{\overset{X^1}{>}}C=\underset{\phantom{N}}{\overset{NHR^3\phantom{X}R^2}{\underset{|\phantom{X}}{C}-\underset{|}{N}-C_nH_{2n}-A}}$$
[I-1]

or $$[\mathrm{III}]_{Y=H}\xrightarrow{[\mathrm{VII}']\ R^4-NCS}$$

$$S=\underset{\phantom{N}}{\overset{NHR^4\phantom{X}R^2}{\underset{|\phantom{X}}{C}-\underset{|}{N}-C_nH_{2n}-A}}\xrightarrow{R^5I}$$
[VIII']

$$R^5S-\underset{\phantom{N}}{\overset{NR^4\phantom{X}R^2}{\underset{\|\phantom{X}}{C}-\underset{|}{N}-C_nH_{2n}-A}}\xrightarrow{[X]}$$
[IX']

$$\underset{X^2}{\overset{X^1}{>}}C=\underset{\phantom{N}}{\overset{NHR^4\phantom{X}R^2}{\underset{|\phantom{X}}{C}-\underset{|}{N}-C_nH_{2n}-A}}$$
[I-2]

or $$R^1-H \xrightarrow{[\mathrm{VII}'']\ A-C_nH_{2n}-NCS}$$
[V] Y = H $$S=\underset{\phantom{N}}{\overset{R^1}{\underset{|}{C}-NH-C_nH_{2n}-A}}\xrightarrow{R^5I}$$
[VII'']

$$R^5S-\underset{\phantom{N}}{\overset{R^1}{\underset{\|}{C}=N-C_nH_{2n}-A}}\xrightarrow{[X]}$$
[IX'']

$$\underset{X^2}{\overset{X^1}{>}}C=\underset{\phantom{N}}{\overset{R^1}{\underset{|}{C}-NH-C_nH_{2n}-A}}$$
[I-3]

wherein $X^1$, $X^2$, $R^1$, $R^2$, $R^3$, $R^4$, $R^5$, n and A have the meanings defined hereinbefore.

Process 3)

$$O_2N-CH=\underset{\phantom{X}}{\overset{Hal}{\underset{Hal}{C}}} \text{ or } O_2N-CH_2O(Hal)_3 \xrightarrow[\text{ii) [V]}]{\text{i) [III]}} [\mathrm{I}]$$
[XI] [XII]

or $$[\mathrm{XI}] \text{ or } [\mathrm{XII}] \xrightarrow[\text{ii) [III]}]{\text{i) [V]}} [\mathrm{I}]$$

wherein Hal is the meanings defined hereinbefore.

Process 4)

$$\underset{X^2}{\overset{X^1}{>}}CH-\underset{\phantom{N}}{\overset{R^2}{\underset{|}{CON-C_nH_{2n}-A}}} \xrightarrow{\text{halogenating agent}}$$
[XIII]

$$\underset{X^2}{\overset{X^1}{>}}C=\underset{\phantom{N}}{\overset{Hal\phantom{X}R^2}{\underset{|\phantom{X}}{C}-\underset{|}{N}-C_nH_{2n}-A}} \xrightarrow{[V]} [\mathrm{I}]$$
[XIV]

or $$\underset{X^2}{\overset{X^1}{>}}CH-COR^1 \xrightarrow{\text{halogenating agent}}$$
[XV]

$$\underset{X^2}{\overset{X^1}{>}}C=\underset{\phantom{C}}{\overset{R^1}{\underset{|}{C}-Hal}} \xrightarrow{[\mathrm{III}]} [\mathrm{I}]$$
[XVI]

wherein $X^1$, $X^2$, $R^1$, $R^2$, Hal, n and A have the meanings defined hereinbefore.

Process 5)

$$\underset{X^2}{\overset{X^1}{>}}C=\underset{\phantom{N}}{\overset{R^1\phantom{X}R^2}{\underset{|\phantom{X}}{C}-\underset{|}{N}H}} \xrightarrow[\phantom{XXXX}]{[XVIII]\ A-C_nH_{2n}-Hal} [\mathrm{I}]$$
[XVII]

wherein $X^1$, $X^2$, $R^1$, $R^2$, Hal, n and A have the meanings defined hereinbefore.

Process 6)

$$\underset{R^5OOC}{\overset{X^3}{>}}C=\underset{\phantom{N}}{\overset{R^1\phantom{X}R^2}{\underset{|\phantom{X}}{C}-\underset{|}{N}-C_nH_{2n}-A}} \xrightarrow[\text{ii) Decarboxylation}]{\text{i) Hydrolysis}}$$
[XIX]

$$\underset{H}{\overset{X^3}{>}}C=\underset{\phantom{N}}{\overset{R^1\phantom{X}R^2}{\underset{|\phantom{X}}{C}-\underset{|}{N}-C_nH_{2n}-A}}$$
[I-4]

wherein $R^1$, $R^2$, n, A and $R^5$ have the meanings defined hereinbefore; $X^3$ is an electron-attracting group.

Process 7)

$$\underset{X^2}{\overset{X^1}{>}}C=\underset{\phantom{N}}{\overset{R^6\phantom{X}R^2}{\underset{|\phantom{X}}{C}-\underset{|}{N}-C_nH_{2n}-A}} \text{ or}$$
[I-5]

-continued

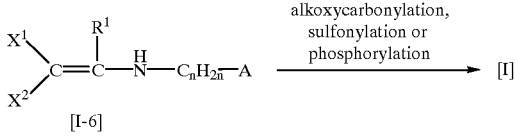

Alkylation, acylation, alkoxycarbonylation, sulfonylation or phosphorylation [I]

wherein $X^1$, $X^2$, $R^1$, $R^2$, n and A have the meanings defined hereinbefore; $R^6$ is a group attached through a nitrogen atom containing at least one hydrogen atom.

In the processes 1) to 7), the compounds [III], [IV] [V], [VI], [IX], [IX'], [IX"], [X], [XIV], [XVI], [XVII], [XVIII], [XIX], [I-5], [I-6] and so on may be used in a form of a salt (e.g. one as mentioned below in a salt of the compound [I]).

In accordance with the aforementioned Process 1), a compound of general formula [II] is reacted with an amino compound of general formula [III] or a salt thereof to give a compound of general formula [IV] which is then reacted with an amino compound of general formula [V] or a salt thereof, or a compound of general formula [II] is reacted with a compound of general formula [V] to give a compound of general formula [VI] which is then reacted with a compound of general formula [III], to thereby give a compound [I]. In practicing the Process 1), the reactions of [II]→[IV], [IV]→[I], [VI]→[VI] and [VI]→[I] may respectively be conducted in an appropriate solvent. There is no limitation on such a solvent provided that it does not interact with the reactant, reagent or reaction product to give byproducts but a solvent capable of dissolving both the reactant and reagent is preferred. As examples of such solvent, there may be mentioned alcohols such as methanol, ethanol, propanol, butanol, etc., aromatic hydrocarbons such as benzene, toluene, xylene, etc., ethers such as diethyl ether, dipropyl ether, dibutyl ether, tetrahydrofuran, dioxane, etc., nitrioles such as acetonitrile, propionitrile, etc., acid amides such as dimethylformamide, dimethylacetamide, etc., sulfoxides such as dimethyl fulfoxide, etc., sulfones such as sulfolane, etc., and phosphoramides such as nexamethyovphosphoramide etc., as well as various mixtures thereof and mixtures thereof with water. While each of the above reactions is generally conducted at atmospheric pressure, it is possible to conduct the reaction under reduced pressure as taught by Japanese Unexamined Patent Application KOKAI-62-138478 (1987) to remove the byproduct low-boiling thiol and thereby suppress the secondary reaction. When a low-boiling solvent is used, the reaction is preferably conducted at supratmospheric pressure. For the aforesaid respective reactions, the reaction temperature may range from 30 to 150° C. and preferably from 50 to 150° C. The reaction time is generally 5 minutes to 48 hours, depending on the reaction temperature, reactant, reagent and solvent. The proportions of reagents [III] and [V] in the reactions [II]→[IV] and [II]→[VI] may each be 1 to 1.2 molar equivalents relative to [II]. The use of [III] and [V] in further excess is preferably avoided to prevent by-production of the diamino compound. As the reaction [II]→[IV] and [II]→[VI] in a concentrated reaction mixture may occasionally give the by-product, the diamino compound, it is desirable to avoid the reactions in such condition. The proportions of reagents [V] and [III] in the reactions [IV]→[I] and [VI]→[I] are generally 1 to 1.5 molar equivalents and, unlike in the reactions [II]→[IV] and [II]→[VI], the use of [V] or [III] in greater excess may not occasionally induce byproduct formation. A base may be permitted to be concomitantly present for the purpose of promoting the reaction or suppressing secondary reactions. As the base for such purposes, there may be used organic bases such as triethylamine, N-methylmorpholine, pyridine, 1,8-diazabicyclo[5,4,0]-7-undecene, 1,5-azabicyclo[4,3,0]non-5-ene, etc. and inorganic bases such as potassium carbonate, potassium hydrogen carbonate, sodium carbonate, sodium hydrogen carbonate, lithium carbonate, lithium hydrogen carbonate and so on. Where an alkali metal salt of reagent [III] or [V] is used, the sodium salt, lithium salt, potassium salt, etc. can be employed. The compound [IV] or [VI] may be isolated and purified by conventional procedures such as concentration, concentration under reduced pressure, pH adjustment, redistribution, solvent extraction, distillation, crystallization, recrystallization, chromatography, etc. and subjected to the next reaction. Alternatively the reaction mixture containing [IV] or [VI] may be such be directly used as the starting reactant for the next reaction.

The starting compound of general formula [II] for Process 1) can be synthesized by the procedures described in Chem. Ber. 100, 591 (1967), Acta. Chem. Scand. 22, 1107 (1968), Synthesis 1986, 967, Chem. Ber. 95, 2861 (1962), Tetraheron 30, 2413 (1974), Synthesis 1984, 797 and other literature or by procedures analogous thereto. The compound [III] can be synthesized by the procedures described in Organic Functional Group Preparations, Academic Press, Vol 1, Chapter 13 (1968) and Vol 3, Chapter 10 (1972) and other literature or by procedures analogous thereto, and the compound [V] can be synthesized by the procedures described in Survey of Organic Syntheses, Wiley-Interscience (1970), Chapter 8 and other literature or by procedures analogous thereto.

The aforementioned Process 2) comprises (1) reacting an amino compound of general formula [III] (Y=H) or an alkali metal salt (e.g. Na or K salt) with an isothiocyanic ester of general formula [VII] to give a thiourea of general formula [VIII], then reacting said thiourea [VIII] with the compound of the formula : $R^5I$ (e.g. methyl iodide, etc.) to give an isothiourea of general formula [IX], and reacting [IX] with an active methylene compound of general formula [X], (2) reacting an-amino compound of general formula [III] (Y=H) or an alkali metal salt thereof with an isothiocyanic ester [VII'], then reacting the resulting thiourea [VIII'] with the compound of the formula: $R^5I$ (e.g. methyl iodide, etc.) to give an isothiourea [IX'] and reacting [IX'] with an active methylene compound [X], or (3) reacting an amino compound of general formula [V](Y=H) or an alkali metal salt thereof with an isothiocyanic acid ester [VII"], reacting the resulting thiourea [VIII"] with the compound of the formula: $R^5I$ (e.g. methyl iodide, etc.), and reacting the resulting isothiourea [IX"] with an active methylene compound, to thereby give the desired compound [I].

Referring to Process 2), the reactions $[III]_{Y=H}$→[VIII], $[III]_{Y=H}$→[VIII'] and $[V]_{Y=H}$→[VIII"] and the reactions [VIII]→[IX], [VIII']→[IX'] and [VIII"]→[IX"] can each be conducted by the known procedures described in the literature or by procedures analogous thereto. As said literature, there may be mentioned Chemical Society of Japan (ed.): Shin Jikken Kagaku Koza (New Series of Experimental Chemistry), Vo. 14, III, Maruzen (1978), Chapters 7 and 21; Organic Functional Group Preparations, Vol. 2, Academic Press (1971), Chapters 6 and 7, ditto The Second Edition (1986), and so on.

Each of the reactions $[III]_{Y=H}$→[VIII], $[III]_{Y=Y}$→[VIII'], and $[V]_{Y=H}$→[VIII"] can be conducted in an appropriate solvent. There is no limitation on such a solvent provided that it does not interact with the reactant or the reagent but it is preferable to select a solvent capable of dissolving both the reactant and reagent. As examples of such solvent, there may be mentioned aromatic hydrocarbons such as benzene, toluene, xylene, etc.; aliphatic hydrocarbons such as pentane, hexane, heptane, petroleum ether, ligroine, petroleum benzene, etc.; ethers such as diethyl ether, dipropyl ether, dibutyl ether, tetrahydrofuran, dioxane, etc.; acid amides such as dimethylformamide, dimethylacetamide, etc.; sulfoxides such as dimethyl sulfoxide etc.; sulfones such as sulfolane etc.; phosphoramides such as hexamethylphosphoramide etc.; and halogenated hydrocarbons such as chloroform, dichloromethane, carbon tetrachloride, 1,2-dichloroethane, etc. as well as various mixtures thereof. The reaction temperature is about −30° to 200° C. and preferably 0 to 150° C. The reaction time varies with such conditions as reaction temperature, reactant, reagent, reaction system concentration and solvent, but generally in the range of 1 minute to 24 hours.

The proportions of compounds [VII], [VII'] and [VII"] required for the respective reactions may range from 0.5 to 2 molar equivalents, preferably 0.8 to 1.2 molar equivalents, relative to [III $]_{Y=H}$, [III$]_{Y=H}$ and [V$]_{Y=H}$. The compounds [VIII], [VIII'] and [VIII"] thus obtained can each be subjected to the next reaction either without isolation or after isolation from the reaction mixture by the known procedure.

Each of the reactions [VIII]→[IX], [VIII']→[IX'] and [VIII"]→[IX"] may also be conducted in a solvent. In addition to the solvents mentioned for the reactions [III]$_{Y=H}$→[VIII], [III]$_{Y=H}$→[VIII'] and [V]$_{Y=H}$→[VIII"], such other solvents as alcohols, e.g. methanol, ethanol, propanol, butanol, etc.; ketones, e.g. acetone, methyl ethyl ketone, etc.; and esters, e.g. methyl acetate, ethyl acetate, butyl acetate, methyl formate, ethyl formate, ethyl propionate, etc. can also be employed. The reagent methyl iodide may be utilized as the solvent. For the purpose of promoting the reaction and minimizing the formation of byproducts, a base may be permitted to be present in the reaction system or permitted to act on the reaction system before or after the reaction and there are cases in which such practice contributes to improved results. As the base that can be used for the above purpose, there may be mentioned sodium hydride, sodium metal, alcoholates such as sodium ethoxide, sodium methoxide, potassium tert-butoxide, etc., organic bases such as triethylamine, diisopropylethylamine, pyridine, N,N-dimethylaniline, etc. and inorganic bases such as potassium carbonate and so on. The proportion of the base is preferably 0.8 to 1.2 molar equivalents relative to [VIII], [VIII'] or [VIII"]. In the absence of a base in the reaction system, [IX], [IX'] or [IX"] is formed as the hydroiodide so that this hydroiodide must be neutralized to obtain [IX], [IX'] or [IX"]. The base for this purpose is preferably a water-soluble inorganic base such as sodium carbonate, sodium hydrogen carbonate, potassium hydrogen carbonate, potassium carbonate, sodium hydroxide, potassium hydroxide and so on. The reaction temperature is 0 to 100° C. and preferably 20 to 80° C. The reaction time is generally 0.1 to 24 hours. The proportion of methyl iodide required for the reaction is not less than 1 molar equivalent relative to [VIII], [VIII'] or [VIII"] and may be used in a larger amount as the solvent. The [IX], [IX'] or [IX"] thus produced may be isolated by the conventional procedure before submission to the next reaction or the reaction product mixture may be directly used as the starting material in the next reaction.

Each of the reactions [IX]→[I-1], [IX']→[I-2] and [IX"]→[I-3] can be conducted in accordance with the procedures described in Tetrahedron 37, 1453 (1981) Indian Journal of Chemistry 15B, 297 (1977) and other literature. The reaction may be conducted using the active methylene compound [X] in excess as a solvent or may be carried out in a different solvent. As the solvent just mentioned above, there may be used aromatic hydrocarbons such as benzene, toluene, xylene, etc., aprotic polar solvents such as dimethylformamide, dimethylacetamide, dimethyl sulfoxide, sulfolane, hexamethylphosphoramide, etc., and ethers such as tetrahydrofuran, dioxane and so on. Particularly where an aprotic polar solvent is used and the reaction is conducted under reduced pressure with the byproduct methylmercaptan being dispelled out of the reaction system, the formation of byproducts can be suppressed and the reaction yield improved. The reaction may also be conducted in the presence of a catalyst. As such catalyst, there may be employed zinc chloride, zinc bromide, zinc iodide, cupric chloride and so on. The reaction temperature is 30 to 200° C., preferably 50–150° C. The reaction time is generally 0.1 to 48 hours. The proportion of active methylene compound [X] necessary for the reaction is 1 to 5 molar equivalents relative to [IX], [IX'] or [IX"]. Where [X] is a low-boiling compound, it can be used in a solvent amount.

The starting compounds [VII], [VII'] and [VII"] can be synthesized by the procedures described in Organic Functional Group Preparations, Vol. 1, Academic Press (1968), Chapter 12 and other literature or by procedures analogous thereto, and the compound [X] can be synthesized by procedures described in Formation of C—C Bonds, Vol. 1, Georg Thieme Publishers, Stuttgart (1973) and other literature.

The aforementioned Process 3) comprises reacting a compound [XI] or [XII] with an amino compound of general formula [III] or a salt thereof (e.g. the salt of an alkali metal such as Na or K) and reacting the resulting product further with an amino compound of general formula [V] or a salt (alkali metal salt) thereof or, alternatively, reacting a compound [XI] or [XII] with an amino compound of general formula [V] or a salt thereof and then reacting the resulting product with an amino compound of general formula [III] or a salt thereof to give the desired compound [I].

The reactions in Process 3) can be conducted in the same manner as those in Process 1) and the reaction conditions described for Process 1) can be utilized. However, since compounds [XI] and [XII] are generally more reactive than compound [II], the reactions are preferably conducted under somewhat milder conditions as compared with Process 1).

The compounds [XI] and [XII] can be prepared by procedures described in Chemical Abstracts 44, 1011f, Journal of Organic Chemistry 25, 1312 (1960) and other literature or by procedures analogous thereto.

The aforementioned Process 4) comprises reacting an acid amide of general formula [XIII] or an acid amide of general formula [XV] with a halogenating agent to give a halide of general formula [XIV] or [XVI] and reacting the halide with an amino compound of general formula [V] or a salt thereof or an amino compound of general formula [III] or a salt thereof to give the desired compound [I].

The reaction of [XIII]→[XIV] and that of [XV]→[XVI] are preferably conducted in a solvent. As such solvent, there may be mentioned halogenated hydrocarbons such as dichloromethane, chloroform, carbon tetrachloride, 1,2-dichloroethane, etc., ethers such as diethyl ether, tetrahydrofuran, dioxane, etc., nitriles such as acetonitrile, propionitrile, etc. and so on. This reaction is preferably carried out under anhydrous conditions. The halogenating agent may for example be phosphorus pentachloride, hosphorus oxychloride, phosphorus trichloride, thionyl chloride, oxalyl chloride or the like. The proportion of the halogenating agent is 1 to 10 molar equivalents, preferably 1 to 5 molar equivalents, relative to [XIII] or [XV]. Preferably a base is permitted to be present in the reaction system in order to trap the byproduct hydrogen chloride, and as such base, there may be used various organic bases such as pyridine, triethylamine, diisopropylethylamine, N-methylmorpholine, N,N-dimethylaniline, N,N-diethylamine and so on. The reaction temperature is $-80°$ to $100°$ C. and preferably $-50°$ to $50°$ C. The reaction time is generally 0.1 to 24 hours, depending on the reactant, base, solvent, reaction concentration and reaction temperature. The products [XIV] and [XVI] can be isolated and purified by the aforementioned known procedures before submission to the next reaction or the reaction product mixture may be directly used in the next reaction.

The reaction of [XIV]→[I] and that of [XVI]→[I] can each be conducted in a solvent similar to those mentioned for the reactions of [XIII]→[XIV] and [XV]→[XVI], preferably under anhydrous conditions. The proportion of [V] or a salt thereof and that of [III] or a salt thereof are 1 to 10 molar equivalents, preferably 1 to 5 molar equivalents, relative to [XIV] and [XVI], respectively. For the purpose of trapping the byproduct hydrogen chloride, [V] or a salt thereof or [III] or a salt thereof can be used in excess but for economy, a different base is preferably permitted to be present. A such base, there may be used any of the bases mentioned for the reactions of [XIII]→[XIV] and [XV]→[XVI]. The reaction temperature is $-80°$ C. to $100°$ C. and preferably $-50°$ C. to $50°$ C. The reaction time is generally 0.1 to 24 hours. The starting compounds [XIII] and [XV] can be synthesized by the procedures described in Formation of C—C bonds, Vol. 1, Georg Thieme Publishers, Stuttgart (1973) and Chemical Society of Japan(ed.): 'Shin Jikken Kagaku Koza' (New Series of Experimental Chemistry), Vol. 14,II, Maruzen (1977), Chapters 5 and 7 and other literature or by procedures analogous thereto.

The aforementioned Process 5) comprises reacting a compound of general formula [XVII] with a halide of general formula [XVIII] to give the desired compound [I].

The reaction according to Process 5) is preferably conducted in an appropriate solvent. As such solvent, there may be employed acid amides such as dimethylformamide, dimethylacetamide, etc., sulfoxides such as dimethyl sulfoxide etc., sulfones such as sulfolane etc., phosphoramides such as hexamethylphosphoramide etc., ethers such as tetrahydrofuran, dioxane, 1,2-dimethoxyethane, diethylene glycol dimethyl ether, etc., and so on. Mixtures of such solvents may likewise be employed. This reaction is preferably conducted in the presence of a base. As such base, there may be mentioned sodium hydride, potassium hydride, lithium hydride, calcium hydride, n-butyllithium, lithium diisopropylamide, sodium amide and so on. It is preferable that the compound [XVII] be converted to the salt of said base before it is subjected to the reaction. The proportion of the base is preferably 1 to 1.5 molar equivalents relative to [XVII]. This reaction is preferably conducted under anhydrous conditions and may be carried out in an atmosphere of nitrogen gas or argon gas. The proportion of [XVIII] is 1 to 2 molar equivalents, preferably 1 to 1.5 molar equivalents, relative to [XVII]. The reaction temperature is $-70°$ C. to $150°$ C. and preferably $-50°$ C. to $100°$ C. The reaction time is generally 0.1 to 48 hours.

The compound [XVII] can be easily prepared, for example by using a compound of general formula $R^2 N_2$ wherein $R^2$ has the meaning defined hereinbefore, instead of compound [III] in said Processes 1 through 4). The compound [XVIII] can be synthesized by the process described in Organic Functional Group Preparations, Vol. 1, Academic Press (1968), Chapter 6 and other literature or by procedures analogous thereto.

The aforementioned Process 6) comprises subjecting a compound of general formula [XIX], which falls within the category of compound [I], to hydrolysis reaction and, then, to decarboxylation reaction to give a compound of general formula [I-4] which falls within the category of compound [I].

The above hydrolysis reaction can be conducted under the conditions of hydrolysis of esters which are known in the art.

Thus, in a solvent (inclusive of a solvent mixture) such as water, alcohols (e.g. methanol, ethanol, propanol, butanol, diethylene glycol, 2-methoxyethanol, etc.), ketones (e.g. acetone etc.), ethers (e.g. tetrahydroojuran, dioxane, dimethoxyethane, etc.), amides (e.g. dimethylformamide, dimethylacetamide, hexamethylphosphoramide, etc.), sulfoxides (e.g. dimethyl sulfoxide etc.), sulfones (e.g. sulfolane etc.) and carboxylic acids (e.g. formic acid, acetic acid, etc.), the hydrolysis reaction can be conducted using an acid (for example, mineral acids such as hydrochloric acid, hydrobromic acid, sulfuric acid, etc., organic acids such as p-toluenesulfonic acid etc., strongly acidic ion-exchange resins, and so on) or a base (for example, sodium hydroxide, potassium hydroxide, potassism carbonate, sodium hydrogen carbonate, barium hydroxide, calcium hydroxide, sodium methoxide, ammonia and so on), although the use of a base is preferred. The proportion of the base is about 1 to 10 molar equivalents, preferably about 1.2 to 4 molar equivalents, relative to [XIX]. The reaction temperature is about $-20°$ C. to $200°$ C., preferably about $-5°$ C. to $120°$ C., and the reaction time is about 0.1 to 48 hours, preferably about 0.1 to 24 hours.

The decarboxylation reaction proceeds simultaneously with said hydrolysis reaction in many cases and usually no special procedure is required. If necessary, this reaction may he carried out by heating in the hydrolysis solvent. The reaction temperature is generally about 0 to $200°$ C., preferably 30 to $150°$ C., and the reaction time is 0.1 to 48 hours and preferably 0.1 to 24 hours.

The aforementioned Process 7) comprises subjecting a compound of general formula [I-5] or a compound of general formula [I-6] to alkylation, acylation, alkoxycarbonylation, sulfonylation or phosphorylation to give a compound [I].

For alkylation, the amino group in [I-5] or [1-6] is alkylated with an alkylating agent such as an alkyl chloride, alkyl bromide, alkyl iodide, dialkyl sulfate or the like. The proportion of the alkylating agent is about 1 to 3 equivalents relative to the starting compound in many instances. This alkylation reaction may be conducted under the same conditions as those described for Process 5).

The acylation, sulfonylation, phosphorylation and alkoxycarbonylation reaction can each be conducted by procedures known per se or by procedures analogous thereto.

The acylating agent for said acylation reaction may for example be an acyl halide or acid anhydride containing a group of $R^1$ or $R^2$. The sulfonylating agent for said sulfonylation reaction may for example be a sulfonyl halide or sulofonic anhydride containing a group of $R^1$ or $R^2$. The alkoxycarbonylating agent for said alkoxycarbonylation reaction may for example an alkoxycarbonyl halide or carbonate containing a group of $R^1$ or $R^2$. The preferred halogens in the above-mentioned halide reagents are bromine and chlorine. The proportion of each such reagent is at least one molar equivalent, preferably about 1 to 5 molar equivalents, relative to the starting compound. Where an acid anhydride is used as the acylating agent in the above acylation reaction, it can be employed in excess. These reactions are carried out in a solvent capable of dissolving the compound [I-5] or [I-6] and the respective reagents and as preferred examples of such solvent, there may be mentioned dichloromethane, chloroform, dichloroethane, tetrahydrofuran, dioxane, N,N-dimethylformamide, N,N-dimethylacetamide, dimethyl sulofoxide, hexamethylphosphorotriamide, pyridine and so on. The reaction temperature is about −50° C. to 150° C. and the reaction time is about 0.1 to 48 hours. The reaction may be hastened and the secondary reactions suppressed to improve the yield when the reaction is conducted in the concomitant presence of an amine such as triethylamine, dimethylaminopyridine, pyridine, N,N-dimethylaniline, N,N-diethylaniline, etc., sodium hydride, potassium hydride, sodium amide, n-butyllithium, lithium diisopropylamide or the like.

The object compound (I) or salt thereof thus produced can be isolated and purified by conventional procedures such as concentration, concentration under reduced pressure, distillation, fractional distillation, pH adjustment, redistribution, solvent extraction, crystallization, recrystallization, chromatography and so on.

Where the compound [I] is obtained as the free compound, it can be converted to a agrochemically useful salt and where a salt is obtained, it can be converted to the free compound [I], using the conventional procedure in either case. Where the compound [I] contains acidic groups such as carboxyl, sulfo and/or phosphono groups in its positions $X^1$, $X^2$, $R^1$, $R^2$ and/or A, it may form a salt with a base. As the base used for this purpose, there may be mentioned inorganic bases such as sodium, potassium, lithium, calcium, magnesium, ammonia, etc. and organic bases such as pyridine, collidine, triethylamine, triethanolamine and so on. Where the compound [I] contains basic groups such as amino, substituted amino and/or other groups in its positions $X^1$, $X^2$, $R^1$, $R^2$ and/or A, it can form an acid addition salt. As examples of such acid addition salts, there may be mentioned hydrochloride, hydrobromide, hydroiodide, nitrate, sulfate, phosphate, acetate, benzoate, maleate, fumarate, succinate, tartarate, citrate, oxalate, glyoxalate, aspartate, methanesulfonate, methanedisulfonate, 1,2-ethanedisulfonate, benzenesulfonate and so on.

The compound [I] may form an inner salt, which also falls within the scope of the invention.

The compound [I] and its stereoisomer and tautomer (for example, where the compound [I] is a compound of the formula

[I′]

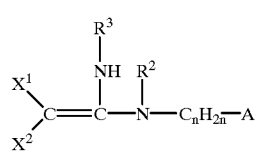

wherein the symbols have the meanings defined hereinbefore, its tautomer of the formula

[I″]

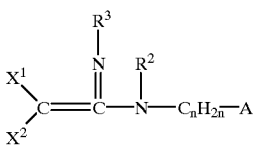

wherein the symbols have the meanings defined hereinbefore, also falls into the category of compound [I]) can be used, either independently or in the form of a mixture, as an insecticidal/miti(acari)cidal agent.

The compound [I] and its salt according to the invention are effective in the control of household pests and animal or plant parasitizing insects and mites, and exhibit strong pesticidal effects as a contact poison when applied directly to the host animals and plants. The most salient feature of the compound, however, is that it displays potent pesticidal effects even after it has been absorbed onto plants via the root, leaf, stem or the like and come into contact with the pests as the pests suck or gnaw on the plants. This property is advantageous in the control of sucking/biting insets and ticks. Furthermore, the compound of the invention is of low toxicity to plants and fish, thus having safe and useful characteristics as an agricultural pesticide.

The compound [I] and its salts and compositions containing the same are particularly effective in the control of the following kinds of pests: pests of the order Hemiptera such as *Eurydema rugosum*, *Scotinophara lurida*, *Riptortus clavatus*, *Stephanitis nashi*, *Laodelophax striatellus*, *Nilaparvata lugeops*, *Nephotettix cincticeis*, *Unaspis yanonensis*, *Aophis glycines*, *Litaophis erysimi*, *Brevicoryne brassicae*, *Aphis qossvoii*, *Sogattela furcifera*, *Nezara viroldula*, *Trialeurodes vaporariorum*, *Myzus persicae*, *Pseudococcus comstocki*, *Aphis promi*, Nezara spp., *Cimex lectularius*, Psylla spp., etc.; pests of the order Lepidoptera such as *Spodoptera litura*, *Plutella xylostella*, *Pieris rapae crucivora*, *Chilo suoppressalis*, *Plusia nigrisigna*, *Halicoverpa assulta*, *Leucania separata*, *Mamestra brassicae*, *Adoxophyes orana*, *Notarcha derogata*, *Cnaphalocrocis medinalis*, *Phthorimaea operculella*, etc.; pests of the order Cleoptera such as *Epilachna vigintioctopunctata*, *Aulacophora femoralis*, *Phyllotreta striotata*, *Oulema oryzae*, *Echinocnemus sauameus*, etc.; pests of the order DiDtera such as *Musca domestica*, *Culex opidiens pallens*, *Tabanus trigonus*, *Hylemyia antigua*, *Hylemyia platura* etc.; pests of the order Orthoptera such as *Locusta migratoria*, *Gryllotalpa africana*, etc., cockroaches such as *Blattella germanica*, *Periplaneta fuliocinosa*, etc.; spider mites such as *Tetranychus urticae*, *Panonychus citri*, *Tetranychus kanzawai*, *Tetranychus cinnabarinus*, *Panonychus ulmi*, *Aculops pelekassi*, etc., and nematodes such as *Aphelenchoides besseyi* and so on.

For application of the compound [I] or salt of the invention as an insectide/miti(acari)cide, it can be formulated into any possible and desired application form for agrochemicals. Thus, by dissolving or dispersing one or more species of compound [I] and salt thereof in an appropriate liquid carrier or vehicle or admixing them with or causing them adsorbed on an appropriate solid carrier, an emulsifiable concentrate, oil preparation, wettable powders, dusts, granules, tablets, aerosol, ointment or the like can be manufactured. If necessary, such compositions may be further supplemented with emulsifiers, suspending agents, spreaderstickers, penetrating agents, wetting agents, thickeners, stabilizers and so on, and any of such preparations can be manufactured by the per se known procedures.

The concentration of the active ingredient (compound [I] or salt thereof) in such an insecticidal/miti(acari)cidal composition of the invention depends on the intended application. Generally speaking, the proper concentration is about 10 to 90 weight percent for emulsifiable concentrate and wettable powders, about 0.1 to 10 weight percent for oils and dusts and about 1 to 20 weight percent for granules, for instance. However, the concentration may be adjusted according to the intended application. In the case of an emulsifiable concentrate or a wettable powder, it is diluted with water or the like to a suitable concentration (for example, 100 to 100,000-fold dilution) before spraying.

The liquid carrier (solvent) includes, among others, water, alcohols (e.g. methyl alcohol, ethyl alcohol, n-propyl alcohol, isopropyl alcohol, ethylene glycol, etc.), ketones (e.g. acetone, methyl ethyl ketone, etc.), ethers (e.g. dioxane, tetrahydrofuran, ethylene glycol monomethyl ether, diethylene glycol monomethyl ether, propylene glycol monomethyl ether, etc.), aliphatic hydrocarbons (e.g. kerosin, kerosene, fuel oil, machine oil, etc.), aromatic hydrocarbons (e.g. benzene, toluene, xyiene, solvent naphtha, methylnaphthalene, etc.), halogenated hydrocarbons (e.g. methylene chloride, chloroform, carbon tetrachloride, etc.), acid amides (e.g. dimethylformamide, dimethylacetamide, etc.), esters (e.g. ethyl acetate, butyl acetate, fatty acid glycerin esters, etc.), nitriles (e.g. acetonitrile, propionitrile, etc.) and so on. One of these solvents or a mixture of two or more of them can be used as the carrier.

The solid carrier (diluent-volume builder) includes, among others, vegetable powders (e.g. soybean flour, tobacco flour, wheat flour, sawdust, etc.), mineral powders (e.g. clays such as kaolin, bentonite, acid clay, etc., talcs such as talc, pyrophillite, etc. and silicates such as diatomaceous earth, mica powder, etc.), alumina, sulfur powder, activated carbon and so on. These powders can be used singly or as a mixture.

The ointment base that can be employed include, among others, any or a mixture of polyethylene glycol, pectin, higher fatty acid polyhydric alcohol esters such as monostearic acid glycerin ester etc., cellulose derivatives such as methylcellulose etc., sodium alginate, bentonite, higher alcohols, polyhydric alcohols such as glycerin, vaseline, white petrolatum, liquid paraffin, lard, vegetable oils, lanolin, anhydrous lanolin, hydrogenated oils, resins, etc., or mixtures thereof with the any of the following surfactants.

Surfactants which can be optionally used as said emulsifier, spreader/sticker, penetrating agent, dispersing agent, etc. include soaps and nonionic or anionic surfactants such as polyoxyethylene alkyl aryl ethers (e.g. Noigen, E. A. 142®, manufactured by Daiichi Kogyo Seiyaku Co., Ltd., JAPAN; Nonal®, Toho Chemical, JAPAN), alkylsulfates (e.g. Emal 10®, Emal 40®, manufactured by Kao Corporation, JAPAN), alkylsulfonates (e.g. Neogen®, Neogen T®, manufactured by Daiichi Kogyo Seiyaku Co., Ltd.; Neopellex®, manufactured by Kao Corporation), polyethylene glycol ethers (e.g. Nonipol 85®, Nonipol 100®, Nonipol 160®, manufactured by Sanyo Chemical Industries, Ltd., JAPAN) and polyhydric alcohol esters (e.g. Tween 20®, Tween 80®, manufactured by Kao Corporation).

The compound of the invention can be used in combination with other insecticides (pyrethroid insecticides, organophosphorus insecticides, carbamate insecticides, natural insecticides, etc.), miticides (acaricides), nematocides, herbicides, plant hormones, plant growth regulators, fungicides (copper fungicides, organochlorine fungicides, organosulfur fungicides, phenolic fungicides, etc.), synergists, attractants, repellents, pigments, fertilizers and so on.

The resulting insecticide/miticide according to the invention is of low toxicity and safe and is an excellent agrochemical. The insecticidal/miticidal agent of the invention can be used in the same manner as the conventional insecticides and miticides and produces effects surpassing those of the latter. For example, the insecticidal/miticidal agent of this invention can be applied for control of pests by such procedures as nursery bed treatment, stem/foliage spray or dusting, direct application to pests, paddy water treatment, soil treatment and so on. The dosage can be selected from a broad range according to the timing, site and method of application. Generally speaking, the preferred dosage of the active ingredient (compound [I] or a salt thereof) per hectare is 0.3 g to 3,000 g and, for still better revolts, 50 g to 1,000 g. Where the insecticidal/miticidal agent of the invention is provided as a wettable powder, it can be used as diluted so that the final concentration of the active ingredient will be in the range of 0.1 to 1,000 ppm, preferably 10 to 500 ppm.

The compound [I] of the invention has excellent insecticidal/miticidal activity which is well demonstrated by the following test examples.

Test Example 1

Effect against brown planthoppers (*Nilaparvata lugens*)

An emulsifiable concentrate of the compound of the invention, prepared in the same manner as Example 112 below, was diluted with water to a concentration of 500 ppm and sprayed over the stems and leaves of rice seedlings in the 2-leaf stage at the rate of 10 ml per paper pot. Water was put in test tubes and the treated rice seedlings were placed therein. Then, 10 brown planthopper larvae were released in each tube, which was then capped with an aluminum cap. The test tubes were maintained in an incubator at 25° C. and the dead insects were counted 7 days after release. The % mortality was calculated using the following formula.

$$\text{Mortality } (\%) = \frac{\text{Number of dead insects}}{\text{Number of insects released}} \times 100$$

The results are shown in Table 1.

TABLE 1

| Effect against brown planthoppers | |
|---|---|
| Compound of the invention (Compound No.) | % Mortality after 7 days |
| 3 | 100 |
| 4 | 100 |
| 7 | 100 |
| 12 | 100 |
| 14 | 100 |
| 17 | 100 |
| 18 | 100 |
| 19 | 100 |
| 20 | 100 |
| 24 | 100 |
| 25 | 100 |
| 26 | 100 |
| 28 | 100 |
| 29 | 100 |
| 31 | 100 |
| 32 | 100 |
| 33 | 100 |
| 34 | 100 |
| 35 | 100 |
| 37 | 100 |
| 38 | 100 |
| 40 | 100 |

TABLE 1-continued

Effect against brown planthoppers

| Compound of the invention (Compound No.) | % Mortality after 7 days |
|---|---|
| 41 | 100 |
| 42 | 100 |
| 43 | 100 |
| 44 | 100 |
| 45 | 100 |
| 46 | 100 |
| 47 | 100 |
| 49 | 100 |
| 50 | 100 |
| 51 | 100 |
| 52 | 100 |
| 55 | 100 |
| 56 | 100 |
| 57 | 100 |
| 58 | 100 |
| 59 | 100 |
| 60 | 100 |
| 61 | 100 |
| 62 | 100 |
| 64 | 100 |
| 65 | 100 |
| 67 | 100 |
| 68 | 100 |
| 70 | 100 |
| 71 | 100 |
| 72 | 100 |
| 73 | 100 |
| 75 | 100 |
| 76 | 100 |
| 77 | 100 |
| 78 | 100 |
| 79 | 100 |
| 80 | 100 |
| 84 | 100 |
| 85 | 100 |
| 86 | 100 |
| 88 | 100 |
| 89 | 100 |
| 90 | 100 |
| 91 | 100 |
| 92 | 100 |
| 93 | 100 |
| 95 | 100 |
| 96 | 100 |
| 97 | 100 |
| 98 | 100 |
| 99 | 100 |
| 100 | 100 |
| 101 | 100 |
| 102 | 100 |
| 103 | 100 |
| 104 | 100 |
| 105 | 100 |
| 106 | 100 |
| 107 | 100 |
| 108 | 100 |
| 109 | 100 |
| 110 | 100 |
| 111 | 100 |
| 112 | 100 |
| 113 | 100 |
| mixture (7:3) of 114 and 115 | 100 |
| 116 | 100 |
| 117 | 100 |
| 118 | 100 |
| mixture (90:10) of 119 and 120 | 100 |
| mixture (40:60) of 119 and 120 | 100 |
| 121 | 100 |
| 122 | 100 |
| mixture (70:30) of 123 and 124 | 100 |
| 124 | 100 |
| 125 | 100 |
| 126 | 100 |
| 127 | 100 |
| 128 | 100 |
| 129 | 100 |
| 130 | 100 |
| 131 | 100 |

It is apparent from Table 1 that the compound [I] of the invention has excellent pesticidal activity against brown planthoppers.

The following reference and working examples are further illustrative of the invention but should by no means be construed as limiting the scope of the invention.

In the procedures of column chromatography described in the reference and working examples, elution was carried out under monitoring by thin layer chromatography (TLC). For TLC observation, Merck Kieselgel 60 $F_{254}$ (Art. 5715) was used as the TLC plate, the column chromatographic eluent as the developing solvent, and the UV detector as the means of detection. As the silica gel for column Dacking, Merck Kieselgel 60 (70–230 mesh, Art. 7734) was used. The NMR data represent $^1$H-NMR spectra determined using tetramethylsilane as either an internal or an external standard and, unless otherwise indicated, a Varian EM390 (90 MHz) spectrometer. The NMR data carrying the indication of 400 MHz were generated using a JEOL GX-400 (400 MHz) spectrometer. All the δ data are in ppm. Where a solvent mixture was used as the developer or eluent, the ratio of respective solvents is given in parentheses.

The abbreviations used in the reference and working examples have the following meanings.

Me: methyl; nPr: n-propyl, iPr: isopropyl, Et: ethyl, Ac: acetyl, s: singlet, br: broad, d: doublet, t: triplet, q: quartet, m: multiplet, dd: doublet doublet, tt: triplet triplet, dt: doublet triplet, td: triplet doublet, ddd: doublet doublet doublet, S+S: two singlets, J: coupling constant, Hz: hertz, $CDCl_3$: chloroform-d, $D_2O$: deuterium oxide, DMSO-$d_6$: dimethyl-$d_6$ sulfoxide, %: weight %, m.p.: melting point.

REFERENCE EXAMPLE 1

N-Methyl-N-3-pyridylmethylamine

To 25 ml of a 20% aqueous solution of NAOH stirred under cooling with ice-water, a 40% aqueous solution of methylamine (13.6 g, 0.175 mole) was added dropwise over 5 minutes, followed by further dropwise addition of an aqueous solution (10 ml) of 8.2 g (0.05 mole) of 3-pyridylmethyl chloride hydrochloride over 10 minutes. The mixture was further stirred at room temperature for 2 hours and, then, extracted with $CH_2Cl_2$ (100 ml×3). The extract was dried over $MgSO_4$ and distilled to remove the solvent. The residue was subjected to vacuum distillation to give 2.6 g of the title compound as a yellow oil.

b.p.: 66° C./2 mmHg

NMR ($CDCl_3$) δ: 1.48 (s, NH), 2.45 (s, NMe), 3.76 (s, $CH_2N$)

REFERENCE EXAMPLE 2

N-(6-Chloro-3-pyridylmethyl)phthalimide

In 20 ml of EtOH, 9.4 g (6.4×10$^{-2}$mole) of phthalimide and 4.2 g of KOH were stirred for 30 minutes, followed by addition of 100 ml of DMF (dimethylformamide) and 5.2 g (2.5×10$^{-2}$ mole) of 6-chloro-3-pyridylmethyl chloride. The mixture was stirred at 60° C. for 1 hour. The EtOH and DMF were distilled off under reduced pressure and the residue was chromatographed on a silica gel column and eluted with CH$_2$Cl$_2$. The above procedure gave 6.7 g of the title compound as colorless needles.

m.p.: 142–143° C.

NMR (CDCl$_3$) δ: 4.85 (s, 2H), 7.28 (d, J=8.9 Hz, 1H), 7.6–8.0 (m, 5 H), 8.51 (d, J=2.8 Hz, 1H)

REFERENCE EXAMPLE 3

6-Chloro-3-pyridylmethylamine

Hydrazine hydrate (1.7 ml) was added to a refluxing solution of 6.5 g (2.4×10$^{-2}$ mole) of N-(6-chloro-3-pyridylmethyl)phthalimide in 100 ml of EtOH, and the mixture was further refluxed for 1 hour. After addition of 20 ml of water, the ethanol was distilled off under reduced pressure. Concentrated hydrochloric acid (25 ml) was added to the residue and the mixture was refluxed for 1 hour. After cooling, the reaction mixture was neutralized with NaOH and the aqueous layer was saturated with NaCl and extracted with Et$_2$O. The extract was dried over Na$_2$SO$_4$ and the solvent was distilled off to give 2.4 g of the title compound as a yellow oil.

NMR (CDCl$_3$) δ: 1.4–2.0 (br, 2H), 3.89 (s, 2H), 7.27 (d, J=8.9 Hz, 1H), 7.67 (dd, J=8.9 & 2.7 Hz, 1H), 8.32 (d, J=2.7 Hz, 1H)

REFERENCE EXAMPLE 4

1-Methylthio-1-piperidino-2-nitroethylene

In 20 ml of EtOH was dissolved 1.7 g (0.01 mole) of 1,1-bis(methylthio)-2-nitroethylene under heating and 0.9 g (0.01 mole) of piperidine dissolved in 10 ml of EtOH was added dropwise in 3 portions at 30-minutes intervals under reflux. After 2 hours of reflux, the solvent was distilled off and the residue was chromatographed on a silica gel column and eluted with AcOEt-toluene (2:3). The above procedure yielded 0.8 g of the title compound as yellow prisms.

m.p.: 65–67° C.

NMR (CDCl$_3$) δ: 2.45 (s), 6.68 (s)

IR (Nujol): 1650, 1530, 1380 cm$^{-1}$

REFERENCE EXAMPLE 5

1,1-bis(Methylthio)-2-nitroethylene was reacted with various amines in the same manner as Reference Example 4 to give the following compounds.

(1) 1-Methylamino-1-methylthio-2-nitroethylene (yellow scales)

m.p.: 111–112° C.

NMR (CDCl$_3$) δ: 2.45 (s), 3.15 (d), 6.62 (s), 10.5 (br s)

IR (Nujol): 3200, 1575, 1345 cm$^{-1}$ (2) 1-(2,2-Dimethyl-1-hydrazino)-1-methylthio-2-nitroethylene (pale yellow prisms)

m.p.: 139–140° C.

NMR CDCl$_3$) δ: 2.26 (s), 2.65 (s), 6.40 (s), 10.46 (br s)

IR (Nujol): 3130, 1535, 1340 cm$^{-1}$

REFERENCE EXAMPLE 6

N-(6-Chloro-3-pyridylmethyl)-N-methylamine (1) In 30 ml of toluene, 0.8 g (5.7×10 moles) of 6-chloropyridine-3-aldehyde and 10 g of Na$_2$SO$_4$ were mixed and while the mixtures was stirred, a 40% aqueous solution of methylamine (1.4 g, 1.1×10$^{-2}$ mole) was added dropwise over 30 minutes, followed by addition of 10 g of MgSO$_4$. The mixture was allowed to stand at room temperature overnight, after which it was filtered. The filtrate was concentrated to give 0.6 g (yield 68%) of N-(6-chloro-3-pyridylmethylidene)methylamine as crystals.

NMR (CDCl$_3$) δ: 3.52 (d, 3H), 7.35 (d, J=8.8 Hz, 1H), 8.04 (dd, J=8.8 & 2.7 Hz, 1H), 8.2–8.4 (m, 1H), 8.59 (d, J=2.7 Hz, 1H)

(2) In 10 ml of MeOH was dissolved 0.6 g (3.8×10$^{-3}$ moles) of the N-(6-chloro-3-pyridylmethylidene)methylamine obtained in (1) and under stirring at 0° C., 0.07 g (1.9×10$^{-3}$ mole) of sodium borohydride was added in small portions. After 30 minutes, MeOH was distilled off and the residue was diluted with 5 ml of water and extracted with AcOEt (10 ml×3). The extract was dried over MgSO$_4$ and concentrated to give 0.43 g (yield 71%) of the title compound as a yellow oil.

NMR (CDCl$_3$) δ: 1.90 (s, 1H), 2.44 (s, 3H), 3.74 (s, 2H), 7.28 (d, J=8.2 Hz, 1H). 7.67 (dd, J=8.2 & 2.8 Hz, 1H), 8.31 (d, J=2.8 Hz, 1H)

REFERENCE EXAMPLE 7

Pyridine-3-aldehyde or quinoline-3-aldehyde was reacted with various amines or 1,1-dimethylhydrazine in the same manner as Reference Example 6 (1) to give the following compounds.

(1) N-(3-Pyridylmethylidene)ethylamine (pale yellow oil)

NMR (CDCl$_3$) δ: 1.30(t), 3.66(q), 8.31(s)

(2) N-(3-Pyridylmethylidene)-2-dimethoxyethylamine (yellow oil)

NMR (CDCl$_3$) δ: 3.43 (s), 3.83 (d), 4.71 (t), 8.35 (s)

(3) N-(3-Pyridylmethylidene)-2-methoxyethylamine (pale yellow oil)

NMR (CDCl$_3$) δ: 3.39 (s), 3.76 (m), 8.36 (s)

(4) N-(3-Quinolylmethylidene)methylamine (yellow oil)

NMR (CDCl$_3$) δ: 3.53 & 3.54 (each s, =NMe), 7.1–8.5 (m, 6H, quinoline-H$_6$), 9.28 & 9.30 (each s, CH=N)

IR (neat): 1690, 1645, 1615, 1490, 785, 750 cm$^{-1}$ (5) 1,1-Di-methyl-2-(3-pyridylmethylidene)hydrazine (colorless oil)

b.p.: 110° C./2 mmHg

NMR (CDCl$_3$) δ: 3.00 (s, NMe$_2$), 7.15 (s, CH=N)

IR (neat): 1580, 1550, 1465, 1415, 1040, 710 cm$^{-1}$ (6) N-(3-Pyridylmethylidene)-n-propylamine (pale yellow oil)

NMR (CDCl$_3$) δ: 0.95 (t), 1.75 (m), 3.62 (t), 7.33 (dd), 8.12 (dt), 8.31 (s, CH=N), 8.62 (dd), 8.86 (d)

(7) N-(3-Pyridylmethylidene)-n-butylamine (pale yellow oil)

NMR (CDCl$_3$) δ: 0.94 (t), 1.20–1.90 (m), 3.65 (t), 7.33 (dd), 8.12 (dt), 8.31 (s, CH=N), 8.62 (dd), 8.86 (d)

(8) N-(3-Pyridylmethylidene)benzylamine (pale yellow oil)

NMR (CDCl$_3$) δ: 4.84 (s, CH$_2$), 7.33 (s, C$_6$H$_5$), 7.33 (dd), 8.15 (dt), 8.40 (br s, CH=N), 8.65 (dd), 8.88 (d)

REFERENCE EXAMPLE 8

The compounds of Reference Example 7 (1)–(4) and (6)–(8) were respectively reacted in the same manner as Reference Example 6 (2) to give the following compounds.

(1) N-Ethyl-N-(3-pyridylmethyl)amine (pale yellow oil)

b.p.: 60° C./0.7 mmHg

NMR (CDCl$_3$) δ: 1.13 (t), 1.45 (br s), 3.70 (q), 3.82 (s)

(2) N-(2-Dimethoxyethyl)-N-(3-pyridylmethyl)amine (yellow oil)

NMR (CDCl$_3$) δ: 1.73 (br s), 2.75 (d), 3.36 (s), 3.82 (br s), 4.46 (t)

(3) N-(2-Methoxyethyl)-N-(3-pyridylmethyl)amine (colorless oil)
b.p.: 90° C./0.7 mmHg
NMR (CDCl$_3$) δ: 1.86 (br s), 2.82 (t), 3.36 (s), 3.53 (t), 3.83 (s)

(4) N-Methyl-N-(3-quinolylmethyl)amine (yellow oil)
NMR (CDCl$_3$) δ: 2.24 (s, NMe), 3.09 (br, NH), 3.86 (s, NCH$_2$), 7.3–8.2 (m, 5 H, quinoline-H$_5$), 8.83 (d, J=2 Hz, 1H, quinoline-H$_1$)

(5) N-(n-Propyl)-N-(3-pyridylmethyl)amine (yellow oil)
b.p.: 85° C./1.5 mmHg
NMR (CDCl$_3$) δ: 0.90 (t), 1.30–1.76 (m), 1.64 (br s, NH), 2.60 (t), 3.80 (s), 7.23 (dd), 7.67 (dt), 8.43–8.63 (m)

(6) N-(n-Butyl)-N-(3-pyridylmethyl)amine (pale yellow oil)
b.p.: 83° C./1 mmHg
NMR (CDCl$_3$) δ: 0.78–1.06 (r), 1.1–1.75 (m), 1.45 (br s, NH), 2.63 (t), 3.80 (s), 7.24 (dd), 7.69 (dt), 8.46–9.63 (m, 2H)

(7) N-Benzyl-N-(3-pyridylmethyl)amine (colorless oil)
b.p.: 125° C./0.5 mmHg
NMR (CDCl$_3$) δ: 1.83 (br s, NH), 3.77 (s, 4H), 7.26 (dd), 7.32 (br s, C$_6$H$_5$), 7.66 (dt), 8.43–8.60 (m, 2H)

REFERENCE EXAMPLE 9

1,1-Dimethyl-2-(3-pyridylmethyl)hydrazine

In 100 ml of dry ethyl ether was suspended 4.6 g of lithium aluminum hydride and with stirring in a nitrogen gas stream, a solution of 12.0 g of 1,1-dimethyl-2-(3-pyridylmethylidene)hydrazine in 50 ml is of dry ethyl ether was added dropwise. The mixture was refluxed for 5 hours and, then, cooled (5° C.) and with stirring, 5 ml of water, 5 ml of 20% aqueous sodium hydroxide and 15 ml of water were added dropwise in succession. The insoluble matter was filtered off, the filtrate was concentrated, and the residue was purified by silica gel column chromatography (eluent: chloroformethanol=10:1). The resulting oil was distilled under reduced pressure to give 2.5 g of the title compound as a yellow oil.
b.p: 100–115° C./1 mmHg
NMR (CDCl$_3$) δ: 2.47 (s, NMe$_2$), 2.81 (br s, NH), 3.93 (s, CH$_2$N)

REFERENCE EXAMPLE 10

2,6-Dichloro-3-pyridylmethylamine
(1) In 40 ml of DMF was suspended 3.9 g (0.021 mole) of potassium phthalimide followed by addition of 3.9 g (0.02 mole) of 2,6-dichloro-3-pyridylmethyl chloride and the mixture was stirred at 60–70° C. for 2 hours. The DMF was distilled off under reduced pressure and the residue was diluted with 50 ml of water and extracted with CHCl$_3$ (50 ml×3). The extract was dried over MgSO$_4$ and concentrated and the resulting precipitate was collected by filtration, washed with ether and dried to give 3.8 g of N-2,6-dichloro-3-pyridylmethyl)phthalimide as white prisms.
m.p.: 189–190° C.
NMR (CDCl$_3$) δ: 4.95 (s, 2H), 7.22 (d, J=8.5 Hz), 7.65 (d, J=8.5 Hz), 7.66–8.0 (m, 4H)

(2) In a mixture of 50 ml EtOH and 20 ml DMF was dissolved 3.1 g (0.01 mole) of N-(2,6-dichloro-3-pyridylmethyl)phthalimide under heating, followed by addition of 0.75 g (0.015 mole) of H$_2$NNH$_2$·H$_2$O under reflux. After 1 hour of refluxing, EtOH and DMF were distilled off. To the residue were added 10 ml of concentrated hydrochloric acid and 5 ml of water, and the mixture was refluxed for 30 minutes. The resulting crystals were filtered off and the filtrate was neutralized with NaHCO$_3$ and extracted with CH$_2$Cl$_2$ (30 ml×3). The extract was dried over MGSO$_4$ and the solvent was distilled off to give 1.45 g of the title compound as a yellow oil.
NMR (CDCl$_3$) δ: 1.55 (s, 2H), 3.96 (s, 2H), 7.27 (d, J=8.5 Hz), 7.82 (d, J=8.5 Hz)

REFERENCE EXAMPLE 11

N-(2,6-Dichloro-3-pyridylmethyl)-N-methylamine

In 50 ml of acetonitrile was dissolved 7.8 g (0.1 mole) of 40% aqueous methylamine and with stirring and ice-cooling, a solution of 3.9 g (0.02 mole) of 2,6-dichloro-3-pyridylmethyl chloride in 10 ml of acetonitrile was added dropwise over 5 minutes. After completion of the dropwise addition, the mixture was stirred at room temperature for 2 hours and, then, concentrated. The residue was extracted with ether (30 ml×3 ) and dried over MgSO$_4$. Finally, the solvent was distilled off to give 3.2 g of the title compound as a pale yellow oil.
NMR (CDCl$_3$) δ: 1.46 (s, NH), 2.46 (s, 3H), 3.82 (s, 2H), 7.26 (d, J=8.5 Hz), 7.75 (d, J=8.5 Hz)

REFERENCE EXAMPLE 12

1-[N-(2,6-Dichloro-3-pyridylmethyl)-N-methyl]amino-1-methylthio-2-nitroethylene

The reaction according to Reference Example 4 was repeated except that N-(2,6-dichloro-3-pyridylmethyl)-N-methylamine was used in lieu of piperidine. The procedure gave the title compound as yellow prisms.
m.p.: 111–112° C.
NMR (CDCl$_3$) δ: 2.46 (s, 3H), 3.12 (s, 3H), 4.84 (s, 2H), 6.79 (s, 1H), 7.35 (d, J=8.5 Hz), 7.66 (d, J=8.5 Hz)

REFERENCE EXAMPLE 13

1,1-bis(Methylthio)-2-nitroethylene was reacted with various amines in the same manner as Reference Example 4 to give the following compounds.

(1) 1-Dimethylamino-1-methylthio-2-nitroethylene (yellow oil)
NMR (CDCl$_3$) δ: 2.46 (s, 3H), 3.21 (s, 6 H), 6.69 (s, 1H)

(2) 1-(N-Ethyl-N-methyl)amino-1-methylthio-2-nitroethylene (yellow oil)
NMR (CDCl$_3$) δ: 1.27 (t, J=6.5 Hz, 3H), 2.48 (s, 3H), 3.13 (s, 3H), 3.64 (q, J=6.5 Hz, 2H), 6.73 (s, 1H)

(3) 1-(4-Chlorobenzyl)amino-1-methylthio-2-nitroethylene (pale yellow crystals)
m.p.: 121–123° C.
NMR (CDCl$_3$) δ: 2.43 (s, Me), 4.60 (d, J=6 Hz, CH$_2$), 6.59 (s, =CHNO$_2$), 7.23 & 7.36 (each d, J=9 Hz, each 2H, benzene-H$_4$), 10.71 (br, NH)

REFERENCE EXAMPLE 14

N-Methyl-N-[2-(3-pyridyl)ethyl]amine
(1) In 100 ml of CHCl$_3$ was dissolved 6.39 g (0.052 mole) of 2-(3-pyridyl)ethanol followed by dropwise addition of 15.6 ml of thionyl chloride with stirring at room temperature. Then, the mixture was stirred for 1.5 hours, after which the solvent was distilled off. After addition of ether, crystals were recovered by filtration and dried. The procedure gave 9.13 g of 2-(3-pyridyl)ethyl chloride hydrochloride as white crystals.
m.p.: 157–158° C.
NMR (DMSO-d$_6$) δ: 3.33 (t, J=7 Hz, CH$_2$Cl), 4.02 (t, J=7 Hz, CH$_2$-pyridine), 8.10 (dd, J=6 & 8 Hz), 8.64 (m), 8.90 (d, J=6 Hz), 9.00 (d, J=2 Hz), 11.5 (br)

(2) To 32.6 g of 40% aqueous methylamine solution was added 7.48 g (0.042 mole) of 2-(3-pyridyl)ethyl chloride hydrochloride in small portions with stirring. The mixture was transfered to a stainless steel reaction column and heated at an external temperature of 80° C. for 4 hours. After cooling, 3.36 g of NaOH was added with ice-cooling and stirring and the mixture was saturated with sodium chloride and extracted with $CH_2Cl_2$. The extract was dried over $MgSO_4$ and the $CH_2Cl_2$ was distilled off to give 6.32 g of the title compound in crude form as a yellow oil.

NMR ($CDCl_3$) δ: 1.58 (s, NH), 2.44 (s, NMe), 2.82 (m, $CH_2CH_2$), 7.21 (dd, J=5 & 8 Hz, 1H), 7.55 (m, 1H), 8.47 (m, 2H)

REFERENCE EXAMPLE 15

Pyridine-4-aldehyde and pyridine-2-aldehyde were respectively reacted with methylamine in the same manner as Reference Example 6 (1) to give the following compounds.

(1) N-(4-Pyridylmethylidene)methylamine (yellow oil)

NMR ($CDCl_3$) δ: 3.52 (d, J=2 Hz, MeN), 7.53 (m, 2 H, pyridyl-$H_2$), 8.20 (m, CH=N), 8.65 (m, 2H, pyridyl-$H_2$)

IR (neat): 1645, 1590, 1410, 995, 810 $cm^{-1}$ (2) N-(2-Pyridylmethylidene)methylamine (yellow oil)

NMR ($CDCl_3$) δ: 3.54 (d, J=2 Hz, MeN), 7.30 (m, 1 H, pyridine-$H_1$), 7.71 (m, 1H, pyridine-$H_1$), 7.97 (m, 1H, pyridine-$H_1$), 8.40 (m, CH=N), 8.31 (d, J=5 Hz, 1H, pyridine-$H_1$)

IR (neat): 1650, 1585, 1645, 1430, 990, 770 $cm^{-1}$

REFERENCE EXAMPLE 16

The compounds of Reference Example 15 (1) and (2) were respectively reacted in the same manner as Reference Example 6 (2) to give the following compounds.

(1) N-Methyl-N-(4-pyridylmethyl)amine (yellow brown oil)

NMR ($CDCl_3$) δ: 1.86 (br s, NH), 2–44 (s, Me), 3.76 (s, $CH_2$), 7.30 (m, 2H, pyridine-$H_2$), 8.53 (m, 2H, pyridine-$H_2$)

IR (neat): 3260, 1600, 1440, 1410, 790 $cm^{-1}$ (2) N-Methyl-N-(2-pyridylmethyl)amine (orange-colored oil)

NMR ($CDCl_3$) δ: 2.48 (s, Me), 3.87 (s, $CH_2$), 7.0–7.4 (m, 2H, pyridine-$H_2$), 7.64 (t, J=8 Hz, 1H, pyridine-$H_1$), 8.56 (d, J=4 Hz, pyridine-$H_1$)

IR (neat): 1590, 1570, 1470, 1430, 755 $cm^{-1}$

REFERENCE EXAMPLE 17

N-(6-Chloro-3-pyridylmethyl)-N-ethylamine

Using 6-chloro-3-pyridylmethyl chloride and 70% aqueous ethylamine solution, the reaction according to Reference Example 11 was carried out to give the title compound as a brown oil.

NMR ($CDCl_3$) δ: 1.11 (t, J=7 Hz, $CH_2\underline{CH_3}$), 1.43 (s, NH), 2.68 (q, J=7 Hz, $\underline{CH_2}CH_3$), 3.79 (s, $\underline{CH_2}$-pyridine), 7.28 (d, J=8 Hz, 1H), 7.71 (dd, J=2 & 8 Hz, 1H), 8.33 (d, J=2 Hz, 1H)

IR (neat): 1595, 1565, 1460 (sh), 1450, 1380, 1100 $cm^{-1}$

REFERENCE EXAMPLE 18

O-Methyl-N-(3-pyridylmethyl)hydroxylamine

In 200 ml of acetonitrile was suspended 6.6 g (0.04 mole) of 3-pyridylmethyl chloride hydrochloride, followed by addition of 10 g (0.12 mole) of O-methylhydroxyloamine hydrochloride and 16.2 g (0.16 mole) of triethylamine. The mixture was stirred at 50° C. for 15 hours. The insoluble matter was filtered off and the filtrate was concentrated. The residue was subjected to silica gel column chromatography, using $EtOH-CHCl_3$ (1:10) as an eluent. The procedure gave 1.0 g of the title compound as a yellow oil.

NMR ($CDCl_2$) δ: 3.47 (s, 3H), 4.05 (s, 2H), 5.73 (br, NH), 7.27 (dd, J=8 & 5 Hz, 1H), 7.73 (dt, J=8 & 2 Hz, 1H), 8.50–8.70 (m, 2H)

IR (neat): 3200, 1580, 1425, 710 $cm^{-1}$

REFERENCE EXAMPLE 19

(2-Methoxy)ethyl isothiocyanate

In 70 ml of water was dissolved 4.6 g (0.11 mole) of NaOH. Then, 6.4 ml (0.11 mole) of carbon disulfide was added with vigorous stirring and 8.0 g (0.11 mole) of 2-methoxyethylamine was added gradually in droplets. The mixture was stirred at 70° C. for 2 hours, after which 8.2 ml (0.11 mole) of methyl chloroformate was added dropwise at room temperature. The mixture was stirred at 50° C. for 1 hour. The oil separated from the aqueous layer was extracted with ether and dried over $MgSO_4$. The ether was distilled off and the residue was distilled under reduced pressure to give 7.6 g of the title compound as a colorless oil.

b.p: 77–80° C./22 mmHg

NMR ($CDCl_3$) δ: 3.41 (s, 3H), 3.4–3.8 (m, 4H)

IR (neat): 2080, 1720, 1340 $cm^{-1}$

REFERENCE EXAMPLE 20

6-Chloro-3-pyridylmethyl chloride and 6-chloro-3-pyridylmethyl chloride hydrochloride (1) In 70 ml of MeOH was suspended 12.0 g (0.086 mole) of 6-hydroxynicotinic acid followed by addition of 4 ml of concentrated $H_2SO_4$. The mixture was refluxed for 10 hours. After cooling, MeOH was distilled off and the residue was adjusted to pH about 8 with a saturated aqueous solution of sodium hydrogen carbonate. The precipitate was collected by filtration, rinsed (twice) with water and dried to give 10.5 g of methyl 6-hydroxynicotinate as pale yellow crystals. This product was in the pyridone structure.

NMR (DMSO-$d_6$) δ: 3.77 (s, 3H), 6.38 (d, J=10 Hz, 1H), 7.80 (dd, J=10 & 3 Hz, 1H), 8.05 (d, J=3 Hz, 1H), 11 (br)

(2) In 100 ml of acetonitrile was dissolved 4.0 g (0.026 mole) of methyl 6-hydroxynicotinate followed by addition of 0.9 ml of triethylamine. The mixture was refluxed and 3.7 ml of phosphorus oxychloride was added dropwise with stirring over a period of 15 minutes. The mixture was further refluxed for 3 hours. After cooling, the acetonitrile was distilled off and the residue was diluted with 20 ml of water and adjusted to pH about 8 with a saturated aqueous solution of sodium hydrogen carbonate. The resulting crystals are collected by filtration, rinsed with water and dried to give 3.6 g of methyl 6-chloronicotinate as pale yellow needles.

m.p.: 87–88° C.

MNR ($CDCl_3$) δ: 3.97 (s, 3H), 7.44 (d, J=8 Hz, 1H), 8.27 (dd, J=8 & 2 Hz, 1H). 9.02 (d, J=2 Hz, 1H)

IR (Nujol): 1715, 1585, 1440, 1290, 1280, 1125 $cm^{-1}$ (3) To a mixture of 3.0 g (0.0175 mole) of methyl 6-chloronicotinate, 2.0 g of sodium borohydride and 60 ml of THF on reflux, 8.0 ml of MeOH was added with stirring over a period of 1 hour. After completion of the dropwise addition, the mixture was further refluxed for 30 minutes and when cold, the solvent was distilled off. The residue was diluted with 30 ml of water, saturated with NaCl and extracted with $CH_2Cl_2$ (20 ml×3). The $CH_2Cl_2$ layer was dried over $MgSO_4$ and the $CH_2Cl_2$ was distilled off to give 2.3 g of 6-chloro-3-pyridylmethanol as a yellow oil. When left standing at room temperature, this product was thoroughly crystallized.

NMR (CDCl₃) δ: 2.89 (br, 1H), 4.69 (s, 2H), 7.28 (d, J=9 Hz, 1H), 7.69 (dd, J=9 & 3 Hz, 1H), 8.28 (d, J=3 Hz, 1H)

(4) In 500 ml of CHCl₃ was dissolved 47.3 g (0.33 mole) of 6-chloro-3-pyridylmethanol followed by dropwise addition of 99.3 ml of thionyl chloride with stirring at room temperature. After completion of the dropwise addition, the mixture was further stirred for 1.5 hours and, then, allowed to stand overnight. The CHCl₃ was distilled off under reduced pressure, whereby crystals and oil were obtained as a residue. The residue was diluted with ether, collected by filtration and dried to give 45.2 g of 6-chloro-3-pyridylmethyl chloride hydrochloride as white crystals.

NMR (DMSO-d₆) δ: 4.82 (s, 2H), 7.51 (d, J=8 Hz, 1 H), 7.97 (dd, J=8 & 2 Hz, 1H), 8.50 (d, J=2 Hz, 1H)

The mother liquor remaining after separation of the above crop of crystals was concentrated and the insoluble residue was dissolved in EtOH, diluted with toluene and concentrated. The above procedure was carried out for a total of 3 times to recover 9.04 g of crude 6-chloro-3-pyridylmethyl chloride as an oil. (5) In 50 ml of water was suspended 15.0 g (0.076 mole) of 6-chloro-3-pyridylmethyl chloride hydrochloride and the suspension was adjusted to pH about 8 with a saturated aqueous solution of sodium hydrogen carbonate. The resulting mixture was extracted with ether (100 ml×3) and dried over MgSO₄. The ether was then distilled off under reduced pressure to give a crystalline residue. After addition of hexane, the crystals were recovered by filtration, washed with hexane and dried to give 11.0 g of 6-chloro-3-pyridylmethyl chloride as white prisms.

m.p.: 39–40° C.

NMR (CDCl₃) δ: 4.56 (s, 2H), 7.35 (d, J=8 Hz, 1H), 7.73 (dd, J=8 & 2 Hz, 1H), 8.40 (d, J=2 Hz, 1H)

IR (Nujol): 1585, 1445, 1280, 1135, 1105, 820, 740 cm⁻¹

REFERENCE EXAMPLE 21

N-Methyl-N-(2-pyrazinyl)methylamine (1) In 300 ml of CCl₄ was dissolved 9.4 g (0.1 mole) of 2-methylpyrazine followed by addition of 13.4 g of N-chlorosuccinimide and 0.5 g of benzoyl peroxide. The mixture was refluxed for 24 hours. After cooling, the insoluble matter was filtered off and the filtrate was concentrated to give 11.0 g of 2-chloromethylpyrazine as oil.

NMR (CDCl₃) δ: 4.73 (s, 2H), 8.36–8.70 (m, 2H), 8.80 (s, 1H)

(2) The reaction according to Reference Example 11 was carried out using 2-chloromethylpyrazine in lieu of 2,6-dichloro-3-pyridylmethyl chloride to give the title compound as oil.

NMR (CDCl₃) δ: 2.50 (s, 3H), 2.63 (br, 1H), 3.93 (s, 2H), 8.45–8.60 (m, 2H), 8.63 (s, 1H)

REFERENCE EXAMPLE 22

1-[N-(6-Chloro-3-pyridylmethyl)-N-n-propyl]amino-1-methylthio-2-nitroethylene (1) In 15 ml of acetonitrile was dissolved 6.05 g (0.0373 mole) of 6-chloro-3-pyridylmethyl chloride, and under cooling with ice-water and stirring, the solution was added dropwise to a solution of 10.97 g of n-propylamine in 50 ml of acetonitrile. After completion of the dropwise addition, the mixture was stirred at room temperature for 1 hour and at an external temperature of 50° C. for an additional 1 hour. The acetonitrile was distilled off and the residue was diluted with aqueous sodium hydrogen carbonate solution and extracted with CH₂Cl₂ (100 ml×3). The extract was dried over MgSO₄ and distilled to remove CH₂Cl₂, whereby 6.94 g of N-(6-chloro-3-pyridylmethyl)-N-n-propylamine was obtained as a yellow-brown oil.

NMR (CDCl₃) δ: 0.90 (t, J=7 Hz, CH₂C$\underline{H}$₃), 1.32 (s, NH), 1.52 (sextet, J=7 Hz, C$\underline{H}$₂CH₃), 2.59 (t, J=7 Hz, NC$\underline{H}$₂CH₂) 3.79 (s, C$\underline{H}$₂-pyridine), 7.29 (d, J=8 Hz, 1H), 7.71 (dd, J=8 & 2 Hz, 1H), 8.35 (d, J=2 Hz, 1H)

(2) In 100 ml of EtOH was dissolved 4.47 g of 1,1-bis (methylthio)-2-nitroethylene under heating at the reflux temperature. Then, with stirring and refluxing, a solution of 3.50 g (0.0190 mole) of N-(6-chloro-3-pyridylmethyl)-N-n-propylamine in 15 ml of EtOH was added dropwise and the mixture was further refluxed for 12.5 hours. The reaction mixture was allowed to stand at room temperature overnight and the resulting crystals were filtered off. The filtrate was concentrated and the residue was subjected to silica gel (250 g) column chromatography using EtOH-CHCl₃ (1:20) as an eluent. The procedure gave 2.98 g of the title compound as a yellow viscous oil.

NMR (CDCl₃) δ: 0.90 (t, J=7 Hz, CH₂C$\underline{H}$₃), 1.68 (sextet, J=7 Hz, C$\underline{H}$₂CH₃), 2.46 (s, MeS), 3.42 (t, J=7 Hz, NCH₂C$\underline{H}$₂), 4.70 (s, CH₂-pyridine), 6.80 (s, =CHNO₂), 7.36 (d, J=8 Hz, 1H), 7.61 (dd, J=8 & 2 Hz, 1H), 8.29 (d, J=2 Hz, 1H)

REFERENCE EXAMPLE 23

1-[N-(6-Chloro-3-pyridylmethyl)-N-i-propyl]amino-1-methylthio-2-nitroethylene

The reactions according to (1) and (2) of Reference Example 22 were carried out using i-propylamine in lieu of n-propylamine to give the following compounds at the respective steps.

(1) N-(6-Chloro-3-pyridylmethyl)-N-i-propylamine (oil)

NMR (CDCl₃) δ: 1.07 (d, J=6 Hz, $\underline{Me}$₂CH), 1.21 (br s, NH), 2.84 (septet, J=6 Hz, CH$\underline{Me}$₂), 3.77 (s, CH₂), 7.28 (d, J=8 Hz, 1H), 7.71 (dd, J=8 & 2 Hz, 1H), 8.35 (d, J=2 Hz, 1H)

(2) Title compound (viscous oil)

NMR (CDCl₃) δ: 1.35 (d, J=7 Hz, CH$\underline{Me}$₂), 2.38 (s, MeS), 4.64 (s, CH₂), 6.57 (s, =CHNO₂)

REFERENCE EXAMPLE 24

2-Chloro-5-methylaminopyridine

To 5.0 g (0.039 mole) of 5-amino-2-chloropyridine was added 40 ml of ethyl orthoformate and the mixture was refluxed for 5 hours. The reaction mixture was concentrated under reduced pressure and the residue was dissolved in 50 ml of EtOH. After addition of 1.8 g of sodium borohydride, the mixture was stirred at 70–80° C. for 3 hours. The reaction mixture was concentrated and after addition of 50 ml of iced water and 5 ml of concentrated hydrochloric acid, the mixture was adjusted to pH 7–8 with NaHCO₃ and extracted with AcOEt (50 ml×3). The AcOEt layers were pooled, washed with water and dried over MgSO₄. The AcOEt was distilled off and hexane was added to the crystalline residue. The crystals are collected by filtration, washed with hexane and dried to give 5.1 g of the title compound as white crystals.

m.p.: 70° C.

NMR (CDCl₃) δ: 2.85 (br d, J=4.5 Hz, 3 H), 3.3–4.3 (m, 1 H), 6.87 (dd, J=8.0 & 3.0 Hz, 1 H), 7.11 (d, J=8.7 Hz, 1 H), 7.78 (d, J=3.3 Hz, 1 H).

REFERENCE EXAMPLE 25

N-(2,6-Dimethyl-4-pyridylmethyl)-N-methylamine (1) In 77 ml of CHCl₃ was dissolved 7.00 g (0.0511 mole) of (2,6-dimethyl-4-pyridyl)methanol and with stirring at room temperature, 15.3 ml of thionyl chloride was added dropwise. After completion of the dropwise addition, the mixture was stirred for 3 hours and concentrated. The residue was diluted with aqueous sodium hydrogen carbonate solution and extracted with AcOEt (100 ml×3) The extract was dried over $MgSO_4$ and distilled to remove AcOEt. The procedure gave 6.37 g of (2,6-dimethyl-4-pyridyl)methyl chloride as oil.

NMR ($CDCl_3$) δ: 2.53 (s, Me×2), 4.45 (s, $CH_2$), 6.98 (s, pyridine-$H_2$)

(2) The reaction according to Reference Example 11 was carried out using (2,6-dimethyl-4-pyridyl)methyl chloride in lieu of 2,6-dichloro-3-pyridylmethyl chloride to give the title compound as oil.

NMR ($CDCl_3$):2.44 (s, NMe), 2.50 (s, pyridine-Me×2), 3.68 (s, $CH_2$) 6.94 (s, pyridine-$H_2$)

REFERENCE EXAMPLE 26

N-(2-Chloro-3-pyridylmethyl)-N-methylamine (1) To 10.24 g (0.065 mole) of 2-chloronicotinic acid were added 20 ml of 1,2-dichloroethane and 9.5 ml of thionyl chloride and the mixture was refluxed for 1 hour. The reaction mixture was concentrated to give 11.9 g of 2-chloronicotinyl chloride as an orange-colored oil. When left standing at room temperature, this product solidified thoroughly.

NMR ($CDCl_3$) δ: 7.54 (dd, J=8 & 5 Hz, 1 H), 8.48 (dd, J=8 & 1 Hz, 1 H), 8.65 (dd, J=5 & 1 Hz, 1 H)

(2) In 100 ml of cold water was dissolved 8.98 g of sodium borohydride and with ice-cooling and stirring, 11.7 g (0.0665 mole) of 2-chloronicotinyl chloride was added in small portions. The mixture was further stirred at the same temperature for 30 minutes and, then, extracted with $Et_2O$ (100 ml×3). The extract was dried over $MgSO_4$ and distilled to remove $Et_2O$. The procedure gave 8.75 g of (2-chloro-3-pyridyl)methanol as a pale yellow oil. When left standing at room temperature, this product solidified thoroughly.

NMR ($CDCl_3$) δ: 4.53 (br, OH), 4.77 (s, $CH_2$), 7.30 (m, 1 H), 7.97 (m, 1 H), 8.25 (m, 1 H)

(3) The reaction according to Reference Example 25 (1) was carried out using (2-chloro-3-pyridyl)methanol in lieu of (2,6-dimethyl-4-pyridyl)methanol to give (2-chloro-3-pyridyl)methyl chloride as a yellow oil.

NMR ($CDCl_3$) δ: 4.71 (s, $CH_2$), 7.31 (dd, J=8 & 5 Hz, 1 H), 7.88 (dd, J=8 & 2 Hz, 1 H) 8.33 (dd, J=5 & 2 Hz, 1 H)

(4) The reaction according to Reference Example 11 was carried out using (2-chloro-3-pyridyl)methyl chloride in lieu of 2,6-dichloro-3-pyridylmethyl chloride to give the title compound as a yellow oil.

NMR ($CDCl_3$) δ: 1.95 (s, NH), 2.47 (s, Me), 3.84 (s, $CH_2$), 7.26 (dd, J=8 & 5 Hz, 1 H), 7.80 (dd, J=8 & 2 Hz, 1 H), 8.30 (dd, J=5 & 2 Hz, 1 H)

REFERENCE EXAMPLE 27

2-Methyl-5-methylaminopyridine oxalate

To 5.0 g (0.04 mole) of 5-amino-2-methylpyridine was added 40 ml of ethyl orthoformate and the mixture was refluxed for 1 hour. The reaction mixture was concentrated under reduced pressure and the residue was dissolved in 50 ml of EtOH, followed by addition of 2.1 g of sodium borohydride. The mixture was refluxed with stirring for 2.5 hours. The reaction mixture was concentrated and 50 ml of ice-water and 8 ml of concentrated hydrochloric acid were added to the residue. The mixture was adjusted to pH 7 with $NaHCO_3$ and extracted with AcOEt (50 ml, 30 ml×2). The AcOEt layers were combined, washed with aqueous sodium chloride solution and dried over $MgSO_4$. The AcOEt was distilled off and the residue was diluted with $Et_2O$ and the insoluble matter was filtered off. To the filtrate was added a solution of oxalic acid in EtOH (ca. 10%) and the resulting crystals were collected by filtration, washed with EtOH and dried. The procedure gave 4.3 g of the title compound as pale yellow crystals.

m.p.: 118.5–119.5° C.

NMR (DMSO-$d_6$) δ: 2.43 (3 H, s), 2.73 (3 H, s), 7.1–7.5 (2 H, m), 7.8–8.0 (1 H, m), 8.2–9.0 (m)

REFERENCE EXAMPLE 28

N-(5-Bromo-3-pyridylmethyl)-N-methylamine

The steps (1), (2), (3) and (4) of Reference Example 26 were repeated except that 5-bromonicotinic acid was used in lieu of 2-chloronicotinic acid to obtain the following compounds in the respective steps.

(1) 5-Bromonicotinyl chloride (white crystals)

NMR ($CDCl_3$) δ: 8.54 (m, 1 H), 8.99 (d, J=1 Hz, 1 H), 9.25 (d, J=1 Hz, 1 H)

(2) (5-Bromo-3-pyridyl)methanol (crude orange-colored oil)

NMR ($CDCl_3$) δ: 4.39 (br s, OH), 4.73 (s, $CH_2$), 7.90 (m, 1 H), 8.47 (d, J=1 Hz, 1 H), 8.55 (d, J=2 Hz, 1 H)

(3) (5-Bromo-3-pyridyl)methyl chloride (crude oil)

NMR ($CDCl_3$) δ: 4.57 (s, $CH_2$), 7.92 (m, 1 H), 8.56 (d, J=1 Hz, 1 H), 8.65 (d, J=1 Hz, 1 H)

(4) Title compound (crude oil)

NMR ($CDCl_3$) δ: 2.44 (s, Me), 3.76 (s, $CH_2$), 7.89 (m, 1 H), 8.48 (d, J=1 Hz, 1 H), 8.57 (d, J=1 Hz, 1 H)

REFERENCE EXAMPLE 29

N-(2-Methylthio-3-pyridylmethyl)-N-methylamine

The steps (1), (2), (3) and (4) of Reference Example 26 were repeated except that 2-methylthionicotinic acid was used in lieu of 2-chloronicotinic acid to obtain the following compounds in the respective steps.

(1) 2-Methylthionicotinyl chloride (white—pale yellow crystals)

NMR ($CDCl_3$) δ: 2.56 (s, MeS), 7.17 (dd, J=5 & 8 Hz, 1 H), 8.52 (dd, J=8 & 2 Hz, 1 H), 8.67 (dd, J=5 & 2 Hz, 1 H)

(2) (2-Methylthio-3-pyridyl)methanol (pale yellow oil, crystallized thoroughly on standing)

NMR ($CDCl_3$) δ: 2.56 (s, MeS), 3.46 (br s, OH), 4.62 (s, $CH_2$), 6.99 (dd, J=5 & 8 Hz, 1 H), 7.62 (dd, J=8 & 1 Hz, 1 H), 8.33 (dd, J=5 & 8 Hz, 1 H)

(3) (2-Methylthio-3-pyridyl)methyl chloride (pale yellow oil)

NMR ($CDCl_3$) δ: 2.61 (s, MeS), 4.60 (s, $CH_2$), 6.99 (dd, J=5 & 8 Hz, 1 H), 7.58 (dd, J=8 & 2 Hz, 1 H), 8.43 (dd, J=5 & 2 Hz, 1 H)

(4) Title compound (yellow oil)

NMR ($CDCl_3$) δ: 1.50 (s, NH), 2.44 (s, MeN), 2.57 (s, MeS), 3.73 (s, $CH_2$), 6.97 (dd, J=5 & 8 Hz, 1 H), 7.51 (dd, J=8 & 1 Hz, 1 H), 8.37 (dd, J=5 & 1 Hz, 1 H)

REFERENCE EXAMPLE 30

N-Methyl-N-(4-thiazolyl)methylamine (1) The reaction procedure of Reference Example 21 (1) was repeated except that 4-methylthiazole was used in lieu of 2-methylpyrazine to give crude 4-chloromethyl-thiazole as oil.

NMR (CDCl$_3$) δ: 4.72 (s, CH$_2$Cl), 7.37 (m, 1 H), 8.78 (d, J=2 Hz, 1 H)

(2) The reaction procedure of Reference Example 11 was repeated except that crude 4-chloromethylthiazole was used in lieu of 2,6-dichloro-3-pyridylmethyl chloride and the reaction Was conducted at room temperature for 1 hour and further at 50° C. for 2 hours. The procedure gave the title compound as a crude oil.

NMR (CDCl$_3$) δ: 2.43 (s, MeN), 3.89 (s, CH$_2$), 7.17 (m, 1 H), 8.74 (d, J=2 Hz, 1 H)

REFERENCE EXAMPLE 31

2-Chloro-5-ethylaminopyridine

A mixture of 10 g (0.078 mole) of 5-amino-2-chloropyridine and 50 ml of ethyl orthoacetate was refluxed for 2 hours. The reaction mixture was concentrated under reduced pressure and the residue was dissolved in 60 ml of dry THF. Then, the solution was added dropwise to a suspension of 7.0 g of lithium borohydride in 100 ml of dry THF over a period of 15 minutes with constant stirring. After completion of dropwise addition, the mixture was refluxed with stirring for 27 hours. After cooling, the solvent was distilled off. To the residue were added 100 ml of ice-water and 35 ml of concentrated hydrochloric acid and the mixture was heated at 67° C. for a while. After cooling, the reaction mixture was adjusted to pH 7 with NaHCO$_3$ and extracted with AcOEt (50 ml×3). The AcOEt layers were combined, washed with aqueous sodium chloride solution and dried over MgSO$_4$. The AcOEt was distilled off and the residual crystals were collected by filtration, washed with hexane and dried. The procedure gave 9.2 g of the title compound as pale yellowish green crystals.

m.p.: 65–66° C.

NMR (CDCl$_3$) 67 :1.25 (3 H, t, J=7.4 Hz), 2.9–3.4 (2 H, m), 3.4–4.1 (1 H, m, NH), 6.86 (1 H, dd, J=9.0 & 3.0 Hz), 7.09 (1 H, d, J=7.8 Hz), 7.77 (1 H, d, J=2.7 Hz).

REFERENCE EXAMPLE 32

2-Chloro-5-n-propylaminopyridine (1) To 6.4 g (0.05 mole) of 5-amino-2-chloropyridine was added 25 g of triethyl orthopropionate and the mixture was refluxed for 3 hours. Then, at an external temperature of 70° C., the reaction mixture was concentrated under reduced pressure using a vacuum pump. The procedure gave 10.5 g of N-(6-chloro-3-pyridyl)-O-ethylpropionimidate as a yellow oil.

NMR (CDCl$_3$) δ: 1.07 (t, J=8 Hz, 3 H), 1.33 (t, J=7 Hz, 3 H), 2.16 (q, J=8 Hz, 2 H), 4.22 (q, J=7 Hz, 2 H), 7.06 (dd, J=8 & 3 Hz, 1 H), 7.25 (d, J=8 Hz, 1 H), 7.87 (d, J=3 Hz, 1 H)

(2) To a 70% solution of sodium dihydro-bis(2-methoxyethoxy)aluminate in toluene was added 100 ml of toluene and a solution of 8.5 g (0.04 mole) of N-(6-chloro-3-pyridyl)-O-ethylpropionimidate in 20 ml of toluene was added dropwise over 5 minutes with stirring at room temperature. The mixture was further stirred at room temperature for 1 hour and at 50° C. for 2 hours, after which 50 ml of water was added dropwise over 5 minutes under ice-cooling. The mixture was stirred at 50° C. for 15 minutes. The toluene layer was separated, dried over MgSO$_4$ and concentrated and the residue was subjected to silica gel column chromatography using hexane-acetone (2:1) as the eluent. The procedure gave 5.9 g of the title compound as a yellow oil.

NMR (CDCl$_3$) δ: 0.99 (t, J=7 Hz, 3 H), 1.65 (m, 2 H), 3.07 (dt, J=7 & 6 Hz, 2 H), 3.83 (br, 1 H), 6.86 (dd, J=8 & 3 Hz, 1 H), 7.10 (d, J=8 Hz, 1 H), 7.77 (d, J=3 Hz, 1 H)

REFERENCE EXAMPLE 33

2-Chloro-5-n-butylaminopyridine

The steps (1) and (2) of Reference Example 32 were repeated except that trimethyl orthobutyrate was used in lieu of triethyl orthopropionate to obtain the following compounds in the respective steps.

(1) N-(6-Chloro-3-pyridyl)-O-methyl butyrimidate (yellow oil)

NMR (CDCl$_3$) δ: 0.85 (t, J=7 Hz, 3 H), 1.33–1.80 (m, 2 H), 2.16 (t, J=7 Hz, 2 H), 3.80 (s, 3 H), 7.06 (dd, J=8 & 3 Hz, 1 H), 7.27 (d, J=8 Hz, 1 H), 7.88 (d, J=3 Hz, 1 H)

(2) Title compound (yellow crystals)

m.p.: 46–48° C.

NMR (CDCl$_3$) δ: 0.93 (t, J=7 Hz, 3 H), 1.16–1.83 (m, 4 H), 3.08 (dt, J=7 & 6 Hz, 2 H), 3.78 (br, 1 H), 6.84 (dd, J=8 & 3 Hz, 1 H), 7.08 (d, J=8 Hz, 1 H), 0.75 (d, J=3 Hz, 1 H)

REFERENCE EXAMPLE 34

3-Methylamino-5-trifluoromethylpyridine

The reaction procedure of Reference Example 24 was repeated except that 3-amino-5-trifluoromethylpyridine was used in lieu of 5-amino-2-chloropyridine to obtain the title compound as white crystals.

m.p. : 69–70° C.

NMR (CDC$_3$):2.89 (3 H, d, J=5.1 Hz), 3.8–4.5 (1 H, m, NH, 6.9–7.1 (1 H, m), 8.1–8.3 (2 H, m)

REFERENCE EXAMPLE 35

N-Methyl-N-(6-methyl-3-pyridylmethyl)amine (1) The reaction procedure of Reference Example 20 (3) was repeated except that methyl 6-methylnicotinate was used in lieu of methyl 6-chloronicotinate to give crude 6-methyl-3-pyridylmethanol as a yellow oil.

NMR (CDCl$_3$) δ: 2.49 (s, Me), 4.66 (s, CH$_2$), 4.93 (br, OH), 7.14 (d, J=8 Hz, 1 H), 7.63 (dd, J=8 & 2 Hz, 1 H), 8.36 (d, J=2 Hz, 1 H)

(2) The reaction procedure of Reference Example 25 (1) was repeated except that crude 6-methyl-3-pyridyl-methanol was used in lieu of (2,6-dimethyl-4-pyridyl)-methanol to give crude (6-methyl-3-pyridyl)methyl chloride as oil.

NMR (CDCl$_3$) δ: 2.54 (s, Me), 4.55 (s, CH$_2$), 7.16 (d, J=8 Hz, 1 H), 7.62 (dd, J=8 & 2 Hz, 1 H), 8.49 (dd, J=2 Hz, 1 H)

(3) A mixture of 16.6 g of 40% aqueous MeNH$_2$ solution and 52 ml of CH$_3$CN was cooled with ice and 6.08 g (0.043 mole in terms of pure product) of crude (6-methyl-3-pyridyl)-methyl chloride was added dropwise with constant stirring. After completion of dropwise addition, the mixture was stirred at room temperature for 1.5 hours, at the end of which time the solvent was distilled off. The solid residue was extracted with CH$_2$Cl$_2$ and the CH$_{Cl2}$ layer was dried over MgSO$_4$. The CH$_2$Cl$_2$ was distilled off and the residue was diluted with 70 ml of Et$_2$O and filtered to remove the insoluble matter. Finally the filtrate was concentrated to recover 4.60 g of the title compound as a crude oil.

NMR (CDCl$_3$) δ: 2.43 (s, MeN), 2.53 (s, pyridine-Me), 3.71 (s, CH$_2$), 7.13 (d, J=8 Hz, 1 H), 7.57 (dd, J=8 & 2 Hz, 1 H), 8.40 (d, J=2 Hz, 1 H)

REFERENCE EXAMPLE 36

N-(6-Fluoro-3-pyridylmethyl)-N-methylamine (1) A mixture of 7.2 g (0.0648 mole) of 2-fluoro-5-methylpyridine, 12.0 g of N-bromosuccinimide, 0.5 g of benzoyl peroxide and 200 ml of $CCl_4$ was refluxed for 2 hours. After cooling, the precipitate was filtered off and the filtrate was washed with water and dried. Finally, the $CCl_4$ was distilled off to recover 12.68 g of crude (6-fluoro-3-pyridyl)methyl bromide as a pale yellow oil.

NMR ($CDCl_3$) δ: 4.47 (2 H, s, $CH_2$), 6.96 (1 H, dd, J=8.4 & 2.7 Hz), 7.86 (1 H, ddd, J=8.4, 2.4 & 8.4 Hz), 8.29 (1 H, d, J=2.4 Hz)

(2) To a mixture of 2.5 g of 40% aqueous methylamine solution and 30 ml of $CH_3CN$ was added dropwise 3.0 g of crude (6-fluoro-3-pyridyl)methyl bromide with constant stirring. The mixture was allowed to stand at room temperature overnight and concentrated under reduced pressure. The residue was extracted with AcOEt and the extract was dried over $MgSO_4$ and concentrated. The procedure gave 1.35 g of the title compound as a crude orange-colored oil.

NMR ($CDCl_3$) δ: 2.53 (3 H, s, Me), 3.94 (2 H, s, $CH_2$) 5.40 (1 H, s, NH)

REFERENCE EXAMPLE 37

N-(6-Bromo-3-pyridylmethyl)-N-methylamine (1) The reaction procedure of Reference Example 36 (1) was repeated except that 2-bromo-5-methylpyridine was used in lieu of 2-fluoro-5-methylpyridine to recover crude (6-bromo-3-pyridyl)methyl bromide as a yellow oil.

NMR ($CDCl_3$) 67 :4.42 (2 H, s), 7.48 (1 H, d, J=8.4 Hz), 7.61 (1 H, dd, J=8.4 & 2.7 Hz), 8.40 (1 H, d, J=2.7 Hz).

(2) To a mixture of 12.3 g of 40% aqueous methylamine solution and 40 ml of $CH_3CN$ was added 8.0 g of crude (6-bromo-3-pyridyl)methyl bromide with stirring. The mixture was further stirred at room temperature for 30 minutes. The reaction mixture thus obtained was concentrated and the residue was diluted with toluene and subjected to azeotropic distillation to remove the water. Then, the soluble fraction was extracted with $Et_2O$. The $Et_2O$ layer was dried over $MgSO_4$ and concentrated to recover 4.4 g of the title compound as a yellow oil.

NMR ($CDCl_3$) δ: 2.48 (3 H, s), 2.73 (1 H, s), 3.80 (2 H, s), 7.45 (1 H, d, J=8.4 Hz), 7.63 (1 H, dd, J=8.4 & 2.7 Hz), 8.36 (1 H, d, J=2.7 Hz)

REFERENCE EXAMPLE 38

N-(6-Bromo-3-pyridylmethyl)-N-ethylamine

The reaction procedure of Reference Example 37 (2) was repeated except that 70% aqueous ethylamine solution was used in lieu of 40% aqueous methylamine solution to recover the title compound as a crude oil.

NMR ($CDCl_3$) δ: 1.11 (3 H, t, J=8.1 Hz), 2.16 (1 H, br s), 2.68 (2 H, q, J=8.1 Hz), 3.78 (2 H, s), 7.45 (1 H, d, J=8.4 Hz), 7.58 (1 H, dd, J=8.4 & 2.7 Hz), 8.33 (1 H, d, J=2.7 Hz)

REFERENCE EXAMPLE 39

N-(2-Chloro-5-thiazolylmethyl)-N-methylamine

The reaction procedure of Reference Example 11 was repeated except that crude 2-chloro-5-chloromethyl-thiazole was used in lieu of 2,6-dichloro-3-pyridylmethyl chloride and that $CH_2Cl_2$ was used as the extractant. The procedure gave the title compound as a crude oil.

NMR ($CDCl_3$) δ: 2.45 (s, MeN), 3.89 (s, $CH_2$), 7.37 (s, thiazole-H)

REFERENCE EXAMPLE 40

N-(2-Chloro-5-thiazolylmethyl)-N-ethylamine

The reaction procedure of Reference Example 17 was repeated except that crude 2-chloro-5-chloromethylthiazole was used in lieu of 6-chloro-3-pyridylmethyl chloride and that $CH_2Cl_2$ was used as the extractant. The procedure gave the title compound as a crude oil.

NMR ($CDCl_3$) δ: 1.10 (t, J=7 Hz, $CH_2C\underline{H}_3$), 2.69 (q, J=7 Hz, $C\underline{H}_2CH_3$), 3.93 (s, $CH_2N$), 7.36 (s, thiazole-H)

REFERENCE EXAMPLE 41

2-Chloro-5-thiazolylmethylamine (1) The reaction procedure of Reference Example 10 (1) was repeated except that crude 2-chloro-5-chloromethylthiazole was used in lieu of 2,6-dichloro-3-pyridylmethyl chloride to give N-(2-chloro-5-thiazolylmethyl)-phthalimide as pale yellow crystals.

m.p.: 108–109° C.

NMR ($CDCl_3$) δ: 4.97 (2 H, s), 7.60 (1 H, s), 7.6–8.1 (m, 4 H)

(2) The reaction procedure of Reference Example 3 was repeated except that N-(2-chloro-5-thiazolylmethyl)-phthalimide was used in lieu of N-(6-chloro-3-pyridylmethyl)phthalimide to give the title compound as a yellow oil.

NMR ($CDCl_3$) δ: 1.68 (2 H, br s), 4.04 (2 H, s), 7.38 (1 H, s)

REFERENCE EXAMPLE 42

2-Methoxy-5-methylaminopyridine

The reaction procedure of Reference Example 24 was repeated except that 5-amino-2-methoxypyridine was used in lieu of 5-amino-2-chloropyridine to give the title compound as a yellow oil.

NMR ($CDCl_3$) δ: 2.81 (3 H, s), 3.1–3.8 (1 H, m), 3.87 (3 H, s), 6.64 (1 H, d, J=9.0 Hz), 6.98 (1 H, dd, J=8.7 & 3.2 Hz), 7.59 (1 H, d, J=2.4 Hz)

REFERENCE EXAMPLE 43

6-Bromo-3-pyridylmethylamine (1) The reaction procedure of Reference Example 10 (1) was repeated except that crude 6-bromo-3-pyridylmethyl bromide was used in lieu of 2,6-dichloro-3-pyridylmethyl chloride, to give N-(6-bromo-3-pyridylmethyl)phthalimide as white crystals.

m.p.: 130–131° C.

NMR ($CDCl_3$)δ: 4.83(s,2 H), 7.44 (d,J=8 Hz, 1 H), 7.6–8.0 (m,5 H), 8.49 (d,J=2 Hz, 1 H)

(2) The reaction procedure of Reference Example 3 was repeated except that N-(6-bromo-3-pyridylmethyl) phthalimide was used in lieu of N-(6-chloro-3-pyridylmethyl)phthalimide, to give the title compound as sale yellow crystals.

m.p.: 57–58° C.

NMR ($CDCl_3$)δ: 1.46 (br s,2 H), 3.86 (s,2 H), 7.42 (d, J=8 Hz, 1 H), 7.58 (dd, J=8 & 2 Hz, 1 H), 8.32 (d,J=2 Hz, 1 H)

REFERENCE EXAMPLE 44

N-(6-Chloro-3-pyridylmethyl)-N-(2,2,2-trifluoroethyl)amine

In 15 ml of water was dissolved 12.55 g of 2,2,2-trifluoroethylamine hydrochloride, followed by addition of 68 ml of CH$_3$CN, and further 9.35 g of Et$_3$N and then 3.00 g (0.0185 mole) of 6-chloro-3-pyridylmethyl chloride under cooling with ice-water and stirring. The mixture was stirred at room temperature for one hour, at 50° C. for one hour and at 70° C. for 90 hours. The CH$_3$CN was distilled off, and the residue was followed by addition of NaHCO$_3$ and then extracted with CH$_2$Cl$_2$ (100 ml×3). The extract was dried over MgSO$_4$ and distilled to remove CH$_2$Cl$_2$. To the residue was added 100 ml of Et$_2$O and the resulting unsoluble matter was filtered off. The filtrate was concentrated to give 3.85 g of the title compound as yellow oil.

NMR (CDCl$_3$)δ: 1.81 (br, NH), 3.21 (q,J=9 Hz, CF$_3$CH$_2$), 3.92 (s,pyridine-CH$_2$), 7.30 (d,J=8 Hz, 1 H), 7.71 (dd, J=8 & 2 Hz, 1 H), 8.32 (d,J=2 Hz, 1 H)

Example 1

1-Methylthio-1-(3-pyridylmethyl)amino-2-nitroethylene (Compound 1-1) and 1,1-bis(3-pyridylmethyl)-amino-2-nitroethylene (Compound 1-2)

In 100 ml of EtOH was dissolved 5.0 g (0.03 mole) of 1,1-bis(methylthio)-2-nitroethylene with heating and, then, a solution of 3.2 g (0.03 mole) of 3-pyridylmethylamine in 30 ml of EtOH was added dropwise in 3 installments at intervals of 20–30 minutes while refluxing. The mixture was further refluxed for 2 hours and the EtOH was distilled off. The residue was subjected to silica gel column chromatography using CHCl$_3$ -MeOH (5:1) as an eluent. The procedure gave 4.0 g and 0.5 g of the title Compounds (1-1 and 1-2), respectively, each as a white powder.

Compound 1-1 m.p.: 129–130° C.

Compound 1-2 m.p.: 141–143° C.

NMR (DMSO-d$_6$) δ: 4.55 (d), 6.52 (s), 10.26 (br s) IR (Nujol) :3150, 1575, 1390 cm$^{-1}$

Example 2

1-Methylthio-1-(N-methyl-N-3-pyridylmethyl)amino-2-nitroethylene (Compound 2)

The procedure of Example 1 was repeated except that N-methyl-N-pyridylmethylamine was used in lieu of 3-pyridylmethylamine to give the title compound as a pale yellow viscous oil.

NMR (CDCl$_3$) δ: 2.50 (s), 3.06 (s), 4.81 (s), 6.81 (s)

Example 3

1-Methylamino-1-(3-pyridylmethyl)amino-2-nitroethylene (Compound 3)

In 50 ml of EtOH was dissolved 2.3 g (0.01 mole) of 1-methylthio-1-(3-pyridylmethyl)amino-2-nitroethylene with heating and, then, a solution of 1:2 g (0.015 mole) of 40% aqueous methylamine in 10 ml of EtOH was added dropwise over a period of 30 minutes while refluxing. The mixture was further refluxed for 2 hours, after which it was concentrated. The crystals were collected by filtration and recrystallized from acetonitrile to give 1.6 g of the title compound as white prisms.

m.p.: 159–160° C.

NMR (DMSO-d$_6$) δ: 2.86 (br s), 4.49 (d), 6.46 (s)

Example 4

1-Methylthio-1-(3-pyridylmethyl)amino-2-nitroethylene was reacted with various amines (or ammonium) in the same manner as Example 3 and the reaction product was purified by recrystallization or silica gel column chromatography to give the following compounds 4-22.

(1) 1-Ethylamino-1-(3-pyridylmethyl)amino-2-nitroethylene (Compound 4)

m.p.: 161–162° C.

(2) 1-iso-propylamino-1-(3-pyridylmethyl)amino-2-nitroethylene (Compound 5)

m.p.: 148–150° C.

NMR (CDCl$_3$) δ: 4.46 (d), 6.52 (s), 7.28 (br s), 10.1 (br s)

(3) 1-n-Butylamino-1-(3-pyridylmethyl)amino-2-nitroethylene (Compound 6)

m.p.: 110–112° C.

(4) 1-Allylamino-1-(3-pyridylmethyl)amino-2-nitroethylene (Compound 7)

m.p.: 114–115° C.

(5) 1-n-Pentylamino-1-(3-pyridylmethyl)amino-2-nitroethylene (Compound 8)

m.p.: 97–98° C.

(6) 1-Anilino-1-(3-pyridylmethyl)amino-2-nitroethylene (Compound 9)

m.p.: 217–218° C.

(7) 1-Amino-1-(3-pyridylmethyl)amino-2-nitroethylene (Compound 10)

m.p.: 177–178° C. (decompn.)

(8) 1-(2-n-Propylthioethyl)amino-1-(3-pyridylmethyl)-amino-2-nitroethylene (Compound 11) (white prisms)

m.p.: 93–94° C.

NMR (CDCl$_3$) δ: 4.48 (d), 6.23 (br s), 6.63 (s), 10.5 (br s)

(9) 1-(2-Dimethylaminoethyl)amino-1-(3-pyridylmethyl)-amino-2-nitroethylene (Compound 12) (white prisms)

m.p.: 110–111° C.

NMR (CDCl$_3$) δ: 2.02 (s), 4.30 (m), 6.60 (s), 10.3 (br s)

(10) 1-(2-Hydroxyethyl)amino-1-(3-pyridylmethyl) amino-2-nitroethylene (Compound 13)

m.p. 161–163° C.

(11) 1-(2-Methoxyethyl)amino-1-(3-pyridylmetyl) amiino-2-nitroethylene (Compound 14)

m.p.: 108–109° C.

(12) 1-(2,2-Dimethoxyethyl)amino-1-(3-pyridylmethyl)-amino-2-nitroethylene (Compound 15) (white prisms)

m.p.: 96–98° C.

NMR (CDCl$_3$) δ: 6.55 (s), 6.85 (br s), 10.3 (br s)

(13) 1-(3-Pyridylmethyl)amino-1-(2,2,2-trifluoroethyl)-amino-2-nitroethylene (Compound 16)

m.p.: 164–165° C.

NMR (DMSO-d$_6$) δ: 4.09 (m), 6.58 (s)

(14) 1-(3-Pyridylmethyl)amino-1-(trimethylsilylmethyl)-amino-2-nitroethylene (Compound 17)

m.p.: 156–157° C.

NMR (CDCl$_3$) δ: 0.10 (s), 2.67 (d), 4.32 (d), 6.37 (s), 7.12 (br s), 10.1 (br s)

(15) 1-Hydrazino-1-(3-pyridylmethyl)amino-2-nitroethylene (Compound 18)

m.p.: 176–177° C. (decompn.)

(16) 1-Dimethylamino-1-(3-pyridylmethyl)amino-2-nitroethylene (Compound 19)

m.p.: 68–70° C.

NMR (CDCl$_3$) δ: 2.93 (s), 4.48 (d), 6.52 (s), 9.77 (br s)

(17) 1-(3-Pyridylmethyl)amino-1-pyrrolidino-2-nitroethylene (Compound 20) (pale yellow powder)

m.p.: 103–105° C.

NMR (CDCl$_3$) δ: 4.61 (d), 6.63 (s), 10.42 (br s)

(18) 1-(4-Methylpiperazino)-1-(3-pyridylmethyl)amino-2-nitroethylene (Compound 21)

NMR (CDCl$_3$) δ: 2.32 (s), 2.46 (t), 3.25 (t), 4.53 (d), 6.50 (s), 9.73 (br s)

(19) 1-(Morpholino)-1-(3-pyridylmethyl)amino-2-nitroethylene (Compound 22)

m.p.: 102–103° C.

Example 5

1-Piperidino-1-(3-pyridylmethyl)amino-2-nitroethylene (Compound 23)

In 20 ml of EtOH was dissolved 0.8 g (0.004 mole) of 1-methylthio-1-piperidino-2-nitroethylene followed by addition of 0.4 g (0.004 mole) of 3-pyridiylmethylamine. The mixture was refluxed for 2 hours. The ethanol was distilled off and the residue was purified by silica gel column chromatography to give 0.3 g of the title compound as a pale yellow powder.

m.p.: 106–108° C.

Example 6

1-(2,2-Dimethyl-1-hydrazino)-1-(3-pyridylmethyl)-amino-2-nitroethylene (Compound 24)

The procedure of Example 5 was repeated using 1-(2,2-dimethyl-1-hydrazino)-1-methylthio-2-nitroethylene to give the title compound as white prisms.

m.p.: 158–159° C.

NMR (CDCl$_3$) δ: 2.63 (s), 4.36 (d), 6.45 (s), 6.85 (br s), 10.36 (br s)

Example 7

1-Amino-1-(N-methyl-N-3-pyridylmethyl)amino-2-nitroethylene (Compound 25)

In 50 ml of MeOH was dissolved 7.2 g (0.03 mole) of 1-methylthio-1-(N-methyl-N-3-pyridylmethyl)amino-2-nitroethylene followed by addition of 10 ml of 25% agueous ammonia. The mixture was resfluxed for 2 hours, ater which the solvent was distilled off. The resisdue was subjected to silica gel column chromatography using CHCl$_3$—MeOH (5:1) as an eluent to give 1.5 g of the title compound as white prisms.

m.p.: 158–159° C.

NMR (DMSO-d$_6$) δ: 3.06 (s), 4.66 (s), 6.63 (s), 8.93 (br s)

Example 8

1-Methylamino-1-(N-methyl-N-3-pyridylmethyl)amino-2-nitroethylene (Compound 26)

(1) In 30 ml of toluene was dissolved 2.5 g (0.02 mole) of N-methyl-N-3-pyridylmethylamine followed by addition of 1.5 g (0.02 mole) of methyl isothiocyanate and the mixture was stirred at room temperature overnight. Finally, the solvent was distilled off to give 3.8 g of N-methyl-N'-methyl-N'-3-pyridylmethylthiourea as a yellow viscous oil. This oily product was purified by silica gel column chromatography using HeOH—CHCl$_3$ (1:10) as an eluent to give crystals.

m.p. : 86–87° C.

NMR (CDCl$_3$) δ: 3.06 (s), 3.17 (d), 5.22 (s), 6.16 (br s), 7.28 (dd. J=8 & 5 Hz, 1 H), 7.74 (m. 1 H), 8.54 (m. 2 H)

(2) In 30 ml of MeOH was dissolved 3.8 g (0.02 mole) of the N-methyl-N'-methyl-N'-3-pyridylmethylthiourea obtained in (1) followed by addition of 2.8 g (0.02 mole) of methyl iodide. The mixture was refluxed for 4 hours. The solvent was distilled off and the residue was diluted with 10 ml or a saturated aqueous solution of sodium hydrogen carbonate and extracted with AcOEt (50 ml×3). The extract was dried over MgSO$_4$ and the solvent was distilled off to give 1.0 g of crude S-methyl-N-methyl-N'-methyl-N'-(3-pyridylmethyl)isothiourea as a yellow oil.

NMR (CDCl$_3$) δ: 2.33 (s), 2.83 (s), 3.26 (s), 4.56 (s), 7.25(dd, J=8 & 5 Hz, 1 H), 7.60 (m, 1 H), 8.55 (m, 2 H)

(3) To 1.0 g (0.048 mole) of the S-methyl-N-methyl-N'-methyl-N'-(3-pyridylmethyl)isothiourea obtained in (2) was added 5 ml of nitromethane and the mixture was stirred at 90° C. for 15 hours. The nitromethane was distilled off and the residue was subjected to silica gel column chromatography using CHCl$_3$-MeOH (5:1) as an eluent to give 0.3 g of the title compound as a yellow viscous oil. This product was cooled (to 5° C.) and the resulting crystals were washed with ethyl acetate and dried. The melting point of this product was 86–87° C.

NMR (CDCl$_3$) δ: 2.83 (s), 3.07 (d), 4.43 (s), 6.53 (s), 7.35 (dd, J-8 & 5 Hz, 1 H), 7.61 (m, 1 H), 8.60 (m, 1 H), 9.73 (br s)

Example 9

1-(6-Chloro-3-pyridylmethyl)amino-1-methylthio-2-nitroethylene (Compound 27)

To 100 ml of EtOH were added 2.4 g (1.5×10$^{-2}$ mole) of 1,1-bis(methylthio)-2-nitroethylene and 1.4 g (9.8×10$^{-3}$ mole) of 6-chloro-3-pyridylmethylamine and the mixture was refluxed for 2 hours. The EtOH was distilled off and the residue was subjected to silica gel column chromatography using CH$_2$Cl$_2$ as an eluent. The procedure gave 1.2 g of the title compound as a pale yellow solid.

NMR (DMSO-d$_6$) δ: 2.48 (s, 3 H), 4.71 (d, J=6.7 Hz, 2 H), 6.66 (br s, 1 H), 7.50 (d, J=8.8 Hz, 1 H), 7.84 (dd, J=8.8 & 2.8 Hz, 1 H), 8.41 (d, J=2.8 Hz, 1 H), 10.0–11.0 (br, 1 H)

Example 10

1-(6-Chloro-3-pyridylmethyl)amino-1-methylamino-2-nitroethylene (Compound 28)

In 100 ml of EtOH was dissolved 1.2 g (4.6×10$^{-3}$ mole) of 1-(6-chloro-3-pyridylmethyl)amino-1-methylthio-2-nitroethylene and on reflux, a solution of 0.84 g of 40% aqueous methylamine in 30 ml EtOH was added dropwise over 1 hour. After cooling, the reaction mixture was concentrated under reduced pressure to about 50 ml and the resulting crystals were collected by filtration and dried to give 0.6 g of the title compound as pale yellow needles.

m.p.: 181–183° C.

NMR (DMSO-d$_6$) δ: 2.6–3.1 (m, 3 H), 4.47 (d, J=6.3 Hz, 2 H), 6.45 (s, 1 H), 7.48 (d, J=8.8 Hz, 1 H), 7.81 (dd, J=8.8 & 2.7 Hz), 8.39 (d, J=2.7 Hz, 1 H), 9.5–10.4 (br, 1 H)

Example 11

1-[N-(6-Chloro-3-pyridylmethyl)-N-methyl]amino-1-methylamino-2-nitroethylene (Compound 29)

(1) Using N-(6-chloro-3-pyridylmethyl)-N-methylamine, the procedure of Example 8 (1) was repeated to give N-(6-chloro-3-pyridylmethyl)-N-methyl-N'-methylthiourea as crystals.

m.p.: 109–110° C.

NMR (CDCl$_3$) δ: 3.06 (s, 3 H), 3.16 (d, J=4.8 Hz, 3 H), 5.22 (s, 2 H), 5.8–6.3 (br, 1 H), 7.30 (d, J=8.6 Hz, 1 H), 7.76 (dd, J=8.6 & 2.7 Hz, 1 H), 8.30 (d, J=2.7 Hz, 1 H)

(2) Using the N-(6-chloro-3-pyridylmethyl)-N-methyl-N'-methylthiourea otained in (1), the procedure of Example 8 (2) was repeated to give S-methyl-N-(6-chloro-3-pyridylmethyl)-N-methyl-N'-methylisothiourea as oil.

NMR (CDCl$_3$) δ: 2.36 (s, 3 H), 2.94 (s, 3 H), 3.27 (s, 3 H), 4.63 (s, 2 H), 7.30 (d, J=8.6 Hz, 1 H), 7.62 (dd, J=8.6 & 2.7 Hz, 1 H), 8.31 (d, J=2.7 Hz, 1 H)

(3) Using the S-methyl-N-(6-chloro-3-pyridylmethyl)-N-methyl-N'-methylisothiourea obtained in (2), the procedure of Example 8 (3) was repeated to give the title compound as crystals.

m.p.: 103–104° C.

NMR (CDCl$_3$) δ: 2.80 (s, 3 H), 3.07 (d, J=4.8 Hz, 3 H), 4.38 (s, 2 H), 6.51 (s, 1 H), 7.37 (d, J=8.6 Hz, 1 H), 7.58 (dd, J=8.6 & 2.7 Hz, 1 H), 8.31 (d, J=2.7 Hz, 1 H), 9.5–9.9 (br, 1 H)

Example 12

1-Methoxy-1-(3-pyridylmethyl)amino-2-nitroethylene (Compound 30)

In one liter of MeOH was dissolved 16.5 g (0.1 mole) of 1,1-bis(methylthio)-2-nitroethylene with heating and on reflux, a solution of 11.0 g (0.1 mole) of 3-pyridylmethylamine in 200 ml of MeOH was added dropwise in 4 installments at 1-hour intervals. The mixture was further refluxed for 3 hours and the MeOH was distilled off. The residue was purified by silica gel column chromatography to give the title compound as white prisms. In this procedure, the compound 1-1 described in Example 1 was also produced as a byproduct.

m.p.: 129–130° C.

NMR (CDCl$_3$) δ: 3.86 (s, OMe), 4.60 (d, CH$_2$N), 6.68 (s, =CHNO$_2$), 10.15 (sbr, NH)

Example 13

1-[N-Ethyl-N-(3-pyridylmethyl)]amino-1-methylamino-2-nitroethylene (Compound 31)

(1) In 50 ml of ethyl ether was dissolved 2.4 g of N-ethyl-N-(3-pyridylmethyl)amine followed by addition of 1.3 g of methyl isothiocyanate. The mixture was stirred at room temperature (25° C.) for 1 hour. The resulting precipitate was collected by filtration, washed with a small amount of ethyl ether and dried to give 3.7 g of N-methyl-N'-ethyl-N'-(3-pyridylmethyl)thiourea as white prisms.

m.p.: 122–123° C.

NMR (CDCl$_3$) δ: 1.16 (t; CH$_2$C<u>H</u>$_3$), 3.16 (d, MeN), 3.55 (q, C<u>H</u>$_2$CH$_3$), 5.12 (s, [pyridyl]—C<u>H</u>$_2$N), 5.95 (br s, NH)

(2) In 30 ml of dry tetrahydrofuran was dissolved 3.1 g of the N-methyl-N'-ethyl-N'-(3-pyridylmethyl)thiourea obtained in (1) followed by addition of 0.6 g of 60% sodium hydride. The mixture was stirred at room temperature (25° C.) for 1 hour. Then, 2.1 g of methyl iodide was added dropwise and the mixture was further stirred for 3 hours. The reaction mixture was concentrated and the residue was diluted with 50 ml of a saturated solution of sodium chloride and extracted 3 times with 50 ml portions of ethyl acetate. The extracts were pooled and dried over MgSO$_4$. The solvent was then distilled off to give 3.1 g of crude S-methyl-N-methyl-N'-ethyl-N'-(3-pyridylmethyl)isothiourea as a yellow oil.

NMR (CDCl$_3$) δ: 1.06 (t, CH$_2$C<u>H</u>$_3$), 2.30 (s, MeS), 3.23 (s, MeN), 3.35 (q, C<u>H</u>$_2$CH$_3$), 4.53 (s, [pyridyl]—C<u>H</u>$_2$)

(3) To 2.2 g of the S-methyl-N-methyl-N'-ethyl-N'-(3-pyridylmethyl)isothiourea obtained in (2) was added 10 ml of nitromethane and the mixture was refluxed for 16 hours. The reaction mixture was concentrated and the residue was subjected to silica gel column chromatography using methanol-chloroform (1:5) as an eluent to give 1.4 g of the title compound as a yellow viscous oil.

NMR (CDCl$_3$) δ: 1.20 (t, CH$_2$C<u>H</u>$_3$), 3.08 (d, MeN), 3.18 (q, C<u>H</u>$_2$CH$_3$), 4.46 (s, [pyridyl]—C<u>H</u>$_2$), 6.53

Example 14

1-[N-(2-Dimethoxyethyl)-N-(3-pyridylmethyl) amino-1-methylamino-2-nitroethylene (Compound 32)

Using N-(2-dimethoxyethyl)-N-(3-pyridylmethyl)amine in lieu of N-ethyl-N-(3-pyridylmethyl)amine, the steps (1), (2) and (3) of Example 13 were carried out to give the following compounds at the respective steps.

(1) N-Methyl-N'-(2-dimethoxyethyl)-N'-(3-pyridymethyl)-thiourea (pale yellow viscous oil)

NMR (CDCl$_3$) δ: 3.13 (d, MeN), 3.37 (s, MeO), 3.53 (d, NC<u>H</u>$_2$CH), 4.30 (t, CH$_2$C<u>H</u>), 5.22 (s,

-continued

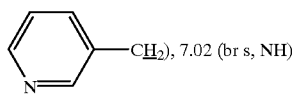), 7.02 (br s, NH)

(2) S-Methyl-N-methyl-N'-(2-dimethoxyethyl)-N'-(3-pyridylmethyl)isothiourea (yellow oil)

NMR (CDCl₃) δ: 2.26 (s, MeS), 3.24

(s, MeN), 3.35 (s, MeO), 3.46 (d, C$\underline{H}$₂CH), 4.48 (t, CH₂C$\underline{H}$), 4.69 (s, 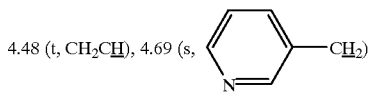)

(3) Title compound (yellow viscous oil)

NMR (CDCl₃) δ: 1.20 (t, CH₂C$\underline{H}$₃), 3.08 (d, MeN), 3.18 (q, C$\underline{H}$₂CH₃), 4.46 (s, 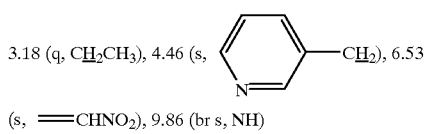), 6.53

(s, =CHNO₂), 9.86 (br s, NH)

Example 15

1-Ethylamino-1-[N-methyl-N-(3-pyridylmethy)]amino-2-nitroethylene (compound 33)

The steps (1), (2) and (3) of Example 13 were repeated except that N-methyl-N-(3-pyridylmethyl)amine and ethyl isothiocyanate were used in lieu of N-ethyl-N-(3-pyridylmethyl)amine and methyl isothiocynate, respectively; to give the following compounds in the respective steps.

(1) N-ethyl-N'-methyl-N'-(3-pyridylmethyl)thiourea
m.p.: 110–111° C.

NMR (CDCl₃) δ: 1.23 (3 H, t, J=7.5 Hz), 3.05 (3 H, s), 3.5–3.9 (2 H, m), 5.20 (2 H, s), 5.8–6.2 (1 H, br), 7.26 (1 H, dd, J=8.4 & 5.4 Hz), 7.72 (1 H, dt, J=8.4 & 1.5 Hz), 8.4–8.6 (2 H, m) IR (Nujol): 3180 cm⁻¹

(2) S-Methyl-N-ethyl-N'-methyl-N'-(3-pyridylmethyl)isothiourea (yellow oil)

NMR (CDCl₃) δ: 1.16 (3 H, t, J=7.5 Hz), 2.36 (3 H, s), 2.93 (3 H, s), 3.56 (2 H, q, J=7.5 Hz), 4.64 (2 H, s), 7.26 (1 H, dd, J=8.4 & 5.4 Hz), 7.63 (1 H, dt, J=8.4 & 1.5 Hz), 8.4–8.6 (2 H, m)

(3) Title compound (viscous oil)

NMR (CDCl₃) δ: 1.34 (3 H, t, J=7.5 Hz), 2.82 (3 H, s), 3.1–3.6 (2 H, m), 4.43 (2 H, s), 6.52 (1 H, s), 7.32 (1 H, dd, J=8.4 & 5.4 Hz), 7.58 (1 H, dt, J=8.4 & 1.5 Hz), 8.4–8.7 (2 H, m), 9.3–9.8 (1 H, br) IR (neat): 3220 cm⁻¹

Example 16

1-n-Butylamino-1-[N-methyl-N-(3-pyridylmethyl)]-amino-2-nitroethylene (Compound 34)

The steps (1), (2) and (3) of Example 13 were repeated except that N-methyl-N-(3-pyridylmethyl)amine and n-butyl isothiocyanate were used in lieu of N-ethyl-N-(3-pyridylmethyl)amine and methyl isothiocyanate, respectively, to give the following compounds in the respective steps.

(1) N-n-Butyl-N'-methyl-N'-(3-pyridylmethyl)thiourea (pale yellow oil)

NMR (CDCl₃) δ: 0.93 (3 H, t, J=7.8 Hz), 1.2–1.9 (4 H, m), 3.06 (3 H, s), 3.4–3.9 (2 H, m), 5.21 (2 H, s), 5.5–6.1 (1 H, br), 7.28 (1 H, dd, J=8.4 & 5.4 Hz), 7.74 (1 H, dt, J=8.4 & 1.5 Hz), 8.4–8.7 (2 H, m) IR (neat): 3270 cm⁻¹

(2) S-Methyl-N-n-butyl-N'-methyl-N'-(3-pyridylmethyl)-isothiourea (yellow oil)

NMR (CDCl₃) δ: 0.90 (3 H, t, J=7.8 Hz), 1.1–1.9 (4 H, m), 2.30 (3 H, s), 2.85 (3 H, s), 3.49 (2 H, t, J=6.8 Hz), 4.56 (2 H, s), 7.23 (1 H, dd, J=8.4 & 5.4 Hz), 7.60 (1 H, dt, J=8.4 & 1.5 Hz), 8.4–8.6 (2 H, m)

(3) Title compound (viscous oil)

NMR (CDCl₃) δ: 0.94 (3 H, t, J=7.8 Hz), 1.2–1.9 (4 H, m), 2.80 (3 H, s), 3.34 (2 H, m), 4.42 (2 H, s), 6.54 (1 H, s), 7.34 (1 H, dd, J=8.4 & 5.4 Hz), 7.58 (1 H, dt, J=8.4 & 1.5 Hz), 8.4–8.7 (2 H, m), 9.4–9.9 (1 H, br) IR (neat): 3210 cm⁻¹

Example 17

1-Methylamino-1-[N-(2-methoxyethyl)-N-(3-pyridyl-methyl)]amino-2-nitroethylene (Compound 35)

The steps (1), (2) and (3) of Example 13 were repeated except that N-(2-methoxyethyl)-N-(3-pyridyl-methyl)amine was used in lieu of N-ethyl-N-(3-pyridyl-methyl)amine to give the following compounds in the respective steps.

(1) N-Methyl-N'-(2-methoxyethyl)-N'-(3-pyridylmethyl)-thiourea (colorless viscous oil)

NMR (CDCl₃) δ: 3.33 (s, MeO), 3.50 (m, CH₂CH₂), 5.20 (s, 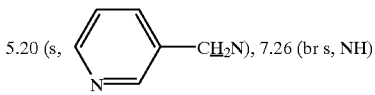—C$\underline{H}$₂N), 7.26 (br s, NH)

(2) S-Methyl-N-methyl-N'-(2-methoxyethyl)-N'-(3-pyridyl-methyl)isothiourea (oil)

NMR (CDCl₃) δ: 2.27 (s, MeS), 3.23 (s, MeN), 3.30

(s, MeO), 3.52 (m, CH₂CH₂), 4.66 (s, 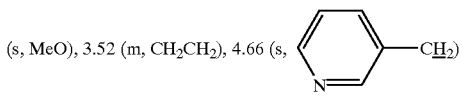—C$\underline{H}$₂)

(3) Title compound (yellow viscous oil)

NMR (CDCl₃) δ: 3.06 (d, MeN), 3.35 (s, MeO), 3.43

(m, CH₂CH₂), 4.53 (s, —C$\underline{H}$₂N), 6.55 (s,

=CHNO₂), 9.10 (br s, NH)

Example 18

1-Allylamino-1-[N-methyl-N-(3-pyridylmethyl)]amino-2-nitroethylene (Compound 36)

The steps (1), (2) and (3) of Example 13 were repeated except that N-methyl-N-(3-pyridylmethyl)amine and allyl isothiocyanate were used in lieu of N-ethyl-N-(3-pyridylmethyl)amine and methyl isothiocyanate, respectively, to give the following compounds in the respective steps.

(1) N-Allyl-N'-methyl-N'-(3-pyridylmethyl)thiourea
m.p.: 82–84° C.

NMR (CDCl$_3$) δ: 3.07 (3 H, s), 4.34 (2 H, m), 5.0–5.4 (2 H, m), 5.21 (2 H, s), 5.6–6.3 (2 H, m), 7.27 (1 H, dd, J=8.4 & 5.4 Hz), 7.73 (1 H, dt, J=8.4 & 1.5 Hz), 8.4–8.6 (2 H, m) IR (Nujol): 3280 cm$^{-1}$ (2) S-Methyl-N-allyl-N'-methyl-N'-(3-pyridylmethyl) isothiourea (yellow oil)

NMR (CDCl$_3$) δ: 2.30 (3 H, s), 2.90 (3 H, s), 4.1–4.3 (2 H, m), 4.62 (2 H, s), 4.9–5.3 (2 H, m), 5.7–6.3 (1 H, m), 7.26 (1 H, dd, J=8.4 & 5.4 Hz), 7.62 (1 H, dt, J=8.4 & 1.5 Hz), 8.4–8.7 (2 H, m)

(3) Title compound (oil)

NMR (CDCl$_3$) δ: 2.81 (3 H, s), 3.9–4.2 (2 H, m), 4.43 (2 H, s), 5.1–5.6 (2 H, m), 5.7–6.2 (1 H, m), 6.55 (1 H, s), 7.35 (1 H, dd, J=8.4 & 5.1 Hz), 7.60 (1 H, dt, J=8.4 & 1.5 Hz), 8.4–8.7 (2 H, m), 9.4–9.9 (1 H, br)

Example 19

1-iso-Propylamino-1-(N-methyl-N-(3-pyridylmethyl)]-amino-2-nitroethylene
(Compound 37)

The steps (1), (2) and (3) of Example 13 were repeated except that N-methyl-N-(3-pyridylmethyl)amine and isopropyl isothiocyanate were used in lieu of N-ethyl-N-(3-pyridylmethyl)amine and methyl isothiocyanate, respectively, to give the following compounds in the respective steps.

(1) N-iso-Propyl-N'-methyl-N'-(3-pyridylmethyl)thiourea
m.p.: 135–136° C.

NMR (CDCl$_3$) δ: 1.26 (6 H, d, J=6.3 Hz), 3.03 (3 H, s), 4.4–4.9 (1 H, m), 5.21 (2 H, s), 5.0–5.5 (1 H, br), 7.27 (1 H, dd, J=8.4 & 5.1 Hz), 7.74 (1 H, dt, J=8.4 & 1.5 Hz), 8.4–8.7 (2 H, m) IR (Nujol): 3200 cm$^{-1}$ (2) S-Methyl-N-iso-propyl-N'-methyl-N'-(3-pyridylmethyl)-isothiourea (oil)

NMR (CDCl$_3$) δ: 1.07 (6 H, d, J=6.3 Hz), 2.30 (3 H, s), 2.84 (3 H, s), 3.6–4.1 (1 H, m), 4.50 (2 H, s), 7.23 (1 H, dd, J=8.4 & 5.1 Hz), 7.61 (1 H, dt, J=8.4 & 1.5 Hz), 8.4–8.6 (2 H, m)

(3) Title compound
m.p.: 119–121° C.

NMR (CDCl$_3$) δ: 1.31 (6 H, d, J=6.6 Hz), 2.83 (3 H, s), 3.5–4.0 (1 H, m), 4.44 (2 H, s), 6.52 (1 H, s), 7.33 (1 H, dd, J=8.4 & 5.1 Hz), 7.57 (1 H, dt, J=8.4 & 1.5 Hz), 8.4–8.7 (2 H, m), 8.9–9.4 (1 H, br d, J=9.6 Hz) IR (Nujol): 3080 cm$^{-1}$ Example 20

1-Benzylamino-1-[N-methyl-N-(3-pyridylimethyl)]amino-2-nitroethylene (Compound 38)

The steps (1), (2) and (3) of Example 13 were repeated except that N-methyl-N-(3-pyridylmethyl)amine and benzyl isothiocyanate were used in lieu of N-ethyl-N-(3-pyridylmethyl)amine and methyl isothiocyanate, respectively, to give the following compounds in the respective steps.

(1) N-Benzyl-N'-methyl-N'-(3-pyridylmethyl)thiourea (pale yellow oil)

NMR (CDCl$_3$) δ: 3.03 (3 H, s), 4.90 (2 H, d, J=5.1 Hz), 5.21 (2 H, s), 6.10 (1 H, br), 7.1–7.5 (6 H, m), 7.74 (1 H, dt, J=8.4 & 1.5 Hz), 8.4–8.6 (2 H, m) IR (neat): 3250 cm$^{-1}$ (2) S-Methyl-N-benzyl-N'-methyl-N'-(3-pyridylmethyl) isothiourea (oil)

NMR (CDCl$_3$) δ: 2.29 (3 H, s), 2.92 (3 H, s), 4.62 (2 H, s), 4.77 (2 H, s), 7.1–7.5 (6 H, m), 7.59 (1 H, dt, J=8.4 & 1.5 Hz), 8.4–8.7 (2 H, m)

(3) Title compound (oil)

NMR (CDCl$_3$) δ: 2.78 (3 H, s), 4.36 (2 H, s), 4.53 (2 H, d, J=6.0 Hz), 6.56 (1 H, s), 7.1–7.5 (7 H, m), 8.3=8.5 (1 H, m), 8.57 (1 H, dd, J=5.2 & 1.5 Hz), 9.7–10.2 (1 H, br)

Example 21

1-Methylamino-1- [N-methyl-N-(3-quinolylmethyl)]-amino-2-nitroethylene
(Compound 39)

The steps (1), (2) and (3) of Example 13 were repeated except that N-methyl-N-(3-quinolylmethyl)amine was used in lieu of N-ethyl-N-(3-pyridylmethyl)amine to give the following compounds in the respective steps.

(1) N-Methyl-N'-methyl-N'-(3-quinolylmethyl)thiourea
m.p.: 138–139° C.

NMR (CDCl$_3$) δ: 3.09 (s, MeNCH$_2$), 3.18 (d, J=5 Hz, MeNH), 5.35 (s, NCH$_2$), 6.00 (br, NH), 7.4–7.9 (m, 3 H, quinoline-H$_3$), 8.0–8.2 (m, 2 H, quinoline-H$_2$), 8.33 (d, J=2 Hz, 1 H, quinoline-H$_1$) IR (Nujol): 3200, 1545, 1530, 1495, 1445, 1375, 1335, 1240, 1050 cm$^{-1}$ (2) S-Metyl-N-metyl-N'-methyl-N'-(3-quinolylethyl) isothiourea (oil)

NMR (CDCl$_3$) δ: 2.33 (s, MeS), 2.89 (s, MeNCH$_2$), 3.28 (s, MeN=), 4.73 (s, NCH$_2$), 7.2–7.9 (m, 3 H, quinoline-H$_3$) 7.9–8.2 (m, 2 H, quinoline-H$_2$), 8.85 (d, J=2 Hz, 1 H, quinoline-H$_1$) IR (neat): 1600, 1490, 1370, 1340, 1060, 1020, 755 cm$^{-1}$ (3) Title compound
m.p.: 145–157° C.

NMR (CDCl$_3$) δ: 2.85 (s, MeNCH$_2$), 3.08 (d, J=6 Hz, MeNH), 4.58 (s, NCH$_2$), 6.59 (s, =CHNO$_2$), 7.5–7.95 (m, 3 H, quinoline-H$_3$), 7.95–8.25 1010 (m, 2 H, quinoline-H$_2$), 8.81 (d, J=2 Hz, 1 H, quinoline-H$_1$), 9.80 (br, NH) IR (Nujol): 1590, 1545, 1405, 1310, 1280, 1230 cm$^{-1}$ Example 22

1-Metylamino-1-[N-methyl-N-[1-(3-pyridyl)ethyl]]-amino-2-nitroethylene (Compound 40)

The steps (1), (2) and (3) of Example 13 were repeated except that N-methyl-N-[1-(3-pyridyl)ethyl]amine was used in lieu of N-ethyl-N-(3-pyridylmethyl)amine to give the following compounds in the respective steps.

(1) N-Methyl-N'-methyl-N'-[1-(3-pyridyl)ethyl]thiourea (pale yellow viscous oil)

NMR CDCl$_3$) δ: 1.56 (d, J=7 Hz, MeCH), 2.76 (s, MeNCH$_2$), 3.18 (d, J=5 Hz, MeNH), 6.30 (br, NH), 7.04 (q, J=7 Hz, MeCH), 7.28 (dd, J=7 and 5 Hz, 1 H, pyridine-H$_1$), 7.70 (m, 1 H pyridine-H$_1$), 8.5 (m, 2 H, pyridine-H$_2$) IR (neat): 3270, 1550 (sh.), 1530, 1480, 1420, 1375, 1340, 1295 cm$^{-1}$ (2) S-Methyl-N-methyl-N'-methyl-N'-[1-(3-pyridyl)-ethyl]thiourea (oil)

NMR (CDCL$_3$) δ: 1.54 (d, J=7 Hz, MeCH), 2.31 (s, MeS), 2.63 (s, MeNCH$_2$), 3.27 (s, MeN=), 5.66 (q, J=7 Hz, MeCH), 7.24 (dd, J=5 & 8 Hz, 1 H, pyridine-H$_1$), 7.62 (m, 1 H, pyridine-H$_1$), 8.48 (dd, J=5 & 2 Hz, 1 H, pyridine-H$_1$), 8.59 (d, J=2 Hz, 1 H, pyridine-H$_1$) IR (neat): 2910, 1600, 1415, 1390, 1370, 1235, 1070, 1010, 71.0 cm$^{-1}$ (3) Title compound (viscous oil)

NMR (CDCl$_3$) δ: 1.70 (d, J=7 Hz, MeCH), 2.63 (s, MeN), 3.02 (d, j=5 Hz, MeNH), 4.93 (q, J=7 Hz, MeCH), 6.50 (s, =CHNO$_2$), 7.33 (dd, J=5 & 8 Hz, 1 H, pyridine-H$_1$), 7.60 (m, 1 H, pyridine-H$_2$), 8.6 (m, 2 H, pyridine-H$_2$), 9.77 (br, NH) IR (neat): 1585, 1420, 1400, 1340, 1240, 1020, 750 cm$^{-1}$ Example 23

1-[2,2-Dimethyl-1-(3-pyridylmethyl)]hydrazino-1-methylamino-2-nitroethylene (Compound 41)

(1) In 30 ml of toluene was dissolved 2.5 g of 1,1-dimethyl-2-(3-pyridylmethyl)hydrazine followed by addition of 1.2 g of methyl isothiocyanate and the mixture was refluxed for 1 hour. The reaction mixture was concentrated and the resulting crystals are collected by filtration, washed with ethyl ether and dried. The procedure gave 2.6 g of 1,1-dimethyl-4-methyl-2-(3-pyridylmethyl) thiosemicarbazide as white prisms.

m.p.: 101–102° C.

NMR (CDCl$_3$) δ: 2.45 (s, Me$_2$N), 3.17 (d, J=5 Hz, MeNH), 5.28 (s, CH$_2$N), 7.20 (dd, J=8 and 5 Hz, 1 H, pyridine-H$_1$), 7.89 (m, 1 H, pyridine-H$_1$), 8.10 (br, NH), 8.50 (dd, J=5 & 2 Hz, 1 H, pyridine-H$_1$), 8.62 (d, J=2 Hz, 1 H, pyridine-H$_1$) IR (Nujol): 3200, 1514, 1420, 1370, 1320, 975 cm$^{-1}$ (2) 0.52 g of 60% sodium hydride was washed with petroleum ether and suspended in 20 ml of dry tetrahydrofuran, followed by addition of 2.9 g of 1,1-dimethyl-4-methyl-2-(3-pyridylmethyl)thiosemicarbazide as prepared according to (1). The mixture was stirred at 50° C. for 2 hours. After cooling and addition of 1.8 g of methyl iodide, the mixture was stirred at room temperature (25° C.) for 2 hours and, then, concentrated. To the residue was added 50 ml of ethyl acetate and the insoluble matter was filtered off. The filtrate was dried over MgSO$_4$ and concentrated to give 2.2 g of S-methyl-1,1-dimethyl-4-methyl-2-(pyridylmethyl)isothiosemicarbazide as oil.

NMR (CDCl$_3$) δ: 2.41 (s, MeS), 2.60 (s, Me$_2$N), 3.06 (s, MeN), 4.30 (s, CH$_2$N), 7.18 (dd, J=5 & 8 Hz, 1 H, pyridine-H$_1$), 7.60 (m, 1 H, pyridine-H$_1$), 8.10 (dd, J=5 & 2 Hz, 1 H, pyridine-H$_1$), 8.21 (d, J=2 Hz, pyridine-H$_1$) IR (neat): 1600, 1420, 1240, 1020, 710 cm$^{-1}$ (3) To 2.2 g of S-methyl-1,1-dimethyl-4-methyl-2-(pyridylmethyl)isothiosemicarbazide prepared in (2) was added 10 ml of nitromethane and the mixture was refluxed for 7 hours. The reaction mixture was concentrated and subjected to silica gel column chromatography using chloroform-methanol (5:1) as an eluent. The procedure gave 1.0 g of the title compound as yellow prisms.

m.p.: 109–110° C.

NMR (CDCl$_3$) δ: 2.62 (s, Me$_2$N), 3.16 (d, J=6 Hz, MeN), 4.43 (s, CH$_2$N), 6.43 (s, =CHNO$_2$), 7.27 (dd, J=8 & 5 Hz, 1 H, pyridine-H$_1$), 7.60 (m, 1 H, pyridine-H), 8.5–8.65 (m, 2 H, pyridine-H$_2$), 10.1 (br, NH) IR (Nujol): 1585, 1405, 1340, 1315, 1235 cm$^{-1}$ Example 24

1-Methylamino-1-[N-(n-propyl)-N-(3-pyridylmethyl)]amino-2-nitroethylene (Compound 42)

The steps (1), (2) and (3) of Example 13 were repeated except that N-n-propyl-N-(3-pyridylmethyl)amine was used in lieu of N-ethyl-N-(3-pyridylmethyl)amine to give the following compounds in the respective stems.

(1) N-Methyl-N'-(n-propyl)-N'-(3-pyridylmethyl)thiourea (pale yellow viscous oil)

NMR (CDCl$_3$) δ: 0.90 (t), 1.4–1.9 (m), 3.16 (d, MeN), 3.42 (t), 5.15 (s), 5.87 (br s, NH), 7.26 (dd), 7.74 (dt), 8.46–8.60 (m, 2 H) IR (neat): 3270, 1525, 1340, 1235, 1020, 710 cm$^{-1}$ (2) S-Methyl-N-methyl-N'-(n-propyl)-N'-(3-pyridylmethyl)isothiourea (yellow oil)

NMR (CDCl$_3$) δ: 0.84 (t), 1.33–1.80 (m), 2.29 (s, MeS), 3.23 (s, MeN), 3.26 (t), 4.55 (s), 7.22 (dd), 7.56 (dt), 8.43–8.60 (m, 2 H) IR (neat): 1600, 1425, 1210, 715 cm$^{-1}$ (3) Title compound (yellow viscous oil)

NMR (CDCl$_3$) δ: 0.86 (t), 1.40–1.90 (m, 2 H), 2.95–3.30 (m, 2 H), 3.05 (d, MeN), 4.53 (s, 2 H), 6.55 (s, =CHNO$_2$), 7.34 (dd), 7.66 (dt), 8.43–8.66 (m, 2 H), 9.56 (br d, NH)

Example 25

1-[N-(n-Butyl-N-(3-pyridyl)]amino-1-methylamino-2-nitroethylene (Compound 43)

The steps (1), (2) and (3) of Example 13 were repeated except that N-(n-butyl)-N-(3-pyridylmethyl)amine was used in lieu of N-ethyl-N-(3-pyridylmethyl)amine to give the following compounds in the respective steps.

(1) N-(n-Butyl)-N-(3-pyridylmethyl)-N'-methylthiourea (pale yellow viscous oil)

NMR (CDCl$_3$) δ: 0.90 (t), 1.1–1.8 (m, 4 H), 3.15 (d, MeN), 3.30–3.56 (m), 5.13 (s), 5.82 (br s, NH), 7.25 (dd), 7.73 (dt), 8.43–8.60 (m, 2 H) IR (neat) 3280, 1525, 1345, 1230, 1030, 710 cm$^{-1}$ (2) S-Methyl-N-methyl-N'-(n-butyl)-N'-(3-pyridylmethyl-isothiourea (yellow oil)

NMR (CDCl$_3$) δ: 0.86 (t), 1.03–1.70 (m, 4 H), 2.28 (s, MeS), 3.23 (s, MeN), 3.30 (t), 4.54 (s), 7.22 (dd), 7.56 (dt), 8.40–8.56 (m, 2 H) IR (neat): 1605, 1425, 1190, 1020, 715 cm$^{-1}$ (3) Title compound (viscous oil)

NMR (CDCl$_3$) δ: 0.90 (t), 1.06–1.80 (m, 4 H), 2.96–3.23 (m, 2 H), 3.07 (d, MeN), 4.40 (s), 6.56 (s, =CHNO$_2$), 7.33 (dd), 7.60 (dt), 8.46–8.66 (m, 2 H), 9.82 (br d, NH)

Example 26

1-[N-Benzyl-N-(3-pyridylmethyl)amino-1-methyl-amino-2-nitroethylene (Compound 44)

The steps (1), (2) and (3) of Example 13 were repeated except that N-benzyl-N-(3-pyridylmethyl)amine was used in lieu of N-ethyl-N-(3-pyridylmethyl)amine to give the following compounds in the respective steps.

(1) N-Benzyl-N-(3-pyridylmethyl)-N'-methylthiourea m.p.: 141–143° C. (white prisms)

(2) S-Methyl-N-methyl-N'-benzyl-N'-(3-pyridylmethyl)-isothiourea (yellow oil)

NMR (CDCl$_3$) δ: 2.32 (s, MeS), 3.26 (s, MeN), 4.45 (s), 4.52 (s), 7.06–7.36 (m, 6 H), 7.50 (dt), 8.36–8.53 (m, 2 H) IR (neat): 1600, 1425, 1180, 1020, 700 cm$^{-1}$ (3) Title compound m.p.: 118–119° C. (pale yellow scales)

NMR (CDCl$_3$) δ: 3.16 (d, J=5 Hz, MeN), 4.22 (s, CH$_2$ and CH$_2$), 6.53 (s, =CHNO$_2$), 7.06–7.60 (m, 7 H), 8.40 (br s), 8.60 (br d), 9.76 (br d, J=5 Hz, NH) IR (Nujol): 1590, 1520, 1450, 1360, 1280 cm$^{-1}$ Example 27

1-Amino-1-[N-(6-chloro-3-pyridylmethyl)-N-methyl]-amino-2-nitroethylene (Compound 45)

(1) In 200 ml of EtOH was dissolved 5.0 g of 1,1-bis-(methylthio)-2-nitroethylene with heating and a solution containing 4.7 g of N-(6-chloro-3-pyridylmethyl)-N-methylamine in 50 ml of EtOH was added dropwise on reflux in 3 portions at 30-minute intervals. After completion of dropwise addition, the mixture was further refluxed for 3 hours and the EtCH was then distilled off. The residue was subjected to silica gel column chromatography using CHCl$_3$—MeOH (20:1) as an eluent. The procedure gave 3.5 g of 1-[N-(6-chloro-3-pyridylmethyl)-N-methyl]amino-1-methylthio-2-nitroethylene as a yellow viscous oil.

NMR (CDCl$_3$) δ: 2.46 (s, MeS), 3.03 (s, MeN), 4.76 (s, CH$_2$), 6.76 (s, =CHNO$_2$), 7.35 (d), 7.60 (dd), 8.30 (d) IR (neat): 1750, 1540, 1260, 1100, 1020 cm$^{-1}$ (2) In 20 ml of MeOH was dissolved 1.1 g of 1-[N-(6-chloro-3-pyridylmethyl)-N-methyl]amino-1-methylthio-2-nitroethylene prepared in (1), followed by addition of 1.0 ml of 25% aqueous ammonia, and the mixture was stirred at room temperature for 1 hour. The resulting crystals were collected by filtration, washed with a small amount of MeOH and dried to give 0.85 g of the title compound as pale yellow scales.

m.p.: 206–207° C.

NMR (DMSO-d$_6$) δ: 3.03 (s, MeN), 4.65 (s, CH$_2$), 6.60 (s, =CHNO$_2$), 7.45 (d), 7.68 (dd), 8.31 (d), 8.92 (br s, NH$_2$) IR (Nujol): 3280, 3140, 1625, 1580, 1420, 1225 cm$^{-1}$ Example 28

1-(6-Chloro-3-pyridylmethyl)amino-1-dimethylamino-2-nitroethylene (Compound 46)

(1) In 50 ml of EtOH was dissolved 3.3 g of 1,1-bis-(methylthio)-2-nitroethylene and 2.2 ml of a 40% aqueous solution of dimethylamine was added dropwise in 2 portions at 30-minute intervals under refluxing. After completion of dropwise addition, the mixture was further refluxed for 30 minutes. Then, the EtOH was distilled off and the residue was subjected to silica gel column chromatography using CHCl$_3$-MeOH (20:1) as an eluent. The procedure gave 1.0 g of 1-dimethylamino-1-methylthio-2-nitroethylene as a yellow oil.

NMR (CDCl$_3$) δ: 2.46 (s, 3 H), 3.21 (s, 6 H), 6.69 (s, 1 H)

(2) The 1-dimethylamino-1-methylthio-2-nitroethylene (1.0 g) prepared in (1) and 1.0 g of 6-chloro-3-pyridylmethylamine were refluxed in 30 ml of EtOH for 2 hours. The EtOH was then distilled off and the residue was subjected to silica gel column chromatography using CHCl$_3$—MeOH (10:1) as an eluent. The crystals obtained were recrystallized from EtOH to recover 0.82 g of the title compound as pale yellow crystals.

m.p.: 124–125° C.

NMR (CDCl$_3$) δ: 2.99 (s, 6 H), 4.53 (d, J=5.4 Hz, 2 H), 6.46 (s, 1 H), 7.34 (d, J=8.4 Hz, 1 H), 7.72 (dd, J=8.4 & 2.4 Hz, 1 H), 8.35 (d, J=2.4 Hz, 1 H), 9.2–9.8 (br, 1 H) IR (Nujol): 1585, 1440, 1380, 1260 cm$^{-1}$ Example 29

1-(2,6-Dichloro-3-pyridylmethyl) amino-1-methylamino-2-nitroethylene (Compound 47)

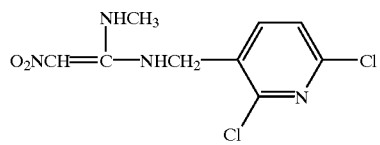

A mixture of 1.2 g (0.007 mole) of (2,6-dichloro-3-pyridylmethyl)amine and 1 sg (0.007 mole) of 1-methyl-amino-1-methylthio-2-nitroethane was refluxed in 50 ml of EtOH for 6 hours. After cooling, the reaction mixture was concentrated and the resulting crystals were collected by filtration, washed with CH$_2$Cl$_2$ and a small amount of EtOH in that order and dried. The procedure gave 0.53 g of the title compound as a white powder.

m.p.: 211–213° C. (decompn.)

NMR (DMSO-d$_6$) δ: 2.83 (br, 3 H), 4.50 (br d, 2 H), 6.43 (s, 1 H), 7.58 (d, J=8.5 Hz), 7.80 (d, J=8.5 Hz), 7.0–7.93 (br, NH), 9.50–10.50 (br, NH) IR (Nujol): 3170, 1630, 1580, 1375, 1210 cm$^{-1}$ Example 30

1-Amino-1-[N-(2,6-dichloro-3-pyridylmethyl)-N-methyl]amino-2-nitroethylene (Compound 48)

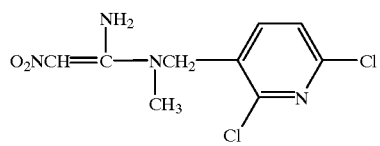

In 30 ml of MeOH was dissolved 0.9 g (0.003 g mole) of 1-[N-(2,6-dichloro-3-pyridylmethyl)-N-methyl]-amino-1-methylthio-2-nitroethylene, followed by addition of 0.6 ml (0.0045 mole) of 25% aoueous ammonia at 50° C., and the mixture was stirred at the same temperature for 1 hour. After cooling, the reaction mixture was concentrated and the resulting crystals were collected by filtration, washed with a small amount of EtOH and dried. The procedure gave 0.7 g of the title compound as a white powder.

m.p.: 214–215° C. (decompn.)

NMR (DMSO-d$_6$) δ: 3.05 (s, 3 H), 4.63 (s, 2 H), 6.56 (s, 1 H), 7.46–7.70 (m, 2 H), 8.90 (br s, NH$_2$) IR (Nujol): 3350, 1610, 1565, 1410, 1290, 1220 cm$^{-1}$ Example 31

1-Amino-1-[N-(6-chloro-3-pyridylmethyl)-N-i-propyl]amino-2-nitroethylene (Compound 49)

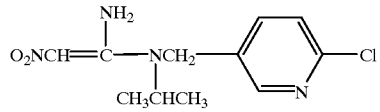

In 8 ml or EtOH was dissolved 0.59 g (0.00196 mole) of 1-[N-(6-chloro-3-pyridylmethyl)-N-i-propyl]-amino-1-methylthio-2-nitroethylene, followed by addition of 0.20 ml of 25% aqueous ammonia. The mixture was stirred at room temperature for 2 hours and 40 minutes. The reaction mixture was concentrated and the residue was subjected to silica gel (100 g) column chromatography using MeOH—

CHCl₃ (1:7) as an eluent to give the title compound as oil. The oil was triturated with Et₂O and the resulting powder was collected by filtration, washed with Et₂O and dried. The procedure gave 0.19 g of the title compound.

NMR (DMSO-d₆) δ: 1.13 (d, J=7 Hz, Me₂CH), 4.30 (septet, J=7 Hz, Me₂CH), 4.62 (s, CH₂), 6.50 (s, =CHNO₂), 7.49 (d, J=8 Hz, 1 H), 7.69 (dd, J=8 & 2 Hz, 1 H), 8.30 (d, J=2 Hz, 1 H), 9.04 (br, NH₂) IR (Nujol): 1610, 1540, 1280, 1230, 1100 cm⁻¹

Example 32

1-(6-Chloro-3-pyridylmethyl)amino-1-(N-ethyl-N-methyl)amino-2-nitroethylene (Compound 50)

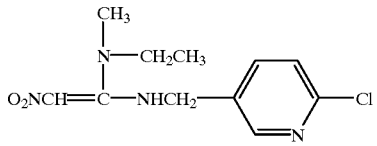

The step (2) of Example 28 was repeated excent that 1-(N-ethyl-N-methyl)amino-1-methylthio-2-nitroethylene was used in lieu of 1-dimethylamino-1-methylthio-2-nitroethylene to give the title compound as pale yellow crystals.

m.p.: 87–88° C.

NMR (CDCl₃) δ: 1.18 (t, J=6.5 Hz, 3 H), 2.89 (s, 3 H), 3.23 (q, J=6.5 Hz, 2 H), 4.46 (d, J=5.7 Hz, 2 H), 6.53 (s, 1 H), 7.34 (d, J=8.4 Hz, 1 H), 7.69 (dd, J=8.4 & 2.4 Hz, 1 H), 8.33 (d, J=2.4 Hz, 1 H), 9.5–10.0 (br, 1 H) IR (Nujol): 1600, 1460 cm⁻¹

Example 33

1-(6-Chloro-3-pyridylmethyl)amino-1-hydrazino-2-nitroethylene (Compound 51)

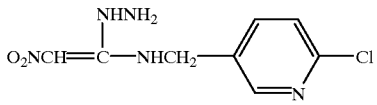

The reaction procedure of Example 3 was repeated except that 1-(6-chloro-3-pyridylmethyl)amino-1-methylthio-2-nitroethylene and hydrazine hydrate were used in lieu of 1-methylthio-1-(3-pyridylmethyl)amino-2-nitroethylene and aqueous methylamine solution, respectively. The procedure gave the title compound as pale yellow crystals.

m.p.: 188–190° C. (decompn.)

NMR (DMSO-d₆) δ: 4.43 (br s, 2 H), 4.3–5.2 (br, 2 H), 6.49 (s, 1 H), 7.50 (d, J=8.4 Hz, 1 H), 7.81 (dd, J=8.4 & 2.4 Hz, 1 H), 8.39 (d, J=2.4 Hz, 1 H), 9.9–10.8 (br, 1 H) IR (Nujol): 3260, 1650, 1560, 1450 cm⁻¹

Example 34

1-(6-Chloro-3-pyridylmethyl)amino-1-(2,2-dimethyl-1-hydrazino)-2-nitroethylene (Compound 52)

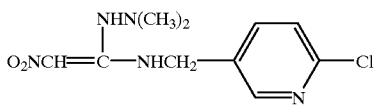

The reaction procedure of Example 6 was repeated except that 6-chloro-3-pyridylmethylamine was used in lieu of 3-pyridylmethylamine to give the title compound as pale brown prisms.

m.p.: 170–172° C.

NMR (DMSO-D₆) δ: 2.59 (S, 6 H), 4.43 (d, J=6.6 Hz, 2 H), 6.2–6.7 (br, 1 H), 7.47 (d, J=8.4 Hz, 1 H), 7.79 (dd, J=8.4 & 2.4 Hz, 1 H), 8.38 (d, J=2.4 Hz, 1 H), 8.0–8.5 (br, 1 H), 9.9–10.5 (br, 1 H) IR (Nujol): 3200, 1590, 1560, 1460, 1390, 1350 cm⁻¹

Example 35

1-(6-Chloro-3-pyridylmethyl)amino-1-(2-methoxycarbonyl)hydrazino-2-nitroethylene (Compound 53)

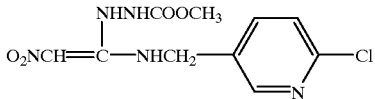

To a solution of 0.4 g (0.0016 mole) of 1-(6-chloro-3-pyridylmethyl)amino-1-hydrazino-2-nitroethylene in 15 ml of DMF was added 0.14 ml (0.0018 mole) of methyl chloroformate and the mixture was stirred at room temperature for 30 minutes. The DMF was distilled off under reduced pressure and the residue was subjected to silica gel column chromatography using EtOH—CHCl₃ (1:7) as an eluent. The procedure gave 0.14 g of the title compound as a pale yellow solid.

m.p.: 198–201° C. (decompn.)

NMR (DMSO-d₆) δ: 3.67 (s, 3 H), 4.48 (br d, J=6 Hz, 2 H), 6.43 (s, 1 H), 7.52 (d, J=8.4 Hz, 1 H), 7.80 (dd, J=8.4 & 2.4 Hz, 1 H), 8.38 (d, J=2.4 Hz, 1 H), 9.1–9.6 (br, 1 H), 10.0–10.9 (br, 1 H) IR (Nujol): 3110, 1740, 1570, 1455 cm⁻¹

Example 36

1-(6-Chloro-3-pyridylmethyl)amino-1-(2-methyl-aminocarbonyl)hydrazino-2-nitroethylene (Compound 54)

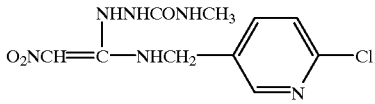

To a solution of 0.3 g (0.0012 mole) of 1-(6-chloro-3-pyridylmethyl)amino-1-hydrazino-2-nitroethylene in 5 ml of DMF was added 0.15 ml (0.0025 mole) of methyl isocyanate and the mixture was allowed to stand at room temperature for 2 hours. The DMF was distilled off under reduced. pressure and the residue was purified by silica gel column chromatography. The procedure gave 0.08 g of the title compound as a white solid.

m.p.: 190–192° C. (decompn.)

NMR (DMSO-d₆) δ: 2.63 (d, J=4.5 Hz, 3 H), 4.49 (br d, J=6.0 Hz, 2 H), 6.47 (s, 1 H), 6.5–6.8 (br d, J=4.5 Hz, 1 H), 7.51 (d, J=8.4 Hz, 1 H), 7.82 (dd, J=8.4 & 2.4 Hz, 1 H), 8.10 (s, 1 H), 8.40 (d, J=2.4 Hz, 1 H) IR (Nujol): 3200, 1680, 1550, 1455, 1380 cm$^{-1}$

Example 37

1-Methylamino-1-[N-methyl-N-[2-(3-pyridyl)ethyl]-amino]-2-nitroethylene (Compound 55)

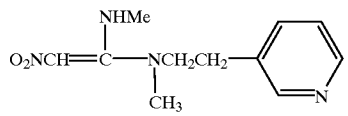

The steps (1), (2) and (3) of Example 13 were repeated except that N-methyl-N-[2-(3-pyridyl)ethyl]-amine was used in lieu of N-ethyl-N-(3-pyridylmethyl)-amine to give the following compounds in the respective steps.

(1) N-Methyl-N'-methyl-N'-[2-(3-pyridyl)ethyl]thiourea m.p.: 104–105° C.

NMR (CDCl$_3$) δ: 3.02 (m, CH$_2$-pyridine), 3.04 (s, MeNCH$_2$), 4.10 (m, CH$_2$N), 5.90 (br d, J=5 Hz, NH), 7.26 (dd, J=5 & 8 Hz, 1 H), 7.67 (m, 1 H), 8.50 (m, 2 H)

(2) S-Methyl-N-methyl-N'-methyl-N'-[2-(3-pyridyl)-ethyl]isothiourea (yellow brown oil)

(Note: After addition of 60% sodium hydride (oil), the mixture was stirred at 50° C. for 1 hour.)

NMR (CDCl$_3$) δ: 2.15 (s, MeS), 2.84 (m, CH-pyridine), 2.93 (s, MeNCH$_2$), 3.21 (s, MeN=), 3.61 (m, NCH$_2$), 7.20 (dd, J=5 & 8 Hz, 1 H), 7.53 (m, 1 H), 8.45 (m, 2 H)

(3) Title compound (yellow viscous oil)

NMR (CDCl$_3$) δ: 2.93 (d, J=5 Hz, MeNH), 2.96 (s, MeNCH$_2$s), 2.97 (m, CH$_2$-pyridine), 3.50 (m, MeNCH$_2$), 6.52 (s, =CHNO$_2$), 7.27 (dd, J=5 & 8 Hz, 1 H), 7.57 (m, 1 H), 8.50 (m, 2 H), 9.67 (br, NH)

Example 38

1-Dimethylamino-1-(N-methyl-N-3-pyridylmethyl)-amino-2-nitroethylene (Compound 56) and 1,1-bis (N-methyl-N-3-pyridylmethyl)amino-2-nitroethylene (Compound 57)

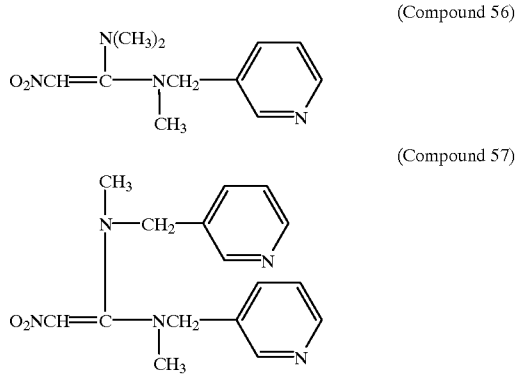

A mixture of 2.0 g (0.012 mole) of 1-dimethylamino-1-methylthio-2-nitroethylene and 1.5 g (0.012 mole) of N-methyl-N-3-pyridylmethylamine was stirred at 120° C. for 40 minutes. The reaction mixture was subjected to column chromatography, elution being carrid out with MeOH—CHCl$_3$ (1:10) to give two fractions containing the desired compounds, respectively. One of the fractions was further purified by silica gel column chromatography using MeOH—CHCl$_3$ (1:10) and acetone-CHCl$_3$ (2:1) in succesion, whereby 0.40 g of the title compound (Compound 56) was obtained as pale yellow crystals. The other fraction was also chromatographed on a silica gel column and eluted with MeOH—CHCl$_3$ (1:10) and acetone-CHCl$_3$ (2:1) in that order to give 0.35 g of the title compound (Compound 57) as a yellow oil. (Compound 56)

m.p.: 103–105° C.

NMR (CDCl$_3$) δ: 2.81 (s, 3 H), 2.98 (s, 6 H), 4.44 (s, 3 H), 6.41 (s, 1 H), 7.33 (dd, J=8.4 & 5.1 Hz, 1 H), 7.64 (dt, J=8.4 & 1.5 Hz, 1 H), 8.4–8.7 (m, 2 H) IR (Nujol): 1545, 1520, 1450, 1300, 1265 cm$^{-1}$ (Compound 57)

NMR (CDCl$_3$) δ: 2.83 (s, 6 H), 4.48 (s, 4 H), 6.52 (s, 1 H), 7.34 (dd, J=8.4. & 5.1 Hz, 2 H), 7.62 (dt, J=8.4 & 1.5 Hz, 2 H), 8.4–8.8 (m, 4 H)

Example 39

1-[N-(6-Chloro-3-pyridylmethyl)-N-methyl]amino-1-dimethylamino-2-nitroethylene (Compound 58)

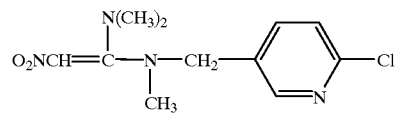

A mixture of 1.6 g (0.0099 mole) of 1-dimethylamino-1-methylthio-2-nitroethylene and 1.4 g (0.0089 mole) of N-(6-chloro-3-pyridylmethyl)-N-methylamine was stirred at 80° C. for 3 hours. The reaction mixture was subjected to silica gel column chromatography using MeOH—CDCl$_3$ (1:10) twice and acetone-CHCl$_3$ (2:1) once to give 0.33 g of the title compound as pale yellow crystals.

m.p.: 110–112° C.

NMR (CDCl$_3$) δ: 2.79 (s, 3 H), 2.97 (s, 6 H), 4.40 (s, 2 H), 6.38 (s, 1 H), 7.36 (d, J=8.4 Hz, 1 H), 7.72 (dd, J=8.4 & 2.4 Hz, 1 H), 8.30 (d, J=2.4 Hz, 1 H) IR (Nujol): 1545, 1520, 1460, 1300, 1260 cm$^{-1}$

Example 40

1-Amino-1-[N-(6-chloro-3-pyridylmethyl)-N-ethyl]-amino-2-nitroethylene (Compound 59)

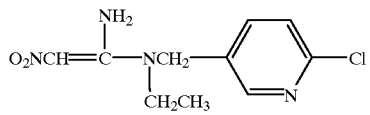

(1) In 200 ml of EtOH was dissolved 9.68 g of 1,1-bis-(methylthio)-2-nitroethylene with heating, and a solution of 6.66 g (0.039 mole) of N-(6-chloro-3-pyridylmethyl)-N-ethylamine in 30 ml of EtOH was added dropwise on reflux. After 45 hours of refluxing, the EtOH was distilled off and the residue was subjected to silica gel (420 g) column chromatography using EtOH—CHCl$_3$ (1:20) as an eluent. The procedure gave 2.28 g of crude 1-[N-(6-chloro-3-pyridylmethyl)-N-ethyl]amino-1-methylthio-2-nitroethylene as a brown oil.

NMR (CDCl$_3$) δ: 1.24 (t, J=7 Hz, CH$_2$CH$_3$), 2.46 (s, MeS), 3.52 (q, J=7 Hz, CH$_2$CH$_3$), 4.72 (s, CH$_2$-pyridine), 6.82 (s, =CHNO₂), 7.31 (d, J=8 Hz, 1 H), 7.57 (dd, J=8 & 2 Hz, 1 H), 8.30 (d, J=2 Hz, 1 H)

(2) In 30 ml of EtOH was dissolved 2.16 g of crude 1-[N-(6-chloro-3-pyridylmethyl)-N-ethyl]amino-1-methylthio-2-nitroethylene prepared in (1), followed by addition of 0.766 ml of 25% aqueous ammonia. The mixture was stirred at room temperature for 3 hours. The solvent was distilled off and the residue was subjected to silica gel (200 g) column chromatography, elution being carried out with MeOH—CHCl₃ (1:5). The procedure gave 0.69 g of the title compound as a pale yellow viscous oil. This product was triturated with ether, filtered and dried to give 0.57 g of the title compound as white powdery crystals.

m.p.:159–161° C.

NMR (CDCl₃-DMSO-d₆ [4:1]) δ: 1.22 (t, J=7 Hz, CH₂<u>CH</u>₃), 3.43 (q, <u>CH</u>₂CH₃), 4.62 (s, CH₂-pyridine), 6.61 (s, =CHNO₂), 7.38 (d, J=8 Hz, 1 H), 7.62 (dd, J=8 & 2 Hz, 1 H), 8.30 (d, J=2 Hz, 1 H), 8.97 (br, NH₂) IR (Nujol): 1610, 1565, 1455, 1445, 1305, 1235 cm⁻¹

Example 41

1-[N-(6-Chloro-3-pyridylmethyl)-N-ethyl]amino-1-methylamino-2-nitroethylene (Compound 60)

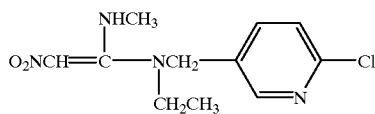

The steps (1), (2) and (3) of Example 37 were repeated except that N-(6-chloro-3-pyridylmethyl)-N-ethylamine was used in lieu of N-methyl-N-[2-(3-pyridyl)ethyl]amine to give the following compounds in the respective steps.

(1) N-(6-Chloro-3-pyridylmethyl)-N-ethyl-N-methylthiourea (yellow crystals)

m.p.: 133–134° C.

NMR (CDCl₃) δ: 1.16 (t, J=7 Hz, CH₂<u>CH</u>₃), 3.15 (d, J=5 Hz, MeN), 3.50 (q, J=7 Hz, <u>CH</u>₂CH₃), 5.12 (s, <u>CH</u>₂-pyridine), 5.84 (br d, J=5 Hz, NH), 7.30 (d, J=8 Hz, 1 H), 7.80 (dd, J=8 & 2 Hz, 1 H), 8.27 (d, J=2 Hz, 1 H)

(2) S-Methyl-N-(6-chloro-3-pyridylmethyl)-N-ethyl-N'-methylisothiourea (yellow brown oil)

NMR (CDCl₃) δ: 1.09 (t, J=7 Hz, CH₂<u>CH</u>₃), 2.29 (s, MeS), 3.21 (s, MeN=), 3.38 (q, J=7 Hz, <u>CH</u>₂CH₃), 4.49 (s, <u>CH</u>₂-pyridine), 7.27 (d, J=8 Hz, 1 H), 7.61 (dd, J=8 & 2 Hz, 1 H), 8.30 (d, J=2 Hz, 1 H)

(3) Title compound (white crystals)

m.p.: 83–84° C.

NMR (CDCl₃) δ: 1.20 (t, J=7 Hz, CH₂<u>CH</u>₃), 3.08 (d, J=5 Hz, Me<u>NH</u>), 3.18 (q, J=7 Hz, <u>CH</u>₂CH₃), 4.40 (s, <u>CH</u>₂pyridine), 6.54 (s, =CHNO₂), 7.39 (d, J=8 Hz, 1 H), 7.63 (dd, J=8 & 2 Hz, 1 H), 8.33 (d, J=2 Hz, 1 H), 9.79 (br d, J=5 Hz, NH) IR (Nujol): 1595, 1530, 1455, 1340, 1270, 1240 cm⁻¹

Example 42

1-(N-(6-Methoxy-3-pyridylmethyl)-N-methyl]amino-1-methylamino-2-nitroethylene (Compound 61)

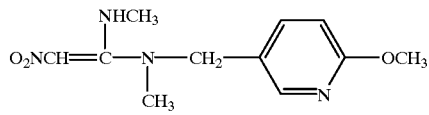

In 20 ml of DMF was dissolved 0.67 g (0.0026 mole) of 1-[N-(6-chloro-3-pyridylmethyl)-N-methyl]amino-1-methylamino-2-nitroethylene followed by addition of 1.00 g of a 28% solution of sodium methoxide in methanol. The mixture was stirred at 100° C. for 5.5 hours. The methanol and DMF were distilled off and the residue was diluted with aqueous sodium chloride solution and extracted with CH₂Cl₂. The extract was dried over MgSO₄ and the CH₂Cl₂ was distilled off. The residue was subjected to silica gel (230 g) column chromatography using MeOH—CHCl₃ (1:5) as an eluent to give 0.22 g of a brown viscous oil. A small amount of ether was added to the oil and the mixture was cooled and triturated. The resulting crystals were diluted with ether, filtered and dried to give 0.128 g of the title compound as white—pale brown crystals.

m.p.: 77–78° C.

NMR (CDCl₃) δ: 2.75 (s, MeN), 3.07 (d, J=5 Hz, <u>Me</u>NH), 3.93 (s, OMe), 4.30 (s, <u>CH</u>₂-pyridine), 6.53 (s, =CHNO₂), 6.78 (d, J=8 Hz, 1 H), 7.45 (dd, J=8 & 2 Hz, 1 H), 8.05 (d, J=2 Hz, 1 H), 9.80 (br, NH) IR (Nujol): 1605, 1455, 1310, 1250, 1025 cm⁻¹

Example 43

1-Methylamino-1-[N-methyl-N-(4-pyridylmethyl)]-amino-2-nitroethylene (Compound 62)

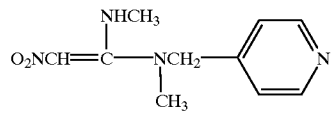

The steps (1), (2) and (3) of Example 37 were repeated except that N-methyl-N-(4-pyridylmethyl)amine was used in lieu of N-methyl-N-[2-(3-pyridyl)ethyl]-amine to give the following compounds in the respective steps.

(1) N-Methyl-N'-methyl-N'-(4-pyridylmethyl)thiourea m.p.: 123–124° C.

NMR (CDCl₃) δ: 3.07 (s, <u>Me</u>NCH₂), 3.16 (d, J=5 Hz, <u>Me</u>NH), 5.19 (s, CH₂), 6.29 (br d, J=5 Hz, NH), 7.19 (m, 2 H), 8.52 (m, 2 H).

(2) S-Methyl-N-methyl-N'-methyl-N'-(4-pyridylmethyl)isothiourea (brown oil)

NMR (CDCl₃) δ: 2.30 (s, MeS), 2.87 (s, <u>Me</u>NCH₂, 3.27 (s, MeN=), 4.59 (s, CH₂), 7.18 (m, 2 H), 8.54 (m, 2 H)

(3) Title compound m.p.: 145–146° C.

NMR (CDCl₃) δ: 2.88 (s, <u>Me</u>NCH₂), 3.07 (d, J=5 Hz, Me<u>NH</u>), 4.43 (s, CH₂), 6.54 (s, =CHNO₂), 7.21 (m, 2 H), 8.65 (m, 2 H), 9.78 (br, NH) IR (Nujol): 1600, 1565, 1455, 1435, 1410, 1320, 1260 cm⁻¹

Example 44

1-Methylamino-1-[N-methyl-N-(2-pyridylmethyl)]-amino-2-nitroethylene (Compound 63)

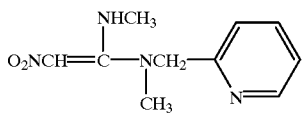

The steps (1), (2) and (3) of Example 37 were repeated except that N-methyl-N-(2-pyridylmethyl)amine was used in lieu of N-methyl-N-[2-(3-pyridyl)ethyl]-amine to give the following compounds in the respective steps.

(1) N-Methyl-N'-methyl-N'-(2-pyridylmethyl)thiourea (yellow brown viscous oil)

NMR (CDCl$_3$) δ: 3.15 (d, J=5 Hz, MeNH), 3.31 (s, MeNCH$_2$), 4.90 (s, CH$_2$), 7.15–7.6 (m, 3 H, pyridine-H$_2$ & NH), 7.73 (t, J=7 Hz, 1 H), 8.55 (d, J=5 Hz, 1 H)

(2) S-Methyl-N-methyl-N'-methyl-N'-(2-pyridylmethyl)-isothiourea (brown oil)

NMR (CDCl$_3$), δ: 2.30 (s, MeS), 2.91 (s, MeCH$_2$), 3.28 (s, MeN=), 4.77 (s, CH$_2$), 7.05–7.45 (m, 2 H), 7.67 (m, 1 H), 8.56 (d, J=5 Hz, 1 H)

(3) Title compound m.p.: 96–97° C.

NMR (CDCl$_3$) δ: 2.96 (s, MeNCH$_2$), 3.08 (d, J=5 Hz, MeNH), 4.53 (s, CH$_2$), 6.57 (s, =CHNO$_2$), 7.30 (m, 2 H), 7.78 (m, 1 H), 8.63 (m, 1 H), 9.61 (br, NH) IR (Nujol): 1580, 1545, 1425, 1380, 1280 cm$^{-1}$

Example 45

1-[N-methoxy-N-(3-pyridylmethyl)]amino-1-methylamino-2-nitroethylene (Compound 64)

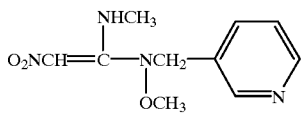

The steps (1), (2) and (3) of Example 37 were repeated except that O-methyl-N-(3-pyridylmethyl)-hydroxylamine was used in lieu of N-methyl-N-[2-(3-pyridyl)ethyl]amine to give the following compounds in the respective steps.

(1) N-Methoxy-N-(3-pyridylmethyl)-N'-methylthiourea (provide, however, that acetonitrile was used as the reaction solvent and the reaction was conducted at 50° C. for 5 hours)

m.p.: 95–96° C.

NMR (CDCl$_3$) δ: 3.15 (d, J=5 Hz, 3 H), 3.63 (s, 3 H), 5.32 (s, 2 H), 7.03–7.46 (br, NH), 7.27 (dd, J=8 & 5 Hz, 1 H), 7.86 (dt, J=8 & 2 Hz, 1 H), 8.56 (dd, J=5 & 2 Hz, 1 H), 8.66 (d, J=2 Hz, 1 H).

(2) S-Methyl-N-methoxy-N-(3-pyridylmethyl)-N'-methyl-isothiourea (pale yellow oil)

NMR (CDCl$_3$) δ: 2.23 & 2.45 (each s, total 3 H), 3.26 & 3.32 (each s, total 3 H), 3.40 & 3.50 (each s, total 3 H), 4.08 & 4.52 (each s, total 2 H), 7.20–7.43 (m, 1 H), 7.76 (m, 1 H), 8.50–8.76 (m, 2 H).

(3) Title compound m.p. 100–101° C.

NMR (CDCl$_3$) δ: 3.18 (d, J=5 Hz, 3 H), 3.45 (s, 3 H), 4.30 (s, 2 H), 6.90 (s, 1 H), 7.33 (dd, J=8 & 5 Hz, 1 H), 7.73 (dt, J=8 & 2 Hz, 1 H), 8.56–8.73 (m, 2 H), 9.73 (br, NH) IR (Nujol): 1613, 1460, 1360, 1250, 1080 cm$^{-1}$

Example 46

1-(N-Formyl-N-methyl)amino-1-[N-methyl-N-(3-pyridyl-methyl)]amino-2-nitroethylene (Compound 65)

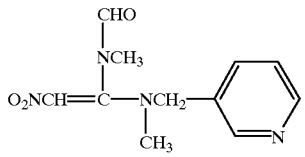

In 10 ml of dry THF was suspended 0.1 g of petroleum ether-washed 60% sodium hydride, followed by addition of 0.51 g (0.0023 mole) of 1-methylamino-1-[N-methyl-N-(3-pyridylmethyl)]amino-2-nitroethylene. The mixture was stirred at room temperature overnight. Then, under ice-cooling, 0.6 g of formic acetic anhydride was added and the mixture as stirred at that temperature for 1 hour. The solvent was distilled off and the residue was diluted with 30 ml of water, neutralized with NaHCO$_3$ and extracted with CH$_2$Cl$_2$ (30 ml×3). The extract was dried over MgSO$_4$, the CH$_2$Cl$_2$ was removed by distillation and the residue was subjected to silica gel column chromatography, elution being carried out with MeOH—CHCl$_3$ (1:5). The procedure gave 0.25 g of the title compound as pale yellow prisms.

m.p.: 97–98° C.

NMR (DMSO-d$_6$) δ: 2.93 (s, 3 H), 3.03 (s, 3 H), 4.62 (br, 2 H), 6.86 (s, 1 H), 7.42 (dd, J=8 & 5 Hz, 1 H), 7.73 (br d, J=8 Hz, 1 H), 8.25 (s, 1 H), 8.55 (br, 2 H) IR (Nujol): 1700, 1560, 1350, 1285, 1260, 890 cm$^{-1}$

Example 47

N$^2$-Methoxy-2-nitro-N$^1$-(3-pyridylmethyl) acetamidine Compound 66)

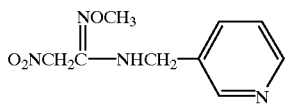

To 3 ml of isobutyl alcohol was added 0.75 g (0.0033 mole) of 1-methylthio-1-(3-pyridylmethyl)amino-2-nitroethylene, followed by addition of 0.56 g of O-methylhydroxylamine hydrochloride at 100–110° C. Then, a solution of 0.93 ml of triethylamine in 1 ml of isobutyl alcohol was added dropwise at the same temperature with stirring over a period of 30 minutes. After completion of dropwise addition, the reaction mixture was allowed to cool to room temperature and the solvent was distilled off. The residue was purified by silica gel column chromatography [eluents: MeOH—CHCl$_3$ (1:3) in the first run and MeOH—CHCl$_3$ (1:10) in the second run] to give 0.23 g of the title compound as yellow crystals.

m.p.: 77–78° C.

NMR (CDCl$_3$) δ: 3.86 (s, 3 H), 4.37 (d, J=6.3 Hz, 2 H), 5.04 (s, 2 H), 5.2–5.8 (br, 1 H), 7.32 (dd, J=8.4 & 5.1 Hz, 1 H), 7.65 (dt, J=8.4 & 1.5 Hz, 1 H), 8.4–8.8 (2 H, m).

Example 48

1-(2-Methoxyethyl)amino-1-[N-methyl-N-(3-pyridyl-methyl)]amino-2-nitroethylene (Compound 67)

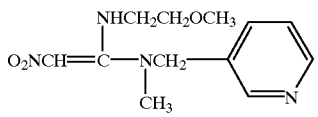

The steps (1), (2) and (3) of Example 13 were repeated except that N-methyl-N-(3-pyridylmethyl)amine and (2-methoxy)ethyl isothiocyanate were used in lieu of N-ethyl-N-(3-pyridylmethyl)amine and methyl isothiocyanate, respectively, to give the following compounds in the respective steps.

(1) N-(2-methoxyethyl)-N'-methyl-N'-(3-pyridylmethyl)-thiourea (colorless oil)

NMR (CDCl$_3$) δ: 3.06 (s, 3 H), 3.36 (s, 3 H), 3.57 (t, J=5.1 Hz, 2 H), 3.91 (dt, J=5.1 & 5.1 Hz, 2 H), 5.21 (s, 2 H), 5.9–6.3 (br, 1 H), 7.28 (dd, J=8.4 & 5.1 Hz, 1 H), 7.75 (dt, J=8.4 & 1.5 Hz, 1 H), 8.5–8.7 (m, 2 H).

(2) S-Methyl-N-(2-methoxyethyl)-N'-methyl-N'-(3-pyridylmethyl)isothiourea (yellow oil)

NMR (CDCl$_3$) δ: 2.30 (s, 3 H), 2.88 (s, 3 H), 3.37 (s, 3 H), 3.4–3.8 (m, 4 H), 4.59 (s, 2 H), 7.25 (dd, J=8.4 & 5.1 Hz, 1 H), 7.62 (dt, J=8.4 & 1.5 Hz, 1 H), 8.4–8.7 (m, 2 H)

(3) Title compound m.p. 55–57° C.

NMR (CDCl$_3$) δ: 2.79 (s, 3 H), 3.3–3.7 (m, 4 H), 3.41 (s, 3 H), 4.43 (s, 2 H), 6.53 (S, 1 H), 7.35 (dd, J=8.4 & 1.5 Hz, 1 H), 7.60 (dt, J=8.4 & 1.5 Hz, 1 H), 8.5–8.7 (m, 2 H), 9.4–9.9 (br, 1 H)

Example 49

1-[N-(4-Chlorobenzyl)-N-methyl]amino-1-methylamino-2-nitroethylene (Compound 68)

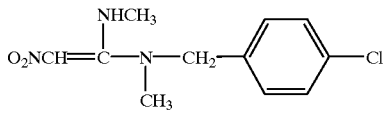

(1) In 50 ml of dry THF was dissolved 4.69 g (0.0205 mole) of N-(4-chlorobenzyl)-N-methyl-N'-methylthiourea, followed by addition of 0.82 g of 60% sodium hydride (oil). The mixture was refluxed for 1 hour. Then, under cooling with ice-water and stirring, 1.277 ml of methyl iodide was added dropwise and after completion of dropwise addition, the mixture was further stirred at room temperature for 45 minutes. The THF was distilled off and the residue was diluted with water (about 50 ml), saturated with sodium chloride, and extracted with AcOEt (100 ml×3). The extract was dried over MgSO$_4$ and the solvent was distilled off to give 5.11 g of crude S-methyl-N-(4-chlorobenzyl)-N-methyl-N'-methylisothiourea as a colorless—pale yellow oil.

NMR (CDCl$_3$) δ: 2.28 (s, MeS), 2.80 (s, MeNCH$_2$), 3.26 (s, MeN=), 4.53 (s, CH$_2$), 7.14 & 7.31 (each d, J=9 Hz, each 2 H)

(2) To 4.98 g (0.0205 mole) of S-methyl-N-(4-chlorobenzyl)-N-methyl-N'-methylisothiourea prepared in (1) was added 25 ml of nitromethane and the mixture was refluxed for 6.5 hours. The nitromethane was distilled off and the residue was subjected to silica gel (240 g) column chromatography using MeOH—CHCl$_3$ (1:10) as an eluent to give 5.23 g of an orange-colored oil. To this oil were added small amounts of EtOH and ether and the mixture was cooled in a dry ice-acetone bath and triturated to give crystals. After addition of ether, the crystals were collected by filtration, washed with ether and dried. The procedure gave 3.69 g of the title compound as pale yellow cyrstals.

m.p.: 98–99° C.

NMR (CDCl$_3$) δ: 2.79 (s, MeNCH$_2$), 3.05 (d, J=5 Hz, MeNH), 4.34 (s, CH$_2$), 6.53 (s, =CHNO$_2$), 7.17 & 7.38 (each d, J=8 Hz, each 2 H), 9.79 (br, NH) IR (Nujol): 1450, 1310, 1235, 1070, 1025 cm$^{-1}$

Example 50

1-Amino-1-(4-chlorobenzyl)amino-2-nitroethylene (Compound 69)

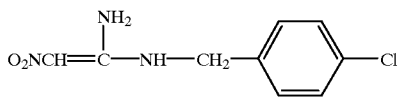

To 2.59 g (0.01 mole) of 1-(4-chlorobenzyl)amino-1-methylthio-2-nitroethylene were added 45 ml of EtOH, 10 ml of THF and 1.02 g of 25% aqueous ammonia and the mixture was stirred at an external temperature of 60° C. for 5.5 hours. During this period, 1.02 g each of 25% aqueous ammonia was added after 1, 2 and 3 hours of reaction. The reaction mixture was ice-cooled and stirred, whereupon crystals separated out. The crystals were collected by filtration, washed with EtOH and ether in that order, and dried. The procedure gave 1.11 g of the title compound as white crystals.

m.p.: 215–216° C. (decompn.)

NMR (DMSO-d$_6$) δ: 4.47 (d, J=7 Hz, CH$_2$), 6.45 (s, =CHNO$_2$), 7.34 & 7.44 (each d, J=9 Hz, each 2 H), 8.02 (br, NH$_2$) 9.25 (br, NH) IR (Nujol): 3100, 1560, 1430, 1405, 1195, 1030 cm$^{-1}$

Example 51

1-(4-Chlorobenzyl)amino-1-methylamino-2-nitroethylene (Compound 70)

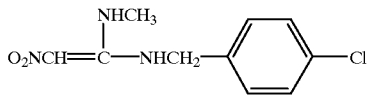

In 100 ml of EtOH on reflux was dissolved 2.59 g (0.01 mole) of 1-(4-chlorobenzyl)amino-1-methylthio-2-nitroethylene, and with refluxing continued, a solution of 1.94 g of 40% aqueous methylamine solution in 10 ml of EtOH was added dropwise over a period of 50 minutes. After completion of dropwise addition, the mixture was further refluxed for 15 minutes, at the end of which time it was cooled with ice-water, whereupon crystals separated out. The crystals were collected by filtration, washed with EtOH and ether in that orsder, and dried. The procedure gave 1.66 g of the title compound as white crystals.

m.p.: 219–220° C. (decompn.)

NMR (DMSO-d$_6$) δ: 2.88 (br d, J=3 Hz, Me), 4.43 (d, J=6 Hz, CH$_2$), 6.43 (s, =CHNO$_2$), 7.40 (s, 4 H), 7.7 (br, MeN H), 9.9 (br, HNCH$_2$) IR (Nujol): 1455, 1425, 1375, 1360, 1215, 995 cm$^{-1}$ Example 52

1-(4-Chlorobenzyl)amino-1-dimethylamino-2-nitroethylene (Compound 71)

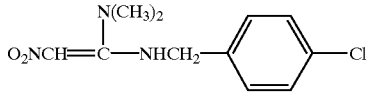

In 100 ml of EtOH was dissolved 2.59 g (0.01 mole) of 1-(4-chlorobenzyl)amino-1-methylthio-2-nitroethylene with heating. Then, with refluxing and stirring, a solution of 2.25 g of 50% aqueous dimethylamine solution in 10 ml of EtOH was added dropwise over a period of 35 minutes. After completion of dropwise addition, the mixture was further stirred and refluxed for 2.5 hours. The solvent was then distilled off and the residue was diluted with ether and triturated, whereupon crystals separated. After addition of EtOH and ether (about 1:5), the crystals were collected by filtration, washed with ether and dried. The procedure gave 1.21 g of the title compound as white crystals.

m.p.: 133–135° C.

NMR (CDCl$_3$) δ: 2.91 (s, Me$_2$N), 4.45 (d, J=6 Hz, CH$_2$), 6.51 (s, =CHNO$_2$), 7.30 (s, 4 H), 9.79 (br, NH) IR (Nujol): 1620, 1500, 1435, 1420, 1370, 1220, 1195 cm$^{-1}$ Example 53

1-Dimethylamino-1-[N-formyl-N-(3-pyridylmethyl)]-amino-2-nitroethylene (Compound 72)

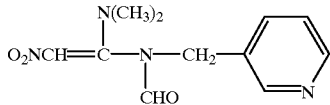

In 10 ml of dry THF was suspended 0.1 g of 60% sodium hydride (oil) followed by addition of 0.56 g (0.0025 mole) of 1-dimethylamino-1-(3-pyridylmethyl)-amino-2-nitroethylene, and the mixture was stirred at room temperature overnight. Then, under ice-cooling, 0.7 g of formic acetic anhydride was added, followed by stirring at the same temperature for 2 hours. The solvent was distilled off and the residue was diluted with 30 ml of water, neutralized with NaHCO$_3$ and extracted with CH$_2$Cl$_2$ (30 ml×3). The extract was dried over MgSO$_4$, the solvent was distilled off and the residue was subjected to silica gel column chromatography using MeOH—CHCl$_3$ (1:5) as an eluent. The procedure gave 0.2 g of the title compound as a pale yellow viscous oil.

NMR (DMSO-d$_6$) δ: 2.90 (s, 6 H), 4.40–5.06 (m, 2 H), 6.73 (s, 1 H), 7.33 (dd, J=8 & 5 Hz, 1 H), 7.75 (br d, J=8 Hz, 1 H), 8.26 (s, 1 H), 8.55 (br, 2 H) IR (neat): 1685, 1570, 1500, 1350, 1270 cm$^{-1}$ Example 54

1-Methylamino-1-[N-methyl-N-(2-pyrazinyl)methyl]amino-2-nitroethylene (Compound 73)

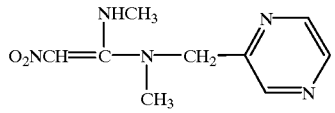

The steps (1), (2) and (3) of Example 13 were repeated except that N-methyl-N-(2-pyrazyl)methylamine was used in lieu of N-ethyl-N-(3-pyridylmethyl)amine to give the following compounds in the respective steps.

(1) N-Methyl-N'-methyl-N'-[(2-pyrazyl)methyl]thiourea m.p.: 123–124° C.

NMR (CDCl$_3$) δ: 3.17 (d, J=5 Hz, 3 H), 3.26 (s, 2 H), 5.12 (s, 2 H), 6.42 (br, 1 H), 8.53 (s, 2 H), 8.72 (s, 1 H)

(2) S-Methyl-N-methyl-N'-methyl-N'-[(2-pyrazyl)methyl]-isothiourea (pale yellow oil)

NMR (CDCl$_3$) δ: 2.32 (s, 3 H), 2.98 (s, 3 H), 3.26 (s, 3 H), 4.76 (s, 2 H), 8.45–8.66 (m, 3 H)

(3) Title compound m.p.: 132–133° C.

NMR (CDCl$_3$) δ: 2.93 (s, 3 H), 3.09 (d, J=5 Hz, 3 H), 4.56 (s, 2 H), 6.60 (s, 1 H), 8.62 (s, 3 H), 9.60 (br, 1 H) IR (Nujol): 3150, 1580, 1410, 1280, 1240, 1020, 990 cm$^{-1}$ Example 55

1-(2,2-Dimethyl-1-hydrazino)-1-[N-methyl-N-(3-pyridylmethyl]amino-2-nitroethylene (Compound 74)

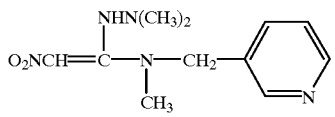

A mixture of 4.3 g (0.024 mole) of 1-(2,2-dimethyl-1-hydrazino)-1-methylthio-2-nitroethylene and 3.6 g of N-methyl-N-(3-pyridylmethyl)amine was stirred at 90–100° C. for 4 hours, after which it was subjected to silica gel column chromatography using MeOH—CHCl$_3$ (1:10) as an eluent. The resulting crystals were washed with ether and dried to give 0.7 g of the title compound. NMR of this product showed that it was a 3:2 mixture of the title compound and N$^2$-dimethylamino-N$^1$-methyl-2-nitro-N$^1$-(3-pyridylmethyl)acetamidine.

m.p.: 80–82° C.

NMR (CDCl$_3$) δ: 2.40 (s, 2.4 H), 2.59 (s, 3.6 H), 2.87 (s, 1.2 H), 2.90 (s, 1.8 H), 4.61 (s, 0.8 H), 4.63 (s, 1.2 H), 6.00 (s, 0.8 H), 6.47 (s, 0.6 H), 7.15–7.45 (m, 1 H), 7.45–7.80 (m, 1 H), 8.45–8.70 (m, 2 H), 10.1–10.5 (br s, 0.6 H) IR (Nujol): 3130, 1585, 1570, 1445, 1425 cm$^{-1}$

Example 56

1-Amino-1-[N-(6-chloro-3-pyridylmethyl)-N-n-propyl]-amino-2-nitroethylene (Compound 75)

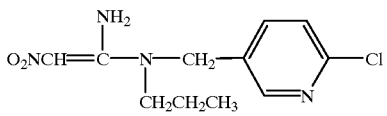

In 40 ml of EtOH was dissolved 2.83 g (0.0094 mole) of 1-[N-(6-chloro-3-pyridylmethyl)-N-n-propyl]-amino-1-methylthio-2-nitroethylene followed by addition of 0.96 ml of 25% aqueous ammonia. The mixture was stirred at room temperature for 3 hours. The resulting crystals were collected by filtration, washed with small amounts of EtOH and ether in that order, and dried to give 1.35 g of the title compound as pale yellow crystals.

m.p: 185–186° C. (decompn.)

NMR (DMSO-$d_6$) δ: 0.87 (t, J=7 Hz, CH$_2$C$\underline{H}_3$), 1.59 (sextet, J=7 Hz, C$\underline{H}_2$CH$_3$), 3.31 (t, J=7 Hz, NC$\underline{H}_2$CH$_2$), 4.68 (s, CH$_2$-pyridine), 6.59 (s, =CHNO$_2$), 7.50 (d, J=8 Hz, 1 H), 7.71 (dd, J=8 & 2 Hz, 1 H), 8.31 (d, J=2 Hz, 1 H), 8.99 (br, NH$_2$) IR (Nujol): 1615, 1550, 1455, 1335, 1320, 1300, 1285 cm$^{-1}$

Example 57

1-[N-(6-Chloro-3-pyridylmethyl)-N-n-propyl]-amino-1-methylamino-2-nitroethylene (Compound 76)

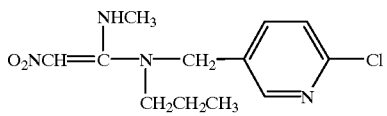

The steps (1), (2) and (3) of Example 13 were repeated except that N-(6-chloro-3-pyridylmethyl)-N-n-propylamine was used in lieu of N-ethyl-N-(3-pyridylmethyl)amine to give the following compounds in the respective steps.

(1) N-(6-Chloro-3-pyridylmethyl)-N-n-propyl-N'-methylthiourea (pale yellow crystals)

m.p.: 95–96° C.

NMR (CDCl$_3$) δ: 0.89 (t, J=8 Hz, CH$_2$C$\underline{H}_3$), 1.63 (sextet, J=8 Hz, C$\underline{H}_2$CH$_3$), 3.17 (d, J=5 Hz, MeN), 3.36 (t, J=8 Hz, CH$_2$C$\underline{H}_2$N), 5.16 (s, CH$_2$-pyridine), 5.87 (br q, J=5 Hz, NH), 7.30 (d, J=8 Hz, 1 H), 7.78 (dd, J=8 & 2 Hz, 1 H), 8.30 (d, J=2 Hz, 1 H)

(2) S-Methyl-N-(6-chloro-3-pyridylmethyl)-N-n-propyl-N'-methylisothiourea (yellow oil)

(provided, however, that after addition of 60% sodium hydride (oil), the mixture was stirred at 50° C. for 1 hour.)

NMR (CDCl$_3$) δ: 0.85 (t, J=7 Hz, CH$_2$C$\underline{H}_3$), 1.55 (sextet, J=7 Hz, C$\underline{H}_2$CH$_3$), 2.26 (s, MeS), 3.21 (s, MeN=), 3.29 (t, J=7 Hz, CH$_2$C$\underline{H}_2$N), 4.52 (s, CH$_2$-pyridine), 7.26 (d, J=8 Hz, 1 H), 7.60 (dd, J=8 & 2 Hz, 1 H), 8.30 (d, J=2 Hz, 1 H)

(3) Title compound (pale yellow—pale brown crystals) (provided, however, that the reaction mixture was refluxed in nitromethane for 34 hours.)

m.p.: 102–103° C.

NMR (CDCl$_3$) δ: 0.88 (t, J=7 Hz, CH$_2$C$\underline{H}_3$), 1.63 (sextet, J=7 Hz, C$\underline{H}_2$CH$_3$), 3.04 (t, J=7 Hz, CH$_2$C$\underline{H}_2$N), 3.08 (d, J=5 Hz, MeN), 4.40 (s, CH$_2$-pyridine), 6.54 (s, =CHNO$_2$), 7.38 (d, J=8 Hz, 1 H), 7.60 (dd, J=8 & 2 Hz, 1 H), 8.33 (dd, J=2 Hz, 1 H), 9.78 (br q, J=5 Hz, NH) IR (Nujol): 1590, 1520, 1450, 1350, 1270, 1245, 1095 cm$^{-1}$

Example 58

1-[N-(6-Chloro-3-pyridylmethyl)-N-i-propyl]amino-1-methylamino-2-nitroethylene (Compound 77)

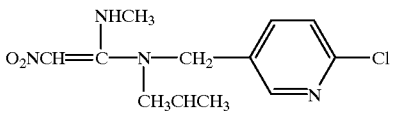

The steps (1), (2) and (3) of Example 13 were repeated except that N-(6-chloro-3-pyridylmethyl)-N-i-propylamine was used in lieu of N-ethyl-N-(3-pyridylmethyl)amine to give the following compounds in the respective steps.

(1) N-(6-Chloro-3-pyridylmethyl)-N-i-propyl-N'-methylthiourea (pale yellow crystals)

m.p.: 92–93° C.

NMR (CDCl$_3$) δ: 1.17 (d, J=7 Hz, $\underline{Me}_2$CH), 3.12 (d, J=5 Hz, MeN), 4.87 (s, CH$_2$), 5.08 (septet, J=7 Hz, Me$_2$C$\underline{H}$), 5.80 (br q, J=5 Hz, NH), 7.30 (d, J=8 Hz, 1 H), 7.65 (dd, J=8 & 2 Hz, 1 H), 8.27 (d, J=2 Hz, 1 H)

(2) S-Methyl-N-(6-chloro-3-pyridylmethyl)-N-i-propyl-N'-methylisothiourea (pale brown oil)

(provided, however, that after addition of 60% sodium hydride (oil), the mixture was stirred at 50° C. for 1 hour.)

NMR (CDCl$_3$) δ: 1.20 (d, J-7 Hz, $\underline{Me}_2$CH), 2.23 (s, MeS), 3.10 (s, MeN=), 4.24 (s, CH$_2$-pyridine), 4.44 (septet, J=7 Hz, Me$_2$C$\underline{H}$), 7.23 (d, J=8 Hz, 1 H), 7.56 (dd, J=8 & 2 Hz, 1 H), 8.30 (d, J=2 Hz, 1 H)

(3) Title compound (white—pale brown crystals)

(provided, however, that the reaction mixture was refluxed in nitromethane for 130 hours.)

m.p.: 119–120° C.

NMR (CDCl$_3$) δ: 1.31 (d, J=7 Hz, $\underline{Me}_2$CH), 3.04 (d, J=5 Hz, MeN), 3.79 (septet, J=7 Hz, Me$_2$C$\underline{H}$), 4.20 (s, CH$_2$), 6.56 (s, =CHNO$_2$), 7.30 (d, J=8 Hz, 1 H), 7.56 (dd, J=8 & 2 Hz, 1 H), 8.30 (d, J=2 Hz, 1 H), 9.78 (br q, J=5 Hz, NH) IR (Nujol): 1590, 1450, 1360, 1335, 1270, 1235, 1105 cm$^{-1}$

Example 59

1-[N-(6-Chloro-3-pyridyl)-N-methyl]amino-1-methylamino-2-nitroethylene (Compound 78)

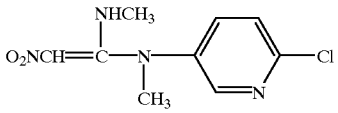

(1) In 50 ml of acetonitrile, 4.0 g (0.028 mole) of 2-chloro-5-methylaminopyridine and 3.7 g of methyl isothiocyanate were refluxed for 52.5 hours and the reaction mixtrue was concentrated. To the residue were added 30 ml of ice-water and 2 ml of 3N-HCl, followed by extraction with AcOEt (50 ml×3). The extracts were pooled, washed successively with 3N-HCl (4 times), aqueous sodium chloride solution (4 times) and aqueous sodium hydrogen carbonate solution (once), and dried over MgSO$_4$. The AcOEt was distilled off under reduced pressure and after addition of ether, the crystals were collected by filtration and dired to give 2.8 g of N-(6-chloro-3-pyridyl)-N-methyl-N'-methylthiourea as white crystals.

m.p.: 87.5–88° C.

NMR (CDCl₃) δ: 3.09 (d, J=4.5 Hz, 3 H), 3.65 (s, 3 H), 5.3–6.0 (m, 1 H), 7.47 (d, J=8.4 Hz, 1 H), 7.61 (dd, J=8.4 & 2.4 Hz, 1 H), 8.33 (d, J=2.4 Hz, 2 H)

(2) In 10 ml of dry tetrahydrofuran was suspended 0.9 g of 60% sodium hydride (oil) which had been washed twice with petroleum ether, and with stirring, a solution of 2.5 g (0.012 mole) of N-(6-chloro-3-pyridyl)-N-methyl-N'-methylthiourea in 30 ml of dry tetrahydrofuran was added dropwise. After completion of dropwise addition, the mixture was stirred at 50° C. for 0.5 hour. Then, at room temperature, 2.2 g of methyl iodide was added dopwise and the mixture was further stirred for 3 hours. The reaction mixture was concentrated under reduced pressure and after addition of 50 ml of iced water and 3 ml of 3N-HCl, the concentrate was extracted with AcOEt (50 ml×3). The extracts were pooled, washed with water (twice) and dried over MgSO₄. Finally, the AcOEt was distilled off under reduced pressure to recover 2.6 g of crude S-methyl-N-(6-chloro-3-pyridyl)-N-methyl-N'-methylisothiourea as a brown oil.

NMR (CDCl₃) δ: 2.07 & 2.38 (each s, 3 H), 3.06 & 3.27 (each s, 3 H), 3.17 & 3.30 (each s, 3 H), 6.9–7.6 (m, 2 H), 7.90 & 8.24 (each d, J=3.0 Hz, 1 H)

(3) In 40 ml of nitromethane, 2.6 g (0.011 mole) of S-methyl-N-(6-chloro-3-pyridyl)-N-methyl-N'-methylisothiourea was refluxed for 63 hours. The reaction mixture was then concentrated and the residue was subjected to silica gel column chromatography using hexane-acetone (1:2) as an eluent. The resulting crystals were washed with ether and dried to give 1.3 g of the title compound as pale yellow crystals.

m.p.: 108–109° C.

NMR (CDCl₃) δ: 2.75 (d, J=5.1 Hz, 3 H), 3.30 (s, 3 H), 6.63 (s, 1 H), 7.2–7.6 (m, 2 H), 8.2–8.3 (m, 1 H), 9.6–10.3 (m, 1 H)

IR (Nujol): 3120, 1600 cm⁻¹

Example 60

1-Methylamino-1-[N-methyl-N-(3-pyridyl)]amino-2-nitroethylene (Compound 79)

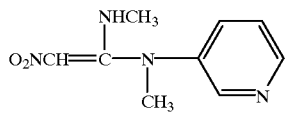

The steps (1), (2) and (3) of Example 59 were repeated except that 3-methylaminopyridine was used in lieu of 2-chloro-5-methylaminopyridine to give the following compounds in the respective steps.

(1) N-Methyl-N'-methyl-N'-(3-pyridyl)thiourea (white crystals)

m.p.: 93–94° C.

NMR (CDCl₃) δ: 3.08 (d, J=4.5 Hz, 3 H), 3.69 (s, 3 H), 5.2–5.8 (m, 1 H), 7.47 (dd, J=8.1 & 4.7 Hz, 1 H), 7.64 (dm, J=8.4 & 2.3 Hz, 1 H), 8.4–8.8 (m, 2 H)

(2) S-Methyl-N-methyl-N'-methyl-N'-(3-pyridyl) isothiourea (red brown oil)

NMR (CDCl₃) δ: 2.01 & 2.37 (each s, 3 H), 3.05 & 3.27 (each s, 3 H), 3.17 & 3.29 (each s, 3 H), 6.9–7.6 (m, 2 H), 8.0–8.6 (m, 2H)

(3) Title compound (pale brown crystals)

m.p.: 113–114° C.

NMR (DMSO-d₆) δ: 2.66 (d, J=5.1 Hz, 3 H), 3.29 (s, 3 H), 6.53 (s, 1 H), 7.41 (dd, J=8.4 & 4.5 Hz, 1 H), 7.5–7.8 (m, 1 H), 8.2–8.7 (m, 2 H), 9.4–10.0 (m, 1 H)

IR (Nujol): 3190, 3140, 1595 cm⁻¹

Example 61

1-[N-(6-Chloro-3-pyridylmethyl)-N-methyl]amino-1-ethylamino-2-nitroethylene (Compound 80)

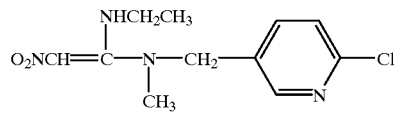

Using N-(6-chloro-3-pyridylmethyl)-N-methylamine and ethyl isothiocyanate in lieu of N-ethyl-N-(3-pyridylmethyl) amine and methyl isothiocyanate, respectively, the reaction steps (1), (2) and (3) of Example 13 were followed to give the following compounds in the respective steps.

(1) N-(6-Chloro-3-pyridylmethyl)-N-ethyl-N-methylthiourea (white crystals)

m.p. 82–83° C.

NMR (CDCl₃) δ: 1.24 (t, J=7 Hz, CH₂C$\underline{H}$₃), 3.04 (s, MeN), 3.72 (dq, J=5 & 7 Hz, C$\underline{H}$₂CH₃), 5.22 (s, CH₂-pyridine), 5.66 (br, NH), 7.33 (d, J=8 Hz, 1H), 7.79 (dd, J=8 & 2 Hz, 1H), 8.33 (d, J=2 Hz, 1 H)

(2) S-Methyl-N-(6-chloro-3-pyridylmethyl)-N'-ethyl-N-methylisothiourea (brown oil)

NMR (CDCl₃) δ: 1.12 (t, J=7 Hz, CH₂C$\underline{H}$₃), 2.30 (s, MeS), 2.87 (s, $\underline{Me}$NCH₂), 3.51 (q, J=7 Hz, C$\underline{H}$₂CH₃), 4.52 (s, CH₂-pyridine), 7.30 (d, J=8 Hz, 1 H), 7.62 (dd, J=8 & 2 Hz, 1 H), 8.33 (d, J=2 Hz, 1 H)

(3) Title compound (white—pale yellow crystals)

m.p.: 132–133° C.

NMR (CDCl₃) δ: 1.33 (t, J=7 Hz, CH₂C$\underline{H}$₃), 2.80 (s, MeN), 3.38 (dq, J=5 & 7 Hz, C$\underline{H}$₂CH₃), 4.40 (s, CH₂-pyridine), 6.49 (s, =CHNO₂), 7.38 (d, J=8 Hz, 1 H), 7.59 (dd, J=8 & 2 Hz, 1 H), 8.30 (d, J=2 Hz, 1 H), 9.51 (br t, J=5 Hz, NH)

IR (Nujol): 1600, 1535, 1445, 1305, 1290 cm⁻¹

Example 62

1-[N-(2,6-Dimethyl-4-pyridylmethyl)-N-methyl] amino-1-methylamino-2-nitroethylene (Compound 81)

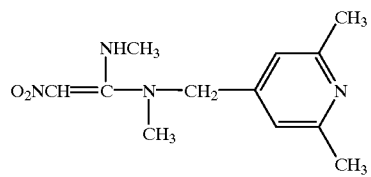

The steps (1), (2) and (3) of Example 13 were repeated except that N-(2,6-dimethyl-4-pyridylmethyl)-N- methylamine was used in lieu of N-ethyl-N-(3-pyridylmethyl)amine to give the following compounds in the respective steps.

(1) N-(2,6-dimethyl-4-pyridylmethyl)-N-methyl-N'-methylthiourea (white crystals)

m.p.: 207–208° C.

NMR (CDCl$_3$) δ: 2.49 (s, pyridine-Me×2), 3.09 (s, MeNCH$_2$), 3.18 (d, J=5 Hz, MeNH), 5.10 (s, CH$_2$-pyridine), 5.91 (br q, J=5 Hz, NH), 6.86 (s, pyridine-H$_2$)

(2) S-Methyl-N-(2,6-dimethyl-4-pyridylmethyl)-N-methyl-N'-methylisothiourea (brown oil)
(provide, however, that after addition of 60% sodium hydride (oil), the mixtrue was stirred at 50° C. for 1 hour and at reflux temperature for 1 hours.)

NMR (CDCl$_3$) δ: 2.30 (s, MeS), 2.50 (s, pyridien-Me×2), 2.86 (s, MeNH), 3.27 (s, MeN=), 4.53 (s, pyridine-CH$_2$), 6.84 (s, pyridine-H$_2$)

(3) Title compound (white crystals)

m.p.: 131–133° C.

NMR (CDCl$_3$) δ: 2.53 (s, pyridine-Me×2), 2.87 (s, MeNCH$_2$), 3.05 (d, J=5 Hz, MeNH), 4.34 (s, CH$_2$), 6.54 (s, =CHNO$_2$), 6.83 (s, pyridine-H$_2$)

IR (Nujol): 1570, 1460, 1395, 1310, 1230 cm$^{-1}$

Example 63

1-[N-(2-chloro-3-pyridylmethyl)-N-methyl]amino-1-methylamino-2-nitroethylene (Compound 82)

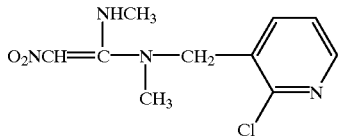

The steps (1), (2) and (3) of Example 13 were repeated except that N-(2-chloro-3-pyridylmethyl)-N-methylamine was used in lieu of N-ethyl-N-(3-pyridylmethyl)amine to give the following compounds in the respective steps.

(1) N-(2-chloro-3-pyridylmethyl)-N-methyl-N'-methylthiourea (white crystals)

m.p.: 143–144° C.

NMR (CDCl$_3$) δ: 3.17 (s, MeNCH$_2$), 3.18 (d, J=5 Hz, MeNH), 5.29 (s, CH$_2$), 5.98 (br q, J=5 Hz, NH), 7.26 (dd, J=8 & 5 Hz, 1 H), 7.66 (d, J=8 & 1 Hz, 1 H), 8.31 (dd, J=5 & 1 Hz, 1 H)

(2) S-Methyl-N-(2-chloro-3-pyridylmethyl)-N-methyl-N'-methylisothiourea (pale yellow oil)
(provided, however, that after addition of 60% sodium hydride (oil), the mixture was stirred at 50° C. for 1 hour.)

NMR (CDCl$_3$) δ: 2.29 (s, MeS), 2.95 (s, MeNCH$_2$), 3.26 (s, MeN=), 4.67 (s, CH$_2$-pyridine), 7.24 (dd, J=8 & 5 Hz, 1 H), 7.62 (dd, J=8 & 1 Hz, 1 H), 8.32 (dd, J=5 & 1 Hz, 1 H)

(3) Title compound (pale yellow crystals)
(provided, however, that the reaction mixture was refluxed in nitromethane for 2.25 hours)

As determined by NMR, the purity of this product was found to be about 75%.

m.p.: 106–113° C.

NMR (CDCl$_3$) δ: (for the title compound only) 2.90 (s, MeNCH$_2$), 3.04 (d, J=5 Hz, MeNH), 4.50 (s, CH$_2$), 6.54 (s, =CHNO$_2$), 7.37 (dd, J=8 & 5 Hz), 7.68 (dd, J=8 & 1 Hz), 8.43 (dd, J=5 & 1 Hz), 9.78 (br q, J=5 Hz, NH)

IR (Nujol): 1560, 1450, 1405, 1310, 1260 cm$^{-1}$

Example 64

1-(6-Chloro-3-pyridylmethyl)amino-1-methylamino-1-methylamino-2-nitroethylene (Compound 25)

The steps (1), (2) and (3) of Example 8 were repeated except that 6-chloro-3-pyridylmethylamine was used in lieu of N-methyl-N-3-pyridylmethylamine to give the following compounds in the respective steps.

(1) N-(6-Chloro-3-pyridylmethyl)-N'-methylthiourea (white crystals)

m.p.: 133–134° C.

NMR (CDCl$_3$) δ: 3.01 (d, J=5 Hz, Me), 4.80 (d, J=6 Hz, CH$_2$), 7.25 (br, NHCH$_3$), 7.32 (d, J=8 Hz, 1 H), 7.66 (br t, J=6 Hz, NHCH$_2$), 7.78 (dd, J=8 & 2 Hz, 1H), 8.37 (d, J=2 Hz, 1 H)

(2) S-Methyl-N-(6-chloro-3-pyridylmethyl)-N'-methylisothiourea (oil)

NMR (CDCl$_3$) δ: 2.39 (s, MeS), 2.93 (s, MeN), 4.22 (br, NH), 4.50 (s, CH$_2$), 7.27 (d, J=8 Hz, 1 H), 7.69 (dd, J=8 & 2 Hz, 1 H), 8.39 (d, J=2 Hz, 1 H)

(3) Title compound (white—pale yellow crystals)
This product was found to be in agreement with Compound 28 according to Example 10 in melting point, NMR, IR and TLC Rf.

Example 65

1-Methylamino-1-[N-methyl-N-(2-thiazolyl)]amino-2-nitroethylene (Compound 83)

The steps (1), (2) and (3) of Example 59 were repeated except that 2-methylaminothiazole was used in lieu of 2-chloro-5-methylaminopyridine to obtain the following compounds in the respective steps.

(1) N-Methyl-N'-methyl-N'-(2-thiazolyl)thiourea (white crystals)
(provided that the reaction mixture was refluxed in toluene for 8 hours and the product was purified by silica gel column chromatography)

m.p.: 68–69° C.

NMR (CDCl$_3$) δ: 3.24 (d, J=4 Hz, 3 H), 3.95 (s, 3 H), 6.69 (d, J=4 H, 1 H), 7.42 (d, J=4 Hz, 1 H), 11.95 (br, 1 H)

(2) S-Methyl-N-methyl-N'-methyl-N'-(2-thiazolyl) isothiourea (pale yellow oil)

NMR (CDCl$_3$) δ: 2.33 (s, 3 H), 3.41 (s, 3 H), 3.75 (s, 3 H), 6.74 (d, J=4 Hz, 1 H), 7.40 (d, J=4 Hz, 1 H)

(3) Title compound (pale yellow crystals)
(provided that the reaction was conducted for 25 hours and the product was concentrated to give crystals)

m.p.: 155–156° C.

NMR (CDCl$_3$): 2.98 (d, J=5 Hz, 3 H), 3.42 (s, 3 H), 6.71 (s, 3 H), 6.91 (d, J=4 Hz, 1 H), 7.36 (d, J=4 Hz, 1 H), 9.87 (br, 1 H)

IR (Nujol): 3050, 1610, 1500, 1400, 1320, 1260, 1100, 1010 cm$^{-1}$

Example 66

1-Methylamino-1-[N-methyl-N-(6-methyl-3-pyridyl)]amino-2-nitroethylene (Compound 84)

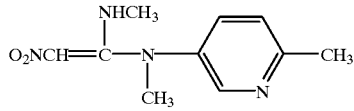

(1) In a solution of 1.9 g NaOH in 30 ml water was dissolved 4.3 g (0.02 mole) of 2-methyl-5-methylaminopyridine oxalate and the solution was extracted with AcOEt (50 ml, 30 ml×2). The AcOEt layers were combined, washed with water and dried over MgSO$_4$. After concentration, 30 ml of toluene and 1.8 g of methyl isothiocyanate were added to the concentrate and the mixture was refluxed for 8 hours. Then, 0.8 g of methyl isothiocyanate was further added and the mixture was refluxed for 7.5 hours. The reaction mixture was cooled to −20° C. and the resulting crystals were collected by filtration, washed with cold toluene and dried. The procedure gave 2.2 g of N-methyl-N'-methyl-N'-(6-methyl-3-pyridyl)thiourea as white crystals.

m.p.: 134–135° C.

NMR (CDCl$_3$) δ: 2.62 (3 H, s), 3.06 (3 H, d, J=4.2 Hz), 3.66 (3 H, s), 5.2–5.9 (1 H, m, NH), 7.30 (1 H, d, J=8.4 Hz), 7.49 (1 H, dd, J=8.4 & 2.7 Hz), 8.42 (1 H, d, J=2.7 Hz)

(2) The reaction procedure of Example 59 (2) was repeated except that N-methyl-N'-methyl-N'-(6-methyl-3-pyridyl)thiourea was used in lieu of N-(6-chloro-3-pyridyl)-N-methyl-N'-methylthiourea to give S-methyl-N-methyl-N'-methyl-N'-(6-methyl-3-pyridyl)isothiourea as oil.

NMR (CDCl$_3$) δ: 2.01 & 2.37 (3 H, each s), 2.49 & 2.53 (3 H, each s), 3.04 & 3.17 & 3.24 & 3.30 (6 H, each s), 6.9–7.6 (2 H, m), 8.0–8.5 (1 H, m)

(3) The reaction procedure of Example 59 (3) was repeated except that S-methyl-N-methyl-N'-methyl-N'-(6-methyl-3-pyridyl)isothiourea was used in lieu of S-methyl-N-(6-chloro-3-pyridyl)-N-methyl-N'-methylisothiourea and that the reaction was conducted for 23 hours. The procedure gave the title compound as yellow-brown crystals.

m.p.: 120–121° C.

NMR (CDCl$_3$) δ: 2.57 (3 H, s), 2.65 (3 H, d, J=5.4 Hz), 3.30 (3 H, s), 6.67 (1 H, s), 7.23 (1 H, d, J=8.7 Hz), 7.39 (1 H, dd, J=8.4 & 2.7 Hz), 8.38 (1 H, d, J=2.7 Hz), 9.7–10.4 (1 H, m, NH)

IR (Nujol): 3110, 1600 cm$^{-1}$

Example 67

1-[N-(6-chloro-3-pyridyl)-N-methyl]amino-1-ethylamino-2-nitroethylene (Compound 85)

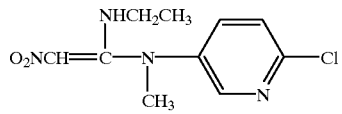

The steps (1), (2) and (3) of Example 59 were repeated except that ethyl isothiocyanate was used in lieu of methyl isothiocyanate to give the following compounds in the respective steps.

(1) N-(6-Chloro-3-pyridyl)-N-methyl-N'-ethylthiourea (yellow oil)

(provided that the reaction mixture was refluxed in toluene for 78 hours and the product was purified by silica gel column chromatography)

NMR (CDCl$_3$) δ: 1.13 (3 H, t, J=6.6 Hz), 3.4–3.9 (2 H, m), 3.63 (3 H, s), 5.0–5.8 (1 H, br), 7.46 (1 H, d, J=8.4 Hz), 7.61 (1 H, dd, J=8.4 & 2.7 Hz), 8.33 (1 H, d, J=2.7 Hz)

(2) S-Methyl-N-(6-chloro-3-pyridyl)-N-methyl-N'-ethylisothiourea (yellow oil)

NMR (CDCl$_3$) δ: [main component . . . 76%] 1.23 (3 H, t, J=7.2 Hz), 2.04 (3 H, s), 3.28 (3 H, s), 3.53 (2 H, q, J=7.2 Hz), 6.9–7.6 (2 H, m), 8.22 (1 H, d, J=2.7 Hz) [a small amount of isomer . . . 24%], 2.73 (3 H, s), 3.13 (3 H, s), 3.1–3.4 (2 H, m), 7.89 (1 H, d, J=2.7 Hz)

(3) Title compound (pale yellow crystals)

(provided that the reaction was conducted for 64 hours and the reaction mixture was concentrated to give crystals)

m.p.: 118–119° C.

NMR (CDCl$_3$) δ: 1.19 (3 H, t, J=7.5 Hz), 3.00 (2 H, dt, J=7.5 & 6.3 Hz), 3.29 (3 H, s), 6.61 (1 H, s), 7.3–7.6 (2 H, m), 8.1–8.4 (1 H, m)

IR (Nujol): 3200, 1605, 1375, 1300 cm$^{-1}$

Example 68

1-[N-(5-Bromo-3-pyridylmethyl)-N-methyl]amino-1-methylamino-2-nitroethylene (Compound 86)

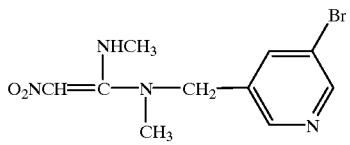

The steps (1), (2) and (3) of Example 13 were repeated except that crude N-(5-bromo-3-pyridylmethyl)-N-methylamine was used in lieu of N-ethyl-N-(3-pyridylmethyl)amine to give the following compounds in the respective steps.

(1) N-(5-Bromo-3-pyridylmethyl)-N-methyl-N'-methylthiourea (pale yellow oil)

(provided that the product was purified by silica gel column chromatography)

NMR (CDCl$_3$) δ: 3.05 (s, MeNCH$_2$), 3.19 (d, J=5 Hz, MeNH), 5.24 (s, CH$_2$), 5.88 (br q, J=5 Hz, NH), 7.91 (m, 1 H), 8.47 (d, J=2 Hz, 1 H), 8.62 (d, J=2 Hz, 1 H)

(2) S-Methyl-N-(5-bromo-3-pyridylmethyl)-N-methyl-N'-methylisothiourea (oil)

NMR (CDCl$_3$) δ: 2.31 (s, MeS), 2.88 (s, MeNCH$_2$), 3.26 (s, MeN=), 4.56 (s, CH$_2$), 7.77 (m, 1 H), 8.47 (d, J=2 Hz, 1 H), 8.60 (d, J=2 Hz, 1 H)

(3) Title compound (pale yellowish brown crystals)

m.p.: 116–117° C.

NMR (CDCl$_3$) δ: 2.84 (s, MeNCH$_2$), 3.08 (d, J=5 Hz, MeNH), 4.42 (s, CH$_2$), 6.54 (s, =CHNO$_2$), 7.76 (m, 1 H), 8.48 (d, J=2 Hz, 1H), 8.68 (d, J=2 Hz, 1 H), 9.72 (br q, J=5 Hz, NH)

IR (Nujol): 1595, 1465, 1425, 1405, 1260 cm$^{-1}$

Example 69

1-Methylamino-1-[N-methyl-N-(2-methylthio-3-pyridylmethyl)]amino-2-nitroethylene (Compound 87)

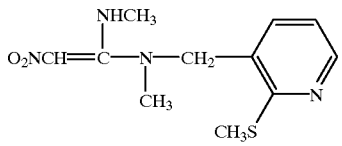

The steps (1), (2) and (3) of Example 13 were repeated except that N-(2-methylthio-3-pyridylmethyl)-N-methylamine was used in lieu of N-ethyl-N-(3-pyridylmethyl)amine to give the following compounds in the respective steps.

(1) N-Methyl-N'-methyl-N'-(2-methylthio-3-pyridylmethyl)thiourea (white—pale yellow crystals)
m.p.: 105–106° C.
NMR (CDCl$_3$) δ: 2.61 (s, MeS), 3.15 (d, J=5 Hz, MeNH), 3.17 (s, MeNCH$_2$), 5.00 (s, CH$_2$), 5.77 (br, NH), 7.01 (dd, J=8 & 5 Hz, 1 H), 7.36 (dd, J=8 & 1 Hz, 1 H), 8.40 (dd, J=5 & 1 Hz, 1 H)

(2) S-Methyl-N-methyl-N'-methyl-N'-(2-methylthio-3-pyridylmethyl)isothiourea (yellow oil)
NMR (CDCl$_3$) δ: 2.28 (s, MeS), 2.59 (s, pyridine-SMe), 2.89 (s, MeNCH$_2$), 3.27 (s, MeN=), 4.53 (s, CH$_2$), 6.98 (dd, J=8 & 5 Hz, 1 H), 7.40 (dd, J=8 & 1 Hz, 1 H), 8.37 (dd, J=5 & 1 Hz, 1 H)

(3) Title compound (pale yellow crystals)
m.p.: 131–132° C.
NMR (CDCl$_3$) δ: 2.60 (s, MeS), 2.84 (s, MeNCH$_2$), 3.03 (d, J=5 Hz, MeNH), 4.34 (s, CH$_2$), 6.57 (s, =CHNO$_2$), 7.07 (dd, J=8 & 5 Hz, 1 H), 7.43 (dd, J=8 & 1 Hz, 1 H), 8.46 (dd, J=5 & 1 Hz, 1 H)
IR (Nujol): 1600, 1530, 1395, 1375, 1245 cm$^{-1}$

Example 70

1-Methylamino-1-[N-methyl-N-(4-thiazolyl)methyl]amino-2-nitroethylene (Compound 88)

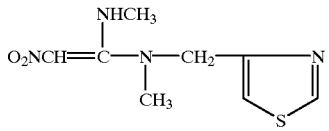

The steps (1), (2) and (3) of Example 13 were repeated except that N-methyl-N-(4-thiazolyl)methylamine was used in lieu of N-ethyl-N-(3-pyridylmethyl)amine to give the following compounds in the respective steps.

(1) N-Methyl-N'-methyl-N'-(4-thiazolylmethyl)thiourea (oil, crystallized on standing in a refrigerator)
(provided that the product was purified by silica gel column chromatography)
NMR (CDCl$_3$) δ: 3.15 (d, J=5 Hz, MeNH), 3.30 (s, MeNCH$_2$), 4.98 (s, CH$_2$), 6.87 (br, NH), 7.38 (d, J=2 Hz, 1 H), 8.81 (d, J=2 Hz, 1 H)

(2) S-Methyl-N-methyl-N'-methyl-N'-(4-thiazolylmethyl)isothiourea (oil)
NMR (CDCl$_3$) δ: 2.31 (s, MeS), 2.91 (s, MeNCH$_2$), 3.27 (s, MeN=), 4.79 (s, CH$_2$), 7.17 (m, 1 H), 8.80 ((, J=2 Hz, 1 H)

(3) Title compound (yellow crystals)
(provided that the reaction was conducted for 4.5 hours)
m.p.: 155–156° C.
NMR (DMSO-d$_6$) δ: 2.89 (s, MeNCH$_2$), 2.98 (d, J=5 Hz, MeNH), 4.60 (s, CH$_2$), 6.55 (s, =CHNO$_2$), 7.70 (d, J=2 Hz, 1 H), 8.95 (br q, J=5 Hz, 1 H), 9.12 (d, J=2 Hz, 1 H)
IR (Nujol): 1580, 1530, 1290, 1270, 1255 cm$^{-1}$

Example 71

1,1-bis(6-Chloro-3-pyridylmethyl)amino-2-nitroethylene (Compound 89)

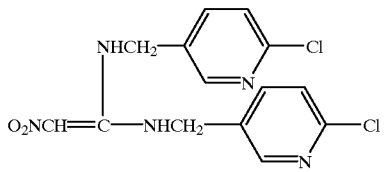

(1) A mixture of 7.0 g (0.042 mole) of 1,1-bis(methylthio)-2-nitroethylene, 4.5 g of N,O-dimethylhydroxyamine hydrochloride and 80 ml of EtOH was refluxed and 6.4 ml of Et$_3$N was added dropwise over 1 hour. After completion of dropwise addition, the mixture was further refluxed for 2 hours. The reaction mixture was then concentrated and the resulting crystals were filtered off. The filtrate was concentratd and the residue was subjected to silica gel column chromatography using EtOH-CHCl$_3$ (1:30) as the eluent. The procedure gave 1.0 g of 1-(N-methyl-N-meythoxy)amino-1-methylthio-2-nitroethylene as a yellow oil.
NMR (CDCl$_3$) δ: 2.43 (3 H, s), 3.26 (3 H, s), 3.68 (3 H, s), 7.16 (1H,s)

(2) A mixture of 0.8 g (0.0045 mole) of 1-(N-methyl-N-methoxy)amino-1-methylthio-2-nitroethylene, 0.7 g of (6-chloro-3-pyridylmethyl)amine and 30 ml of EtOH was refluxed for 4 hours. The resulting crystals were collected by filtration and dried to give 150 mg of the title compound as crystals.
m.p.: 238–240° C. (decompn.)
NMR (DMSO-d$_6$) δ: 4.53 (4 H, d, J=5.7 Hz), 6.51 (1 H, s), 7.50 (2 H, d, J=8.7 Hz), 7.76 (2 H, dd, J=8.7 & 2.4 Hz), 8.37 (2 H, d, J=2.4 Hz), 9.7–10.8 (2 H, br)
IR (Nujol): 3240, 1620, 1575, 1460, 1395, 1220 cm$^{-1}$

Example 72

1-[N-(6-Chloro-3-pyridyl)-N-ethyl]amino-1-methylamino-2-nitroethylene (Compound 90)

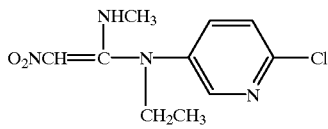

(1) In 30 ml of toluene was dissolved 2.4 g (0.015 mole) of 2-chloro-5-ethylaminopyridine, followed by addition of 3.4 g of methyl isocyanate. The mixture was refluxed for 15 hours. After cooling, the resulting crystals were collected by filtration, washed with a small amount of Et$_2$O and dried. The procedure gave 3.0 g of N-(6-chloro-3-pyridyl)-N-ethyl-N'-methylurea as pale yellow crystals.

m.p.: 135–136° C.

NMR (CDCl₃) δ: 1.11 (t, J=7 Hz, 3 H), 2.75 (d, J=5 Hz, 3 H), 3.72 (q, J=7 Hz, 2 H), 4.36 (br, 1 H), 7.40 (d, J=8 Hz, 1 H), 7.59 (dd, J=8 & 3 Hz, 1 H), 8.28 (d, J=3 Hz, 1 H)

(2) In 30 ml of CH₃CN was dissolved 1.5 g (0.007 mole) of N-(6-chloro-3-pyridyl)-N-ethyl-N'-methylurea, followed by addition of 3.1 g of phosphorus pentasulfide. The mixture was refluxed for 3 hours. The insoluble matter was then filtered off and the filtrate was concentrated and diluted with 20 ml of water. The mixture was neutralized with NaHCO₃ and extracted with CH₂Cl₂ (50 ml×3) and the extract was dried over MgSO₄. After concentration, the residue was purified by silica gel column chromatography to recover 0.52 g of N-(6-chloro-3-pyridyl)-N-ethyl-N'-methylthiourea as pale yellow crystals.

m.p.: 110–111° C.

NMR (CDCl₃) δ: 1.20 (t, J=7 Hz, 3 H), 3.06 (d, J=5 Hz, 3 H), 4.22 (q, J=7 Hz, 2 H), 5.42 (br, 1 H), 7.40–7.70 (m, 2 H), 8.28 (d, J=3 Hz, 1 H)

(3) The reaction procedure of Example 59 (2) was repeated except that N-(6-chloro-3-pyridyl)-N-ethyl-N'-methylthiourea was used in lieu of N-(6-chloro-3-pyridyl)-N-methyl-N'-methylthiourea to give S-methyl-N-(6-chloro-3-pyridyl)-N-ethyl-N'-methylisothiourea as a pale yellow oil.

NMR (CDCl₃) δ: 1.06–1.43 (m, 3 H), 2.02 & 2.39 (each s, 3 H), 3.03 & 3.30 (each s, 3 H), 3.46–3.93 (m, 2 H), 6.90–7.53 (m, 2 H), 7.88 & 8.20 (each d, J=3 Hz, 1 H)

(4) The reaction procedure of Example 59 (3) was repeated except that S-methyl-N-(6-chloro-3-pyridyl)-N-ethyl-N'-methylisothiourea was used in lieu of S-methyl-N-(6-chloro-3-pyridyl)-N-methyl-N'-methylisothiourea to give the title compound as pale yellow crystals.

m.p.: 95–96° C.

NMR (CDCl₃) δ: 1.23 (t, J=7 Hz, 3 H), 2.71 (d, J=5 Hz, 3 H), 3.75 (q, J=7 Hz, 2 H), 6.67 (s, 1 H), 7.26–7.53 (m, 2 H), 8.20 (d, J=3 Hz, 1 H), 10.05 (br, 1 H)

IR (Nujol): 3100, 1600, 1505, 1320, 1220, 1170, 1120, 1020 cm⁻¹

Example 73

1-[N-(6-Chloro-3-pyridyl)-N-n-propyl]amino-1-methylamino-2-nitroethylene (Compound 91)

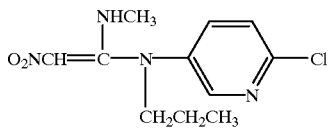

The steps (1), (2), (3) and (4) of Example 72 were repeated except that 2-chloro-5-n-propylaminopyridine was used in lieu of 2-chloro-5-ethylaminopyridine to obtain the following compounds in the respective steps.

(1) N-(6-Chloro-3-pyridyl)-N-n-propyl-N'-methylurea (pale yellow crystals)

m.p.: 84–85° C.

NMR (CDCl₃) δ: 0.87 (t, J=7 Hz, 3 H), 1.26–1.80 (m, 2 H), 2.75 (d, J=5 Hz, 3 H), 3.62 (t, J=7 Hz, 2 H), 4.40 (br, 1 H), 7.38 (d, J=8 Hz, 1 H), 7.66 (dd, J=8 & 3 Hz, 1 H), 8.28 (d, J=3 Hz, 1 H)

(2) N-(6-Chloro-3-pyridyl)-N-n-propyl-N'-methylthiourea (pale yellow crystals)

m.p.: 145–146° C.

NMR (CDCl₃) δ: 0.90 (t, J=7 Hz, 3 H), 1.40–1.93 (m, 2 H), 3.07 (d, J=5 Hz, 3 H), 4.12 (t, J=7 Hz, 2 H), 5.33 (br, 1 H), 7.40–7.70 (m, 2 H), 8.30 (d, J=3 Hz, 1H)

(3) S-Methyl-N-(6-chloro-3-pyridyl)-N-n-propyl-N'-methylisothiourea (pale yellow oil)

NMR (CDCl₃) δ: 0.80–1.10 (m, 3 H), 1.40–1.90 (m, 2 H), 2.01 & 2.37 (each s, 3 H), 3.00 & 3.28 (each s, 3 H), 3.36–3.83 (m, 2 H), 6.90–7.53 (m, 2 H), 7.86 & 8.18 (each d, J=3 Hz, 1H)

(4) Title compound (pale yellow crystals)

m.p.: 94–95°–C.

NMR (CDCl₃) δ: 0.95 (t, J=7 Hz, 3 H), 1.43–1.93 (m, 2 H), 2.68 (d, J=5 Hz, 3 H), 3.61 (t, J=7 Hz, 2 H), 6.69 (s, 1 H), 7.26–7.50 (m, 2 H), 8.21 (d, J=3 Hz, 1 H), 10.06 (br, 1 H)

IR (Nujol): 3100, 1590, 1520, 1360, 1310, 1225, 1120, 1020 cm⁻¹

Example 74

1-[N-n-Butyl-N-(6-chloro-3-pyridyl)]amino-1-methylamino-2-nitroethylene (Compound 92)

The steps (1), (2), (3) and (4) of Example 72 were repeated except that 2-chloro-5-n-butylaminopyridine was used in lies of 2-chloro-5-ethylaminopyridine to give the following compounds in the respective steps.

(1) N-n-Butyl-N-(6-chloro-3-pyridyl)-N'-methylurea (pale yellow oil)

NMR (CDCl₃) δ: 0.86–1.06 (m, 3 H), 1.10–1.73 (m, 4 H), 2.75 (d, J=5 Hz, 3 H), 3.66 (t, J=7 Hz, 2 H), 4.30 (d, J=5 Hz, 1 H), 7.40 (d, J=8 Hz, 1 H), 7.60 (dd, J=8 & 3 Hz, 1 H), 8.29 (d, J=3 Hz, 1 H)

(2) N-n-Butyl-N-(6-chloro-3-pyridyl)-N'-methylthiourea (pale yellow crystals)
(provided that the reaction was conducted in toluene for 1 hour)

m.p.: 129–130° C.

NMR (CDCl₃) δ: 0.90 (t, J=7 Hz, 3 H), 1.10–1.83 (m, 4 H), 3.07 (d, J=5 Hz, 3 H), 4.15 (t, J=7 Hz, 2 H), 5.52 (d, J=5 Hz, 1 H), 7.36–7.70 (m, 2 H), 8.25 (d, J=3 Hz, 1 H)

(3) S-Methyl-N-n-butyl-N-(6-chloro-3-pyridyl)-N'-methylisothiourea (pale yellow oil)

NMR (CDCl₃) δ: 0.80–1.06 (m, 3 H), 1.10–1.80 (m, 4 H), 2.00 & 2.36 (each s, 3 H), 3.00 & 3.27 (each s, 3 H), 3.42–3.82 (m, 2 H), 6.90–7.50 (m, 2 H), 7.86 & 8.18 (each d, J=3 Hz, 1 H)

(4) Title compound (pale yellow crystals)

m.p.: 87–88° C.

NMR (CDCl₃) δ: 0.93 (t, J=7 Hz, 3 H), 1.10–1.85 (m, 4 H), 2.68 (d, J=5 Hz, 3 H), 3.65 (t, J=7 Hz, 2 H), 6.69 (s, 1 H), 7.26–7.52 (m, 2 H), 8.21 (d, J=3 Hz, 1 H), 10.05 (br, 1 H)

IR (Nujol): 3100, 1590, 1520, 1360, 1310, 1250, 1120, 1020 cm⁻¹

Example 75

1-[N-(6-Chloro-3-pyridyl)-N-ethyl]amino-1-ethylamino-2-nitroethylene (Compound 93)

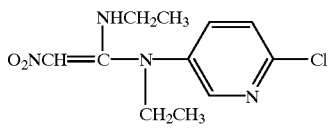

The steps (1), (2) and (3) of Example 59 were repeated except that 2-chloro-5-ethylaminopyridine and ethyl isothiocyanate were used in lieu of 2-chloro-5-methylaminopyridine and methyl isothiocyanate, respectively, to give the following compounds in the respective steps.

(1) N-(6-Chloro-3-pyridyl)-N-ethyl-N'-ethylthiourea (pale red crystals)
(provided that the reaction was conducted in toluene for 66 hours)
m.p.: 84–86° C.
NMR (CDCl$_3$) δ: 1.11 (3 H, t, J=7.1 Hz), 1.19 (3 H, t, J=7.2 Hz), 3.63 (2 H, dq, J=5.6 & 7.1 Hz), 4.21 (2 H, q, J=7.1 Hz), 4.9–5.5 (1 H, m, NH), 7.4–7.7 (2 H, m), 8.29 (1 H, d, J=2.4 Hz)

(2) S-Methyl-N-(6-chloro-3-pyridyl)-N-ethyl-N'-ethylisothiourea (oil)
NMR (CDCl$_3$) δ: 1.0–1.6 (6 H, m), 2.00 & 2.38 (3 H, each s,), 3.1–4.5 (4 H, m), 6.8–7.6 (2 H, m), 7.7–8.5 (1 H, m)

(3) Title compound (pale yellow crystals)
m.p: 105° C.
NMR (CDCl$_3$) δ: 1.0–1.5 (6 H, m), 2.94 (2 H, dq, J=5.2 & 7.0 Hz), 3.74 (2 H, q, J=7.1 Hz), 6.65 (1 H, s), 7.2–7.6 (2 H, m), 8.1–8.4 (1 H, m), 9.6–10.2 (1 H, m, NH)
IR (Nujol): 3110, 1600 cm$^{-1}$

Example 76

1-Methylamino-1-[N-methyl-N-(5-trifluoromethyl-3-pyridyl)]amino-2-nitroethylene (Compound 94)

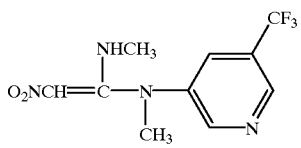

(1) The reaction procedure of Example 59 (1) was repeated except that 3-methylamino-5-trifluoromethylpyridine was used in lieu of 2-chloro-5-methylaminopyridine (refluxed in toluene for 61.5 hours) to give N-methyl-N'-methyl-N'-(5-trifluoromethyl-3-pyridyl) thiourea as pale brown crystals.
m.p.: 86–90° C.
NMR (CDCl$_3$) δ: 3.12 (3 H, d, J=4.2 Hz), 3.67 (3 H, s), 5.3–5.8 (1 H, m, NH), 7.8–8.0 (1 H, m), 8.77 (1 H, d, J=2.4 Hz), 8.88 (1 H, br s)

(2) A mixture of 0.2 g (0.0008 mole) of N-methyl-N'-methyl-N'-(5-trifluoromethyl-3-pyridyl)thiourea, 0.3 g of methyl iodide and 10 ml of CH$_3$CN was stirred at room temperature for 13.5 hours. Then, 0.3 g of methyl iodide was further added and the mixture was stirred for 18.5 hours. The reaction mixture was concentrated and the residue was diluted with 50 ml of AcOEt and aqueous sodium hydrogen carbonate solution. After shaking, the mixture was subjected to phase separation. The AcOEt layer was washed with aqueous sodium chloride solution, dried over MgSO$_4$ and concentrated. The procedure gave 0.2 g of crude S-methyl-N-methyl-N'-methyl-N'-(5-trifluoromethyl-3-pyridyl) isothiourea as oil.

(3) A mixture of 0.2 g of crude S-methyl-N-metyl-N'-methyl-N'-(5-trifluoromethyl-3-pyridyl)isothiourea and 10 ml of CH$_3$NO$_2$ was refluxed for 36.5 hours. The reaction mixture was concentrated and the residue was subjected to silica gel column chromatography using hexane-acetone (2:1) as the eluent. The procedure gave 18 mg of the title compound as yellow-brown crystals.
m.p: 114–115° C.
NMR (CDCl$_3$) δ: 2.81 (3 H, d, J=5.1 Hz), 3.36 (3 H, s), 6.63 (1 H, s), 7.5–7.7 (1 H, m), 8.5–8.7 (2 H, m), 9.6–10.1 (1 H, m, NH)

Example 77

1-[N-(6-Chloro-3-pyridyl)-N-methyl]amino-1-n-propylamino-2-nitroethylene (Compound 95)

The steps (1), (2) and (3) of Example 59 were repeated except that n-propyl isothiocyanate was used in lieu of methyl isothiocyanate to give the following compounds in the respective steps.

(1) N-(6-Chloro-3-pyridyl)-N-methyl-N'-n-propylthiourea (yellow oil)
(provided that the reaction mixture was refluxed in toluene for 121 hours and the product was purified by silica gel column chromatography)
NMR (CDCl$_3$) δ: 0.86 (3 H, t, J=6.6 Hz), 1.2–1.8 (2 H, m), 3.63 (3 H, s), 3.4–3.9 (2 H, m), 5.1–5.7 (1 H, br), 7.45 (1 H, d, J=8.4 Hz), 7.61 (1 H, dd, J=8.4 & 2.7 Hz), 8.34 (1 H, d, J=2.7 Hz)

(2) S-Methyl-N-(6-chloro-3-pyridyl)-N-methyl-N'-n-propylisothiourea (yellow oil)
NMR (CDCl$_3$) δ: [major component . . . 74%]0.96 (3 H, t, J=7.5 Hz), 1.3–1.9 (2 H, m), 2.03 (3 H, s), 3.28 (3 H, s), 3.47 (2 H, t, J=7.5 Hz), 7.25 (1 H, d, J=8.4 Hz), 7.45 (1 H, dd, J=8.4 & 2.7 Hz), 8.23 (1 H, d, J=2.7 Hz) [minor component (isomer) . . . 26%] 2.38 (3 H, s), 3.14 (3 H, s), 3.0–3.4 (2 H, m), 6.9–7.4 (2 H, m)

(4) Title compound (oil)
NMR (CDCl$_3$) δ: 0.93 (3 H, t, J=7.2 Hz), 1.59 (2 H, tq, J=7.2 & 7.2 Hz), 2.95 (2 H, dt, J=6.0 & 7.2 Hz), 3.30 (3 H, s), 6.60 (1 H, s), 7.2–7.6 (2 H, m), 8.23 (1 H, d, J=3.0 Hz), 9.6–10.1 (1 H, br)
IR (neat): 3110, 2950, 1595, 1450, 1360 cm$^{-1}$

Example 78

1-(6-Chloro-3-pyridyl)amino-1-methylamino-2-nitroethylene (Compound 96)

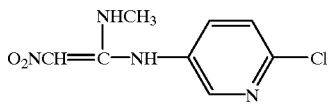

(1) A mixture of 3.9 g (0.0303 mole) of 5-amino-2-chloropyridine, 5.0 g of 1,1-bis(methylthio)-2-nitroethylene and 80 ml of ethylbenzene was heated at 130° C. for 2 hours. The ethylbenzene was distilled off under reduced pressure and the crystalline residue was washed with AcOEt and subjected to silica gel column chromatography using EtOH-CHCl$_3$ (1:30) as the eluent to recover crude crystals. These crystals were recrystallized from AcOEt, washed with ether and dried. The procedure gave 0.5 g of 1-(6-chloro-3-pyridyl)amino-1-methylthio-2-nitroethylene as pale yellow crystals.

m.p.: 169–171° C.

MNR (CDCl$_3$) δ: 2.42 (3 H, s), 6.70 (1 H, s), 7.41 (1 H, d, J=9.0 Hz), 7.65 (1 H, dd, J=9.0 & 2.4 Hz), 8.41 (1 H, d, J=2.4 Hz), 11.3–11.8 (1 H, br)

(2) In 25 ml of EtOH was dissolved 0.42 g (0.00171 mole) of 1-(6-chloro-3-pyridyl)amino-1-methylthio-2-nitroethylene, followed by addition of 0.2 g of a 40% solution of methylamine in methanol. The mixture was refluxed for 1.5 hours. The solvent was distilled off and the crystalline residue was washed with AcOEt and dried to recover 0.33 g of the title compound as white crystals.

m.p.: 185° C. (decompn.)

NMR (DMSO-d$_6$) δ: 2.94 (3 H, d, J=5.4 Hz), 6.24 (1 H, s), 7.57 (1 H, d, J=9.0 Hz), 7.80 (1 H, dd, J=9.0 & 2.7 Hz), 8.34 (1 H, d, J=2.7 Hz), 8.8–9.7 (1 H, br), 9.2–10.3 (1 H, br)

IR (Nujol): 3150, 1635, 1210 cm$^{-1}$

Example 79

1-Methylamino-1-[N-methyl-N-(6-methyl-3-pyridylmethyl)]amino-2-nitroethylene (Compound 97)

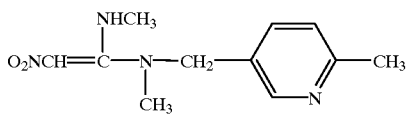

The steps (1), (2) and (3) of Example 13 were repeated except that crude N-methyl-N-(6-methyl-3-pyridylmethyl)amine was used in lieu of N-ethyl-N-(3-pyridylmethyl)amine to give the following compounds in the respective steps.

(1) N-Methyl-N'-methyl-N'-(6-methyl-3-pyridylmethyl)thiourea (pale pink crystals)

m.p.: 120–122° C.

NMR (CDCl$_3$) δ: 2.53 (s, pyridine-Me), 3.06 (s, MeNCH$_2$), 3.16 (d, J=5 Hz, MeNH), 5.16 (s, CH$_2$), 6.14 (br q, J=5 Hz, NH), 7.15 (d, J=8 Hz, 1 H), 7.64 (dd, J=8 & 2 Hz, 1H), 8.40 (d, J=2 Hz, 1H)

(2) S-Methyl-N-methyl-N'-methyl-N'-(6-methyl-3-pyridylmethyl)isothiourea (oil)

NMR (CDCl$_3$) δ: 2.31 (s, MeS), 2.53 (s, pyridine-Me), 2.81 (s, MeNCH$_2$), 3.25 (s, NeN=), 4.53 (S, CH$_2$), 7.11 (d, J=8 Hz, 1 H), 7.48 (dd, J=8 & 2 Hz, 1 H), 8.40 (d, J=2 Hz, 1 H)

(3) Title compound (yellow crystals)

m.p.: 102–103° C.

NMR (CDCl$_3$) δ: 2.57 (s, pyridine-Me), 2.80 (s, MeNCH$_2$), 3.08 (d, J=5 Hz, MeNH), 4.39 (s, CH$_2$), 6.54 (s, =CHNO$_2$), 7.21 (c, J=8 Hz, 1 H), 7.48 (dd, J=8 & 2 Hz, 1 H), 9.78 (br, NH)

IR (Nujol): 1600, 1550, 1310, 1250, 1090 cm$^{-1}$

Example 80

1-[N-(6-Fluoro-3-pyridylmethyl)-N-methyl]amino-1-methylamino-2-nitroethylene (Compound 98)

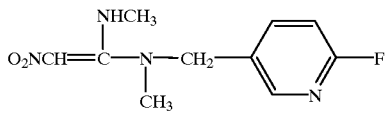

The steps (1), (2) and (3) of Example 13 were repeated except that crude N-(6-fluoro-3-pyridylmethyl)-N-methylamine was used in lieu of N-ethyl-N-(3-pyridylmethyl)amine to give the following compounds in the respective steps.

(1) N-(6-Fluoro-3-pyridylmethyl)-N-methyl-N'-methylthiourea (colorless oil)

(provided that the reaction was conducted in CHCl$_3$ overnight and the product was purified by silica gel column chromatography)

NMR (CDCl$_3$) δ: 3.04 (3 H, s, MeNCH$_2$), 3.18 (3 H, d, MeNH), 5.22 (2 H, s, CH$_2$), 6.88 (1 H, br, NH), 7.93 (1 H, dd, J=8.4 & 2.7 Hz), 8.54 (1 H, ddd, J=8.4, 2.4 & 8.4 Hz), 8.15 (1 H, d, J=2.4 Hz)

(2) S-Methyl-N-(6-fluoro-3-pyridylmethyl)-N-methyl-N'-methylisothiourea (oil)

NMR (CDCl$_3$) δ: 2.30 (3 H, s, MeS), 2.83 (3 H, s, MeNCH$_2$), 3.24 (3 H, s, MeN=), 4.53 (2 H, s, CH$_2$), 6.90 (1 H, dd), 7.72 (1 H, ddd), 8.12 (1 H, d)

(3) Title compound (pale brown crystals)

m.p.: 100–100.5° C.

NMR (CDCl$_3$) δ: 2.78 (3 H, s, MeNCH$_2$), 3.07 (3 H, d, MeNH), 4.39 (2 H, s, CH$_2$), 6.52 (1 H, s, =CHNO$_2$), 7.00 (1 H, dd, J=8.4 & 2.7 Hz), 7.71 (1 H, ddd, J=8.4, 2.4 & 8.4 Hz), 8.14 (1 H, d, J=2.4 Hz), 9.74 (1 H, br, NH)

IR (Nujol): 1593, 1548, 1477, 1465, 1437, 1405, 1390, 1310, 1250, 1230, 1165, 1083, 1029 cm$^{-1}$

Example 81

1-[N-Ethyl-N-(6-fluoro-3-pyridylmethyl)]amino-1-methylamino-2-nitroethylene (Compound 99)

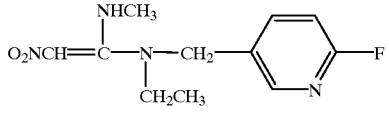

(1) In 30 ml CH$_3$CN was dissolved 4.2 g of 70% aqueous ethylamine solution and 3.0 g (0.016 mole in terms of pure product) of crude (6-fluoro-3-pyridyl)methyl bromide was added bropwise thereto under ice-cooling. The mixture was allowed to stand at room temperature overnight and the CH₃CN was distilled off. The residue was diluted with 20 ml of water and extracted with CHCl₃ (30 ml). The extract was dried over MgSO₄ and the CHCl₃ was distilled off to recover 1.38 g of red oil. This oil was dissolved in 30 ml of CHCl₃, followed by addition of 0.68 g of methyl isothiocyanate. The mixture was stirred at room temperature for 3 hours. The reaction mixture was treated with activated carbon and concentrated and the residue was subjected to silica gel column chromatography using AcOEt-hexane (3.5:1) as the eluent. The procedure gave 0.6 g of N-ethyl-N-(6-fluoro-3-pyridylmethyl)-N'-methylthiourea as colorless crystals.

m.p.: 123–124° C.

NMR (CDCl₃) δ: 1.18 (3 H, t, CH₂C<u>H</u>₃), 3.19 (3 H, d, Me<u>NH</u>), 3.48 (2 H, q, C<u>H</u>₂CH₃), 5.15 (2 H, s, pyridine-CH₂), 5.70 (1 H, br, NH), 6.92 (1 H, dd, J=8.4 & 2.7 Hz), 7.96 (1 H, ddd, J=8.4, 2.4 & 8.4 Hz), 8.15 (1 H, d, J=2.4 Hz)

(2) The reaction procedure of Example 13 (2) was repeated except that N-ethyl-N-(6-fluoro-3-pyridylmethyl)-N'-methylthiourea was used in lieu of N-methyl-N'-ethyl-N'-(3-pyridylmethyl)thiourea to give S-methyl-N-ethyl-N-(6-fluoro-3-pyridylmethyl)-N'-methylisothiourea as a pale brown oil.

NMR (CDCl₃) δ: 1.08 (3 H, t, CH₂C<u>H</u>₃)₁ 2.29 (3 H, s, MeS), 3.22 (3 H, s, MeN=), 3.36 (2 H, q, C<u>H</u>₂CH₃), 4.49 (2 H, s, CH₂), 6.87 (1 H, dd), 7.71 (1 H, ddd), 8.11 (1 H, d)

(3) The reaction procedure of Example 13 (3) was repeated except that S-methyl-N-ethyl-N-(6-fluoro-3-pyridylmethyl)-N'-methylisothiourea was used in lieu of S-methyl-N-methyl-N'-ethyl-N'-(3-pyridylmethyl)isothiorea to give the title compound as oil.

NMR (CDCl₃) δ: 1.19 (3 H, t, CH₂C<u>H</u>₃), 3.08 (3 H, d, Me<u>NH</u>), 3.16 (2 H, q, C<u>H</u>₂CH₃), 4.37 (2 H, s, CH₂), 6.54 (1 H, s, =CHNO₂), 6.98 (1 H, dd, J=8.4 & 2.7 Hz), 7.80 (1 H, ddd, J=8.4, 2.4 & 8.4 Hz), 8.15 (1 H, d, J=2.4 Hz)

IR (neat): 3230, 1593, 1510, 1480, 1395, 1335, 1235, 1120, 1020 cm⁻¹

Example 82

1-[N-(6-Bromo-3-pyridylmethyl)-N-methyl]amino-1-methylamino-2-nitroethylene (Compound 100)

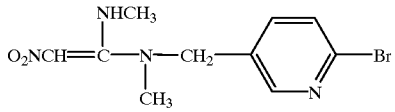

The steps (1), (2) and (3) of Example 13 were repeated except that crude N-(6-bromo-3-pyridylmethyl)-N-methylamine was used in lieu of N-ethyl-N-(3-pyridylmethyl)amine to give the following compounds in the respective steps.

(1) N-(6-Bromo-3-pyridylmethyl)-N-methyl-N'-methylthiourea (white crystals)
(provided that the product was purified by silica gel column chromatography)
m.p.: 107–108° C.

NMR (CDCl₃) δ: 3.04 (3 H, s), 3.18 (3 H, d, J=4.8 Hz), 5.19 (2 H, s), 5.6–6.1 (1 H, br), 7.46 (1 H, d, J=8.4 Hz), 7.66 (1 H, dd, J=8.4 & 2.4 Hz), 8.29 (1 H, d, J=2.4 Hz)

(2) S-Methyl-N-(6-bromo-3-pyridylmethyl)-N-methyl-N'-methylisothiourea (colorless oil)

NMR (CDCl₃) δ: 2.29 (3 H, s), 2.84 (3 H, s), 3.23 (3 H, s), 4.50 (2 H, s), 7.3–7.6 (2 H, m), 8.29 (1 H, d, J=2.4 Hz)

(3) Title compound (pale brown crystals)
m.p.: 130–131° C.

NMR (CDCl₃) δ: 2.80 (3 H, s), 3.06 (3 H, d, J=5.4 Hz), 4.36 (2 H, s), 6.51 (1 H, s), 7.35–7.70 (2 H, m), 8.2–8.4 (1 H, m), 9.4–10.0 (1 H, br)

IR (Nujol): 3200, 1580, 1390, 1280, 1245, 1205, 1075 cm⁻¹

Example 83

1-[N-(6-Bromo-3-pyridylmethyl)-N-ethyl]amino-1-methylamino-2-nitroethylene (Compound 101)

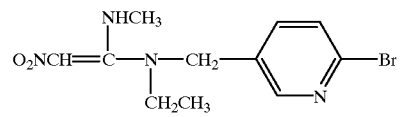

The steps (1), (2) and (3) of Example 13 were repeated except that crude N-(6-bromo-3-pyridylmethyl)-N-ethylamine was used in lieu of N-ethyl-N-(3-pyridylmethyl)amine to give the following compounds in the respective steps.

(1) N-(6-Bromo-3-pyridylmethly)-N-ethyl-N'-methylthiourea (pale yellow crystals)
m.p.: 130–131° C.

NMR (CDCl₃) δ: 1.18 (3 H, t, J=7.8 Hz), 3.18 (3 H, d, J=5.0 Hz), 3.46 (2 H, q, J=7.8 Hz), 5.12 (2 H, s), 5.5–6.0 (1 H, br), 7.46 (1 H, d, J=8.7 Hz), 7.69 (1 H, dd, J=8.7 & 2.1 Hz), 8.29 (1 H, d, J=2.1 Hz)

(2) S-Methyl-N-(6-bromo-3-pyridylmethyl)-N-ethyl-N'-methylisothiourea (yellow oil)

NMR (CDCl₃) δ: 1.08 (3 H, t, J=6.3 Hz), 2.29 (3 H, s), 3.21 (3 H, s), 3.36 (2 H, q, J=6.3 Hz), 4.46 (2 H, s), 7.3–7.6 (2 H, m), 8.28 (1 H, br s)

(3) Title compound
(provided that the reaction was conducted for 38 hours)
m.p.: 79–80° C.

NMR (CDCl₃) δ: 1.18 (3 H, t, J=6.3 Hz), 3.06 (3 H, d, J=5.7 Hz), 3.16 (2 H, q, J=6.3 Hz), 4.34 (2 H, s), 6.53 (1 H, s), 7.3–7.7 (2 H, m), 8.30 (1 H, br s), 9.5–10.1 (1 H, br q, J=5.7 Hz)

IR (Nujol): 3200, 1580, 1240, 1080 cm⁻¹

Example 84

1-[N-(2-Chloro-5-thiazolylmethyl)-N-methyl]amino-1-methylamino-2-nitroethylene (Compound 102)

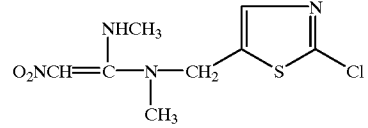

The steps (1), (2) and (3) of Example 13 were repeated except that crude N-(2-chloro-5-thiazolylmethyl)-N-methylamine was used in lieu of N-ethyl-N-(3-pyridylmethyl)amine to give the following compounds in the respective steps.

(1) N-(2-Chloro-5-thiazolylmethyl)-N-methyl-N'-methylthiourea (white—pale brown crystals)
(provided that a silica gel column was used for purification)
m.p.: 129–131° C.

NMR (CDCl₃) δ: 3.06 (s, <u>Me</u>NCH₂), 3,16 (d, J=4 Hz, <u>Me</u>NH), 5.21 (s, CH₂), 5.83 (br, NH), 7.48 (s, thiazole-H)

(2) S-Methyl-N-(2-chloro-5-thiazolylmethyl)-N-methyl-N'-methylisothiourea (yellow oil)

NMR (CDCl₃) δ: 2.30 (s, MeS), 2.90 (s, <u>Me</u>NCH₂), 3.24 (s, MeN=), 4.50 (s, CH₂), 7.39 (s, thiazole-H)

(3) Title compound (pale brown crystals)

m.p.: 131–133° C.

NMR (CDCl₃) δ: 2.84 (s, <u>Me</u>NCH₂), 3.09 (d, J=5 Hz, <u>Me</u>N=), 4.49 (s, CH₂), 6.51 (s, =CHNO₂), 7.50 (s, thiazole-H), 9.66 (br, NH)

IR (Nujol): 1585, 1395, 1260, 1070, 1050, 1025 cm⁻¹

Example 85

1-[N-(2-Chloro-5-thiazolylmethyl)-N-ethyl]amino-1-methylamino-2-nitroethylene (Compound 103)

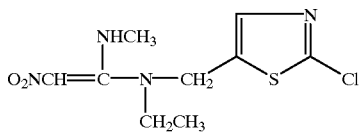

The steps (1), (2) and (3) of Example 13 were repeated except that crude N-(2-chloro-5-thiazolylmethyl)-N-ethylamine was used in lieu of N-ethyl-N-(3-pyridylmethyl) amine to give the following compounds in the respective steps.

(1) N-(2-Chloro-5-thiazolylmenthyl)-N-ethyl-N'-methylthiourea (white crystals)

m.p.: 116–118° C.

NMR (CDCl₃) δ: 1.19 (t, J=7 Hz, CH₂C<u>H</u>₃), 3.16 (d, J=4 Hz, <u>Me</u>NH), 3,44 (q, J=7 Hz, C<u>H</u>₂CH₃), 5.15 (s, thiazole-CH₂), 5.79 (br, NH), 7.47 (thiazole-H)

(2) S-Methyl-N-(2-chloro-5-thiazolylmethyl)-N-ethyl-N'-methylisothiourea (oil)

NMR (CDCl₃) δ: 1.11 (t, J=7 Hz, CH₂C<u>H</u>₃), 2.28 (s, MeS), 3.26 (s, MeN), 3.40 (q, J=7 Hz, C<u>H</u>₂CH₃), 4.50 (s, thiazole-CH₂), 7.39 (s, thiazole-H)

(3) Title compound (pale brown crystals)
(provided that the reaction was conducted for 24 hours).

m.p.: 91–92° C. (This product was recrystallized from AcOEt-hexane to give product indicating m.p. 110–112° C.)

NMR (CDCl₃) δ: 1.18 (t, J=7 Hz, CH₂C<u>H</u>₃), 3.07 (d, J=5 Hz, <u>Me</u>NH), 3.17 (q, J=7 Hz, C<u>H</u>₂CH₃), 4.46 (s, thiazole-CH₂), 6.52 (s, =CHNO₂), 7.47 (s, thiazole-H), 9.75 (br, NH)

IR (Nujol): 1585, 1450, 1405, 13600, 1255, 1225, 1050 cm⁻¹

Example 86

1-(2-Chloro-5-thiazolylmethyl)amino-1-dimethylamino-2-nitroethylene (Compound 104)
and 1,1-bis(2-chloro-5-thiazolylmethyl)amino-2-nitroethylene (Compound 105)

(Compound 104)

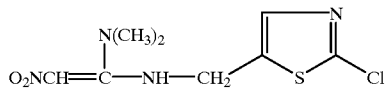

(Compound 105)

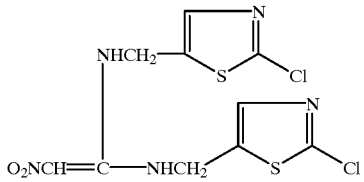

A mixture of 0.60 g (0.0037 mole) of 1-dimethylamino-1-methylthio-2-nitroethylene, 0.55 g of 2-chloro-5-thiazolymethylanine and 30 ml of EtOH was refluxed for 1.5 hours. After cooling, the resulting crystals of 1-N-(2-chloro-5-thiazolylmethyl)amino-1-methylthio-2-nitroethylene (0.20 g) were filtered off and the filtrate was concentrated and subjected to silica gel column chromatography using EtOH-CHCl₃ (1:10) as the eluent. The procedure gave 0.07 g of the title compound (Compound 104) and 0.034 g of the title compound (Compound 105). (1-(2-Chloro-5-thiazolylmethyl)amino-1-methylthio-2-nitroethylene)

m.p.: 150–152° C.

NMR (CDCl₃) δ: 2.49 (3 H, s), 4.78 (2 H, d, J=6.0 Hz), 6.58 (1 H, s), 7.52 (1 H, s), 10.3–10.8 (1 H, br)

(Compound 104)

m.p.: 101–102° C.

NMR (CDCl₃) δ: 2.97 (6 H, s), 4.58 (2 H, d, J=6.3 Hz), 6.51 (1 H, s), 7.50 (1 H, s), 9.3–9.8 (1 H, br)

IR (Nujol): 3100, 1585, 1380, 1255, 1030 cm⁻¹

(Compound 105)

m.p.: 211° C. (decompn.)

NMR (DMSO-d₆) δ: 4.5–4.8 (4 H, m), 6.63 (1 H, s), 7.63 (2 H, s)

IR (Nujol): 3120, 1610, 1210, 1040 cm⁻¹

Example 87

1-(2-Chloro-5-thiazolylmethyl)amino-1-methylamino-2-nitroethylene (Compound 106)

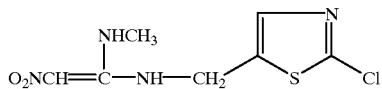

A mixture of 0.19 g (0.00072 mole) of the 1-N-(2-chloro-5-thiazolylmethyl)amino-1-methylthio-2-nitroethylene prepared in Example 86 and 25 ml of EtOH was heated at 70° C. Then 0.1 g of a 40% aqueous solution of methylamine was added and the mixture was stirred at 70° C. for 0.5 hour. The EtOH was distilled off, and after addition of AcOEt, the crystalline residue was filtered and dried. The procedure gave 0.12 g of the title compound as white crystals.

m.p.: 181° C. (decompn.)

NMR (DMSO-d₆) δ: 2.83 (3 H, d, J=5.1 Hz), 4.63 (2 H, d, J=6.3 Hz), 6.57 (1 H, s), 7.66 (1 H, s), 7.3–8.1 (1 H, br), 9.6–10.4 (1 H, br)

IR (Nujol): 3140, 1620, 1415, 1210 cm⁻¹

Example 88

1-(6-Chloro-3-pyridylmethyl)amino-1-dimethylamino-2-nitroethylene (Compound 46)

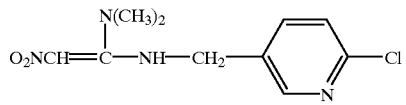

(1) A mixture of 4.32 g (0.0303 mole) of 6-chloro-3-pyridylmethylamine, 20 ml of water and 1.78 g of sodium hydroxide was stirred at room temperature and 2.37 ml of carbon disulfide was added dropwise. After completion of dropwise addition, the mixture was further stirred at 50° C. for 1 hour. After cooling with ice-water, 3.49 nil of ethyl chlorocarbonate was added dropwise at about 5° C. After completion of dropwise addition, the mixture was stirred at 50° C. for 1 hour. After cooling, the reaction mixture was saturated with sodium chloride and extracted with $Et_2O$ (50 ml×3), and the extract aas dried over $MgSO_4$. Then, the $Et_2O$ was distilled off to recover 5.38 g of crude (6-chloro-3-pyridyl)methyl isothiocyanate as oil.

NMR ($CDCl_3$) δ: 4.77 (s, $CH_2$), 7.39 (d, J=8 Hz, 1 H), 7.70 (dd, J=8 & 2 Hz, 1 H), 8.36 (d, J=2 Hz, 1 H)

(2) A mixture of 5.16 g or a 50% aqueous solution of dimethylamine and 30 ml of $CH_3CN$ was stirred under cooling with ice-water. Then, a solution of 5.29 g (0.0287 mole in terms of pure product) of crude (6-chloro-3-pyridyl) methyl isothiocyanate in 30 ml of $CH_3CN$ was added dropwise thereto. After completion of dropwise addition, the mixture was stirred at room temperature for 15 minutes. The $CH_3CN$ was distilled off and the residue was diluted with aqueous sodium chloride solution and extracted with $CH_2Cl_2$ (50 ml×3). The extract was dried over $MgSO_4$ and the $CH_2Cl_2$ was distilled off, whereupon crystals were obtained. After addition of $Et_2O$, the crystals were collected by filtration, dried and recrystallized from AcOEt. The procedure gave 3.82 g of N-(6-chloro-3-pyridylmethyl)-N'-dimethylthiourea as yellow crystals.

m.p.: 139–141° C.

NMR ($CDCl_3$) δ: 3.27 (s, $Me_2N$), 4.88 (d, J=5 Hz, $CH_2$), 6.17 (br t, J=5 Hz, NH), 7.27 (d, J=8 Hz, 1 H), 7.76 (dd, J=8 & 2 Hz, 1 H), 8.25 (d, J=2 Hz, 1 H)

(3) To 3.00 g (0.013 mole) of N-(6-chloro-3-pyridylmethyl)-N'-dimethylthiourea was added 32 ml of dry THF, followed by addition of 0.52 g of 60% sodium hydride. The mixture was stirred at 50° C. for 15 minutes. After cooling pith ice-water, 0.814 ml of methyl iodide was added dropwise and the mixture was stirred at room temperature for 20 minutes. The THF was distilled off and the residue was diluted with aqueous sodium chloride solution and extracted with AcOEt (50 ml×3). The extract was dried over $MgSO_4$ and the AcOEt was distilled off. The procedure gave 3.30 g of crude S-methyl-N-(6-chloro-3-pyridylmethyl)-N'-dimethylisothiourea as oil.

NMR ($CDCl_3$) δ: 2.30 (s, MeS), 2.98 (s, $Me_2N$), 4.69 (s, $CH_2$) 7.25 (d, J=8 Hz, 1 H), 7.65 (dd, J=8 & 2 Hz, 1 H), 8.37 (d, J=2 Hz, 1 H)

(4) To 3.24 g (0.0133 mole in terms of pure products) of crude S-methyl-N-(6-chloro-3-pyridylmethyl)-N'-dimethylisothiourea was added 14.5 ml of $CH_3NO_2$ and the mixture was refluxed with stirring for 14.5 hours. The $CH_3NO_2$ was then distilled off and the residue was subjected to silica gel (240 g) column chromatography using MeOH-$CHCl_3$ (1:5) as the eluent to recover an oil. This oil was dissolved in AcOEt, the AcOEt was distilled off, and the residue was allowed to stand, whereupon crystals separated out. After addition of $Et_2O$, the crystals were recovered by filtration, washed with $Et_2O$ and dried. The procedure gave 2.30 g of the title compound as pale yellow crystals. This product was in agreement with Compound 46 obtained in Example 28 in melting point, NMR and IR spectra and TLC Rf.

Example 89

1-(6-Chloro-3-pyridyl)amino-1-dimethylamino-2-nitroethylene (Compound 107)

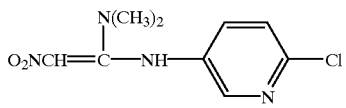

A mixture of 1.5 g (0.0093 mole) of 1-dimethylamino-1-methylthio-2-nitroethylene and 1.1 g of 5-amino-2-chloropyridine was heated at 110–120° C. with stirring for 1 hour. After cooling, the reaction mixture was subjected to silica gel column chromatography using EtOH-$CHCl_3$ (1:40) as the eluent to recover 0.38 g of the title compound as pale brown crystals. The NMR spectrum of this product showed that it was a 1:1 mixture of the title compound and $N^2$-(6-chloro-3-pyridyl)-N'-dimethyl-2-nitroacetamidine.

m.p.: 122–123° C.

NMR ($CDCl_3$) δ: 2.86 (3 H, s), 3.10 (3 H, s), 5.17 (1 H, s), 6.68 (0.5 H, S), 7.09 (0.5 H, dd, J=9.0 & 2.7 Hz), 7.24 (0.5 H, d, J=9.0 Hz), 7.3–7.6 (1 H, m), 7.86 (0.5 H, d, J=2.7 Hz), 8.22 (0.5 H, d, J=2.7 Hz), 10.8–11.2 (0.5 H, br)

IR (Nujol): 3100, 1395, 1280 $cm^{-1}$

Example 90

1-[N-(6-Methoxy-3-pyridyl)-N-methyl]amino-1-methylamino-2-nitroethylene (Compound 108)

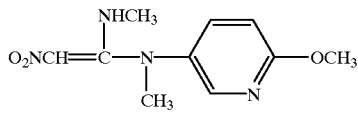

The steps (1), (2) and (3) of Example 59 were repeated except that 2-methoxy-5-methylaminopyridine was used in lieu of 2-chloro-5-methylaminopyridine to give the following compounds in the respective steps.

(1) N-(6-Methoxy-3-pyridyl)-N-methyl-N'-methylthiourea (white crystals)
(provided that the reaction was conducted in toluene)
m.p.: 115.5–116° C.

NMR ($CDCl_3$) δ: 3.06 (3 H, d, J=4.5 Hz), 3.65 (3 H, s), 3.97 (3 H, s), 5.2–5.8 (1 H, m, NH), 6.86 (1 H, d, J=8.7 Hz), 7.46 (1 H, dd, J=9.0 & 3.0 Hz), 8.08 (1 H, d, J=2.4 Hz)

(2) S-Methyl-N-(6-methoxy-3-pyridyl)-N-methyl-N'-methylisothiourea (pale yellow oil)

NMR ($CDCl_3$) δ: 2.01 (3 H, s), 3.18 (3 H, s), 3.28 (3 H, s), 3.93 (3 H, s,), 6.72 (1 H, d, J=9.0 Hz), 7.43 (1 H, dd, J=9.0 & 3.0 Hz), 8.02 (1 H, d, J=2.4 Hz)

(3) Title compound (yellow crystals)
(provided that the reaction was conducted for 16 hours)

m.p.: 131–132° C.

NMR (CDCl$_3$) δ: 2.65 (3 H, d, J=5.4 Hz), 3.27 (3 H, s), 3.96 (3 H, s), 6.07 (1H, s), 6.82 (1 H, d, J=9.0 Hz), 7.43 (1 H, dd, J=8.4 & 3.0 Hz), 8.04 (1 H, d, J=2.7 Hz), 9.8–10.4 (1 H, m)

IR (Nujol): 3130, 1590 cm$^{-1}$

Example 91

1-[N-(6-Chloro-3-pyridyl)-N-methyl]amino-1-methylamino-2-ethoxycarbonyl-2-nitroethylene (Compound 109)

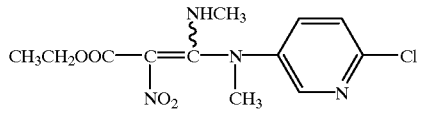

A mixture of 2.0 g (0.0087 mole) of S-methyl-N-(6-chloro-3-pyridyl)-N-methyl-N'-methylisothiourea and 4.0 g of ethyl nitroacetate was stirred with heating at 90–100° C. for 6 hours. After cooling, a small amount of acetone was added and the resulting crystals were collected by filtration, washed with acetone and dried. The procedure gave 0.3 g of the title compound as white crystals. From the filtrate, acetone was distilled off and the residue was further stirred with heating at 90–100° C. for 16 hours. The procedure gave a furhter crop (0.2 g) of the title compound.

m.p.: 225–227° C. (decompn.)

NMR (DMSO-d$_6$) δ: 1.10 (3 H, t, J=6.9 Hz), 2.89 (3 H, s), 3.45 (3 H, s), 3.93 (2 H, q, J=7.3 Hz), 7.60 (1 H, d, J=8.4 Hz), 7.75 (1 H, dd, J=8.1 & 2.7 Hz), 8.30 (1 H, d, J=2.1 Hz), 9.31 (1 H, br s)

IR (Nujol): 3190, 1675, 1630 cm$^{-1}$

Example 92

1-[N-(6-Chloro-3-pyridylmethyl)-N-methyl]amino-1-(N-formyl-N-methyl)amino-2-nitroethylene (Comnound 110)

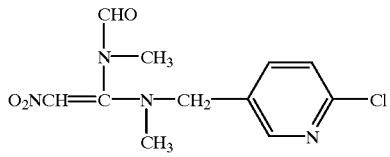

The reaction procedure of Example 46 was repeated except that 1-[N-(6-chloro-3-pyridylmethyl)-N-methyl]amino-1-methylamino-2-nitroethylene was used in lieu of 1-methylamino-1-[N-methyl-N-(3-pyridylmethyl)]amino-2-nitroethylene to give the title compound as a yellow resinous mass.

NMR (DMSO-d$_6$) δ: 2.92 (s, 3 H), 3.03 (s, 3 H), 4.60 (br, 2 H), 6.86 (s, 1 H), 7.48 (d, J=8 Hz, 1 H), 7.80 (dd, J=8 & 2 Hz, 1 H), 8.23 (s, 1 H), 8.38 (d, J=2 Hz, 1 H)

IR (neat): 1690, 1560, 1490, 1350, 1270, 1100 cm$^{-1}$

Example 93

1-[N-(6-Chloro-3-pyridylmethyl)-N-ethyl]amino-1-(N-formyl-N-methyl)amino-2-nitroethylene (Compound 111)

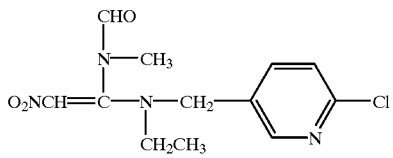

The reaction procedure of Example 46 was repeated except that 1-[N-(6-chloro-3-pyridylmethyl)-N-ethyl]amino-1-methylamino-2-nitroethylene was used in lieu of 1-methylamino-1-[N-methyl-N-(3-pyridylmethyl)]amino-2-nitroethylene to give the title compound as a yellow resinous mass.

NMR (DMSO-d$_6$) δ: 1.13 (t, J=7 Hz, 3 H), 3.00 (s, 3 H), 3.10–3.53 (m, 2 H), 4.60 (br, 2 H), 6.96 (s, 1 H), 7.48 (d, J=8 Hz, 1 H), 7.82 (dd, J=8 & 2 Hz, 1 H), 8.20 (s, 1 H), 8.39 (d, J=2 Hz, 1 H)

IR (neat): 1685, 1560, 1480, 1340, 1240, 1100 cm$^{-1}$

Example 94

1-[N-(6-Chloro-3-pyridyl)-N-methyl]amino-1-(N-formyl-N-methyl)amino-2-nitroethylene (Compound 112)

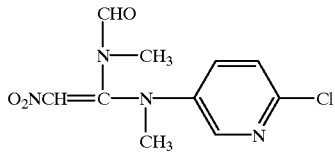

The reaction procedure of Example 46 was repeated except that 1-[N-(6-chloro-3-pyridyl)-N-methyl]amino-1-methylamino-2-nitroethylene was used in lieu of 1-methylamino-1-[N-methyl-N-(3-pyridylmethyl))]amino-2-nitroethylene to give the title compound as yellow crystals.

m.p.: 134–135° C.

NMR (DMSO-d$_6$) δ: 2.73 & 2.89 (each s, 3 H), 3.32 & 3.39 (each s, 3 H), 7.03 & 7.10 (each s, 1 H), 7.46 & 7.57 (each d, J=8 Hz, 1 H), 7.83 & 7.92 (each dd, J=8 & 2 Hz, 1 H), 8.35 & 8.70 (each s, 1 H), 8.37 & 8.44 (each d, J=2 Hz, 1 H)

IR (Nujol): 1685, 1560, 1305, 1280, 1250, 1135 cm$^{-1}$

Example 95

1-[N'-(6-Chloro-3-pyridylmethyl)-N-formyl]amino-1-dimethylamino-2-nitroethylene (Compound 113)

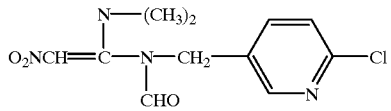

The reaction procedure of Example 46 was repeated except that 1-N-(6-chloro-3-pyridylmethyl)amino-1-dimethylamino-2-nitroethylene was used in lieu of 1-methylamino-1-[N-methyl-N-(3-pyridylmethyl)]amino-2-nitroethylene to give the title compound as pale yellow crystals.

m.p.: 105–106° C.

NMR (DMSO-d$_6$) δ: 2.93 (s, 6 H), 4.33–5.10 (m, 2 H), 6.72 (s, 1 H), 7.42 (d, J=8 Hz, 1 H), 7.80 (dd, J=8 & 2 Hz, 1 H), 8.23 (s, 1 H), 3.36 (d, J=2 Hz, 1 H)

IR (Nujol); 1700, 1565, 1490, 1350, 1270, 1205, 1100 cm$^{-1}$

Example 96

A 7:3 mixture of 1-(6-chloro-3-pyridylmethyl)amino-1-(N-formyl-N-methyl)amino-2-nitroethylene (Compound 114) and 1-[N-(6-chloro-3-pyridylmethyl)-N-formyl]amino-1-methylamino-2-nitroethylene (Compound 115)

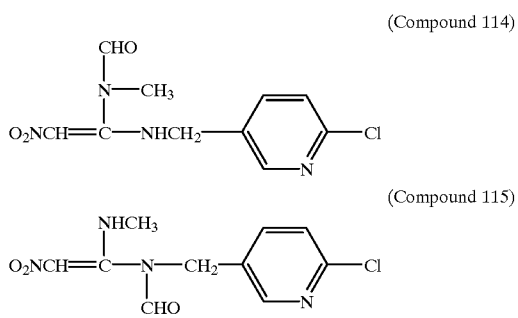

In 10 ml of DMF was suspended 0.1 g of 60% sodium hydride, previously washed with petroleum ether, and a solution of 0.6 g (0.0025 mole) of 1-N-(6-chloro-3-pyridylmethyl)amino-1-methylamino-2-nitroethylene in 3 ml of DMF was added dropwise. The mixture was stirred at room temperature for 1 hour. After cooling, 0.7 g of formic acetic anhydride was added and the mixture was stirred under ice-cooling for 5 hours and, then, at room temperature for 20 hours. The DMF was distilled off under reduced pressure and the residue was diluted with 20 ml of saturated aqueous sodium hydrogen carbonate solution and extracted with CH$_2$Cl$_2$ (20 ml×3). The extract was dried over MgSO$_4$ and the CH$_2$Cl$_2$ was distilled off. Finally, the residue was subjected to silica gel column chromatography using EtOH-CHCl$_3$ (1:10) as the eluent. The procedure gave 0.15 g of a 7:3 mixture of the title compounds (Compound 114 and Compound 115) as white crystals.

m.p.: 80–85° C.

NMR (DMSO-d$_6$) δ: (Compound 114) 3.05 (s, 3 H), 4.53 (d, J=6 Hz, 2 H), 6.76 (s, 1 H), 7.49 (d, J=8 H, 1 H), 7.86 (dd, J=8 & 2 Hz, 1 H), 8.30 (s, 1 H), 8.42 (d, J=2 Hz, 1 H), 9.45 (br, 1 H) (Compound 115) 2.95 (d, J=5 Hz, 3 H), 4.83 (s, 2 H), 6.66 (s, 1 H), 7.46 (d, J=8 Hz, 1 H), 7.86 (dd, J=8 & 2 Hz, 1 H), 8.30 (s, 1 H), 8.42 (d, J=2 Hz, 1 H), 9.45 (br, 1 H)

IR (Nujol): 3200, 3100, 1685, 1600, 1340, 1250, 1080, 1040 cm$^{-1}$

Example 97

1-(6-Chloro-3-pyridylmethyl)amino-1-methylamino-2-ethoxycarbonyl-2-nitroethylene (Compound 116)

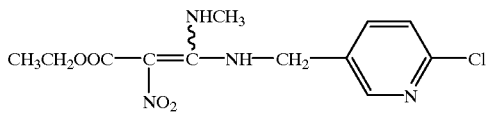

A mixture of 1.4 g (0.0061 mole) of S-methyl-N-(6-chloro-3-pyridylmethyl)-N'-methylisothiourea obtained in Example 64 (2) and 2.7 g of ethyl nitroacetate was stirred with heating at 75–80° C. for 3 hours. After cooling, the crystals were collected by filtration, washed with CH$_3$CN and dried. The procedure gave 1.1 g of the title compound as white crystals.

m.p.: 231–233° C. (decompn.)

NMR (DMSO-d$_6$) δ: 1.07 (3 H, t, J=7 Hz), 2.86 (3 H, br s), 3.94 (2 H, q, J=7 Hz), 4.47 (2 H, br s), 7.51 (1 H, d, J=8 Hz), 7.82 (1 H, dd, J=8 & 2.7 Hz), 8.38 (1 H, d, J=2.7 Hz), 9.10–9.60 (2 H, br s)

IR (Nujol): 3250, 1660, 1500, 1320, 1230 cm$^{-1}$

Example 98

1-(6-Chloro-3-pyridylmethyl)amino-1-methylamino-2-methanesulfonylthiocarbamoyl-2-nitroethylene (Compound 117)

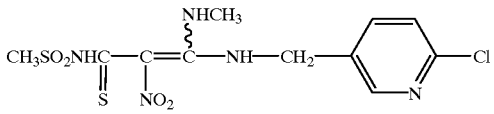

In 50 ml of CH$_3$CN was dissolved 0.50 g (0.002 mole) of 1-(6-chloro-3-pyridylmethyl)amino-1-methylamino-2-nitroethylene, followed by addition of 0.30 g (0.002 mole) of methanesulfonyl isothiocyanate. The mixture was stirred at room temperature for 2 hours. The CH$_3$CN was distilled off and the residue was purified by silica gel column chromatography. The procedure gave 0.25 g of the title compound as yellow crystals.

m.p.: 129–131° C.

NMR (DMSO-d$_6$) δ: 2.76–3.00 (each d, MeN), 3.51 & 3.55 (each s, MeSO$_2$), 4.36–4.70 (each d), 12.20–13.23 (each s)

IR (Nujol): 3200, 1640, 1340, 1140, 920 cm$^{-1}$

Example 99

1-N-(6-Bromo-3-pyridylmethyl)amino-1-methylamino-2-nitroetylene (Compound 118)

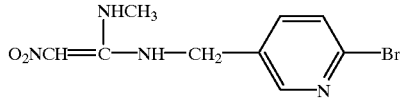

The steps (1), (2) and (3) of Example 13 were repeated except that 6-bromo-3-pyridylmethylamine was used in lieu of N-ethyl-N-(3-pyridylmethyl)amine, to give the following compounds in the respective steps.

(1) N-(6-Bromo-3-pyridylmethyl)-N'-methylthiourea (white crystals)

(provided that Et$_2$O-THF (3:1) was used as the reaction solvent)

m.p.: 117–118° C.

NMR(DMSO-d$_6$)δ: 2.85 (d,J=5Hz,MeN), 4.67 (d,J=6Hz, CH$_2$N), 7.54 (d,J=8Hz, 1H), 7.6 (br, MeNH), 7.69 (dd, J=8 & 2 Hz, 1H), 7.93 (t, J=6Hz,CH$_2$NH), 8.32 (d,J=2Hz, 1H)

(2) S-Methyl-N-(6-Bromo-3-pyridylmethyl)-N'-methylisothiourea (yellow oil)

NMR(CDCl$_3$)δ: 2.40 (s,MeS), 2.93 (s,MeN=), 4.34(br, NH), 4.47 (S,CH$_2$N), 7.42 (d,J=8Hz,1H), 7.61 (dd,J=8 & 2Hz,1H), 8.36 (d,J=2Hz,1H)

(3) Title compound (pale brown crystals)

m.p.: 184–186° C. (decompn.)

NMR(DMSO-d$_6$)δ: 2.37 (br. MeN), 4.47 (d,J=6Hz, CH$_2$N), 6.46 (s,=CHNO$_2$), 7.61 (d,J=8Hz,1H), 7.72 (dd,J=8 & 2Hz,1H), 8.40 (d,J=2Hz,1H)

IR (Nujol): 1615, 1575, 1455, 1370, 1230, 1200 cm$^{-1}$

Example 100

1-N-(6-Bromo-3-pyridylmethyl)amino-1-(N-formyl-N-methyl)amino-2-nitroethylene (Compound 119) and 1-[N-(6-bromo-3-pyridylmethyl)-N-formyl]amino-1-methylamino-2-nitroethylene (Compound 120)

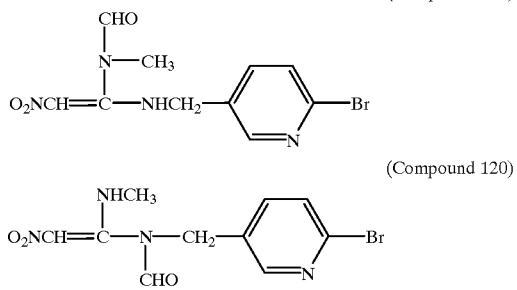

The reaction procedure of Example 96 was repeated except that 1-N-(6-bromo-3-pyridylmethyl)amino-1-methylamino-2-nitroethylene was used in lieu of 1-N-(6-chloro-3-pyridylmethyl)amino-1-methylamino-2-nitroethylene. To the oil obtained through the purification of silica gel column chromatography, was added a small amount of AcOEt and Et$_2$O, followed by cooling with dry ice-acetone bath to give a mixture (90:10) of the title compounds (Compound 119 and Compound 120) as pale brown powder. And, the filtrate was concentrated to give a mixture (40:60) of the title compounds (Compound 119 and Compound 120) as viscous product.

(the 90:10 mixture of Compounds 119 and 120)

m.p.: 115–127° C.

NMR(CDCl$_3$)δ: (Compound 119) 3.13 (s,MeN), 4.48 (d,J=6Hz,CH$_2$N), 6.57 (s,=CHNO$_2$), 7.53 (m,2H,pyridine-H$_2$), 8.33 (S,2H,CHO and pyridine-H), 9.46 (br,NH)

IR (Nujol): 1690, 1620, 1250, 1240, 1080 cm$^{-1}$ $^{(the}$ 40:60 mixture of Compounds 119 and 120)

NMR(CDCl$_3$)δ: (Compound 120) 3.01 (d,J=5Hz,MeN), 4.73 (s,CH$_2$N), 6.36 (s,=CHNO$_2$), 7.53 (br s,2H,pyridine-H$_2$), 8.34 (br s,2H,CHO and pyridine-H$_1$), 9.35 (br,NH)

IR (neat): 1680, 1605, 1450, 1350, 1250, 1080 cm$^{-1}$

Example 101

1-[N-(2-Chloro-5-thiazolylmethyl)-N-methyl)amino-1-(N-formyl-N-methyl)amino-2-nitroethylene (Compound 121)

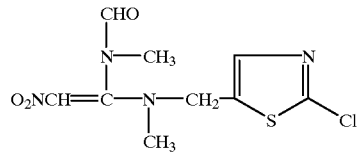

The reaction procedure of Example 46 was repeated except that 1-[N-(2-chloro-5-thiazolylmethyl)-N-methyl]amino-1-methylamino-2-nitroethylene was used in lieu of 1-methylamino-1-[N-methyl-N-(3-pyridylmethyl)amino-2-nitroethylene, to give the title compound as pale yellow resinous product.

NMR(DMSO-d$_6$)δ: 2.92 (s,3H,MeNCH$_2$), 2.99 (s,3H, MeNCHO), 4.74 (br s,2H,CH$_2$), 6.90 (s,1H,=CHNO$_2$), 7.71 (s,1H, thiazole-H), 8.19 (s,1H,CHO)

IR (neat): 1695, 1565, 1490, 1340, 1270, 1042 cm$^{-1}$

Example 102

1-[N-(2-Chloro-5-thiazolylmethyl)-N-ethyl)amino-1-(N-formyl-N-methyl)amino-2-nitroethylene (Compound 122)

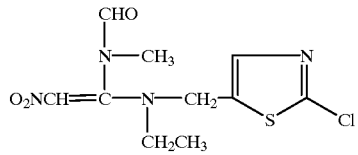

The reaction procedure of Example 46 was repeated except that 1-[N-(2-chloro-5-thiazolylmethyl)-N-ethyl]amino-1-methylamino-2-nitroethylene was used in lieu of 1-methylamino-1-[N-methyl-N-(3-pyridylmethyl)]amino-2-nitroethylene, to give the title compound as yellow crystals.

m.p.: 99–100° C.

NMR(DMSO-d$_6$)δ: 1.15 (t,3H,CH$_2$CH$_3$), 2.98 (s,3H, MeN), 3.32 (q,2H,CH$_2$CH$_3$), 4.76 (br s,2H,thiazole-CH$_2$), 7.02 (s,1H, =CHNO$_2$), 7.72 (s,1H,thiazole-H), 8.17 (s,1H, CHO)

IR (Nujol): 1698, 1577, 1557, 1470, 1448, 1352, 1315, 1270, 1053 cm$^{-1}$

Example 103

1-N-(2-Chloro-5-thiazolylmethyl)amino-1-[N-formyl-N-methyl)amino-2-nitroethylene (Compound 123) and 1-[N-(2-chloro-5-thiazolylmethyl)-N-formyl]amino-1-methylamino-2-nitroethylene (Compound 124)

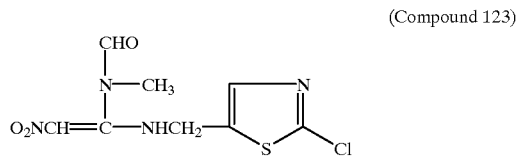

-continued (Compound 124)

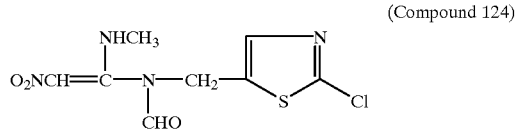

The reaction procedure of Example 100 was repeated except that 1-N-(2-chloro-5-thiazolylmethyl)amino-1-methylamino-2-nitroethylene was used in lieu of 1-N-(6-bromo-3-pyridylmethyl)amino-1-methylamino-2-nitroethylene, to give the title compound (Compound 124) as crystals and a mixture (70:30) of the title compounds (Compound 123 and Compound 124) as viscous product.

(Compound 124)

m.p.: 125–126° C.

NMR(CDCl$_3$)δ: 3.01 (3H,d,J=6.0 Hz), 4.82 (2H,s), 6.38 (1H,s), 7.49 (1H,s), 8.30 (1H,s), 9.0–9.6 (1H,br)

IR (Nujol): 3220, 1675, 1620, 1245, 1100, 1050 cm$^{-1}$ (the 70:30 mixture of Compounds 123 and 124)

NMR(CDCl$_3$)δ: (Compound 123) 3.16 (3H,s), 4.63 (2H, d,J=5.7 Hz), 6.57 (1H,s), 7.49 (1H,s), 8.35 (1H,s), 9.1–9.6 (1H,br)

IR (neat): 3220, 1680, 1605, 1480, 1250, 1045 cm$^{-1}$

Example 104

1-[N-(6-Bromo-3-pyridylmethyl)-N-methyl]amino-1-(N-formyl-N-methyl)amino-2-nitroethylene (Compound 125)

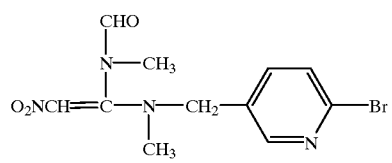

The reaction procedure of Example 46 was repeated except that 1-[N-(6-bromo-3-pyridylmethyl)-N-methyl] amino-1-metylamino-2-nitroethylene was used in lieu of 1-methylamino-1-[N-methyl-N-(3-pyridylmethyl)]amino-2-nitroethylene, to give the title compound as yellow resinous product.

(provided that THF-DMF was used as the reaction solvent)

NMR(DMSO-d$_6$)δ: 2.93 (s,3H), 3.02 (s,3H), 4.3–4.9 (m,2H), 6.87 (s,=CHNO$_2$), 7.68 (br s,2H), 8.23 (s,CHO), 8.3–8.5 (m,1H)

IR (neat): 1685 cm$^{-1}$

Example 105

1-[N-(6-Bromo-3-pyridylmethyl)-N-ethyl]amino-1-(N-formyl-N-methyl)amino-2-nitroethylene (Compound 126)

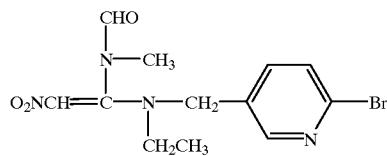

The reaction procedure of Example 46 was repeated except that 1-[N-(6-bromo-3-pyridylmethyl)-N-ethyl] amino-1-methylamino-2-nitroethylene was used in lieu of 1-methylamino-1-[N-methyl-N-(3-pyridylmethyl)]amino-2-nitroethylene, to give the title compound as yellow crystals.

m.p.: 105–108° C.

NMR(DMSO-d$_6$)δ: 1.13 (t,J=7.2 Hz,3H), 3.00 (s,3H), 3.1–3.7 (m,2H), 4.3–4.9 (m,2H), 6.97 (s,=CHNO$_2$), 7.5–7.9 (m,2H), 8.21 (s,CHO), 8.38 (br s,1H)

IR (Nujol): 1705 cm$^{-1}$

Example 106

1-N-(6-Bromo-3-pyridylmethyl)amino-1-dimethylamino-2-nitroethylene (Compound 127)

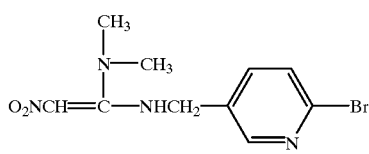

The steps (1), (2), (3) and (4) of Example 88 were repeated except that 6-bromo-3-pyridylmethylamine was used in lieu of 6-chloro-3-pyridylmethylamine, to give the following compounds in the respective steps.

(1) (6-Bromo-3-pyridyl)methyl isothiocyanate (yellow oil)

(provided that after completion of dropwise addition of ethyl chlorocarbonate, the mixture was stirred at 50° C. for 4 hours)

NMR(CDCl$_3$)δ: 4.73 (s,2H), 7.43–7.70 (m,2H), 8.35 (br s,1H)

(2) N-(6-Bromo-3-pyridylmethyl)-N'-dimethylthiourea (white crystals)

(provided that the product was purified by silica gel column chromatography using E$_t$OH-CHCl$_3$ (1:10) as the eluent)

m.p.: 124–125° C.

NMR(CDCl$_3$)δ: 3.27 (s,6H), 4.85 (d,J=5 Hz,2H), 6.32 (br t,J=5Hz,1H), 7.40 (d,J=8Hz,1H), 7.66 (dd,J=8 & 2 Hz,1H), 8.21 (d,J=2Hz,1H)

(3) S-Methyl-N-(6-bromo-3-pyridylmethyl)-N'-dimethylisothiourea (yellow oil)

NMR(CDCl$_3$)δ: 2.30 (s,3H), 3.00 (s,6H), 4.66 (s,2H), 7.38 (d,J=8Hz,1H), 7.55 (dd,J=8 & 2 Hz,1H), 8.35 (d,J=2 Hz,1H)

(4) Title compound (pale yellow crystals)

(provided that the reaction was conducted for 20 hours, and the product was purified by silica gel column chromatography and recrystallized from CH$_3$CN.

m.p.: 158–159° C.

NMR(CDCl$_3$)δ: 2.92 (s,6H), 4.45 (d,J=6 Hz,2H), 6.50 (s,1H), 7.48 (d,J=8 Hz,1H), 7.60 (dd,J=8 & 2 Hz,1H), 8.33 (d,J=2 Hz,1H), 9.70 (br,1H)

IR (Nujol): 3100, 1580, 1550, 1440, 1300, 1260, 1040 cm$^{-1}$

Example 107

1-[N-(6-Bromo-3-pyridylmethyl)-N-formyl]amino-
1-dimethylamino-2-nitroethylene (Compound 128)

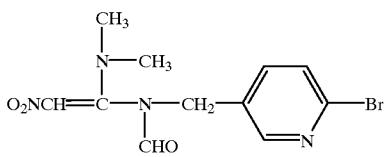

The reaction procedure of Example 46 was repeated except that 1-N-(6-bromo-3-pyridylmethyl)amino-1-dimethylamino-2-nitroethylene was used in lieu of 1-methylamino-1-[N-methyl-N-(3-pyridylmethyl)]amino-2-nitroethylene, to give the title compound as pale yellow crystals.
(provided that the reaction was conducted in DMF)
m.p.: 96–97° C.
NMR(DMSO-d$_6$)δ: 2.92 (s,6H), 4.30–5.06 (m,2H), 6.73 (s,1H), 7.50–7.80 (m,2H) 8.23 (s,1H), 8.35 (br s,1H)
IR (Nujol): 1700, 1565, 1490, 1345, 1270, 1080 cm$^{-1}$

Example 108

1-Amino-1-[N-(6-bromo-3-pyridylmethyl)-N-methyl]amino-2-nitroethylene (Compound 129)

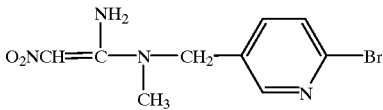

The steps (1) and (2) of Example 40 were repeated except that N-(6-bromo-3-pyridylmethyl)-N-methylamine was used in lieu of N-(6-chloro-3-pyridylmethyl)-N-ethylamine, to give the following compounds in the respective steps.

(1) 1-[N-(6-Bromo-3-pyridylmethyl)-N-methyl]amino-1-methylthio-2-nitroethylene (yellow oil)
(provided that the reaction was conducted for 3.5 hours)
NMR(CDCl$_3$)δ: 2.47 (s,3H), 3.03 (s,3H), 4.73 (s,2H), 6.76 (s,1H), 7.36–7.60 (m,2H), 8.30 (br s,1H)

(2) Title compound (white crystals)
(provided that the reaction was conducted in MeOH for 1 hour, and the precipitated crystals were collected by filtration)
m.p.: 206–207° C.
NMR(DMSO-d$_6$)δ: 3.03 (s,3H), 4.63 (s,2H), 6.60 (s,1H), 7.43–7.80 (m,2H), 8.30 (br s,1H), 8.88 (br,2H)
IR (Nujol): 3260, 3140, 1620, 1575, 1420, 1290, 1220 cm$^{-1}$

Example 109

1-N-(2-Chloro-5-thiazolylmethyl)amino-1-dimethylamino-2-nitroethylene (Compound 104)

The steps (1), (2), (3) and (4) of Example 88 were repeated except that 2-chloro-5-thiazolylmethylamine was used in lieu of 6-chloro-3-pyridylmethylamine, to give the following compounds in the respective steps.

(1) (2-Chloro-5-thiazolyl)methyl isothiocyanate
(provided that after completion of dropwise addition of ethyl chlorocarbonate, the mixture was stirred at 80° C. for 3 hours)
NMR(CDCl$_3$)δ: 4.82 (2H,s), 7.50 (1H,s)

(2) N-(2-Chloro-5-thiazolylmethyl)-N'-dimethylthiourea (yellow crystals)
m.p.: 125–127° C.
NMR(CDCl$_3$)δ: 3.28 (6H,s), 4.98 (2H,d,J=6.0 Hz), 5.6–6.1 (1H,br), 7.40 (1H,s)

(3) S-Methyl-N-(2-chloro-5-thiazolylmethyl)-N-dimethylisothiourea (yellow oil)
NMR(CDCl$_3$)δ: 2.31 (3H,s), 2.99 (6H,s), 4.79 (2H,s), 7.36 (1H,s)

(4) Title compound (pale grey crystals)
(provided that the reaction was conducted for 37° C.)
This product was in agreement with Compound 104 obtained in Example 86 in melting point, NMR and IR spectra and TLC Rf.

Example 110

1-[N-(2-Chloro-5-thiazolylmethyl)-N-formyl]amino-1-dimethylamino-2-nitroethylene (Compound 130)

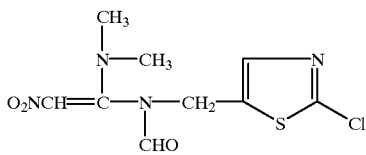

The reaction procedure of Example 46 was repeated except that 1-N-(2-chloro-5-thiazolylmethyl)amino-1-dimethylamino-2-nitroethylene was used in lieu of 1-methylamino-1-[N-methyl-N-(3-pyridylmethyl)]amino-2-nitroethylene, to give the title compound as white crystals. The NMR value of this product indicated this product was a mixture (6:1) of isomers.
m.p.: 139–142° C.
NMR(CDCl$_3$)δ: 2.92 & 2.99 (total 6H, each s), 4.83 (2H,s), 6.61 & 6.34 (total 1H,s), 7.45 (1H,s), 8.19 & 8.46 (total 1H, each s)
IR (Nujol): 1680, 1410, 1355, 1270, 1050 cm$^{-1}$

Example 111

1-[N-(6-Chloro-3-pyridylmethyl)-N-(2,2,2-trifluoroethyl)]amino-1-methylamino-2-nitroethylene (Compound 131)

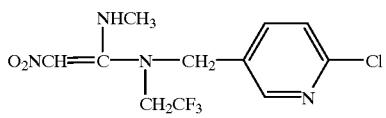

In 35 ml of toluene, 3.79 g (0.0169 mole) of N-(6-chloro-3-pyridylmethyl)-N-(2,2,2-trifluoroethyl)amine and 2.46 g of methyl isothiocyanate were stirred for 18 hours under reflux. The toluene was distilled off, and the residue was dissolved in 120 ml of AcOEt, washed with 1N HCl (two times) and aqueous sodium chloride solution in this order and dried over MgSO$_4$. The AcOEt was distilled off to give oil. To this oily product were added Et$_2$O and hexane, followed by cooling to give crystals. After addition of hexane to the mixture, the crystals were collected by filtration and dried to give 2.78 g of N-(6-chloro-3-pyridylmethyl)-N-(2,2,2-trifluoroethyl)-N'-methylthiourea as white crystals.

m.p.: 98–100° C.

NMR(CDCl$_3$)δ: 3.13 (d,J=5 Hz,MeN), 4.37 (q,J=9 Hz,CF$_3$CH$_2$), 5.09 (s,pyridine-CH$_2$), 6.07 (br,NH), 7.34 (d,J=8 Hz,1H), 7.67 (dd,J=8 & 2 Hz,1H), 8.26 (d,J=2 Hz,1H)

The steps (2) and (3) of Example 13 were repeated except that N-(6-chloro-3-pyridylmethyl)-N-(2,2,2-trifluoroethyl)-N'-methylthiourea was used in lieu of N-methyl-N'-ethyl-N'-(3-pyridylmethyl)thiourea, to give the following compounds in the respective steps.

(2) S-Methyl-N-(6-chloro-3-pyridylmethyl)-N-(2,2,2-trifluoroethyl)-N'-methylisothiourea (pale brown oil)

NMR(CDCl$_3$)δ: 2.28 (s,MeS), 3.24 (s,MeN), 4.07 (q,J=9 Hz,CF$_3$CH$_2$), 4.66 (s,pyridine-CH$_2$), 7.28 (d,J=8 Hz,1H), 7.54 (dd,J=8 & 2 Hz,1H), 8.26 (d,J=2 Hz,1H)

(3) Title compound
(provided that the reaction was conducted for 96 hours)
m.p.: 110–111° C.

NMR(CDCl$_3$)δ: 3.12 (d,J=5 Hz,MeN), 3.60 (q,J=9 Hz,CF$_3$CH$_2$), 4.42 (s,pyridine-CH$_2$), 6.51 (s,=CHNO$_2$), 7.39 (d,J=8 Hz,1H), 7.60 (dd,J=8 & 2 Hz,1H), 8.33 (d,J=2 Hz,1H), 9.50 (br,NH)

IR (Nujol): 1595, 1450, 1345, 1260, 1235, 1140, 1100 cm$^{-1}$

As the object compound (I) of the invention, the following compounds can be synthesized.

(1) 1-[N-(6-Chloro-3-pyridylmethyl)-N-formyl]amino-1-(N-formyl-N-methyl)amino-2-nitroethylene
(2) 1-[N-(6-Chloro-3-pyridylmethyl)-N-ethyl]amino-1-dimethylamino-2-nitroethylene
(3) 1-[N-6-Chloro-3-pyridylmethyl)-N-(2-fluoroethyl)]amino-1-methylamino-2-nitroethylene
(4) 1-[N-(6-Chloro-3-pyridylmethyl)-N-(2-fluoroethyl)]amino-1-dimethylamino-2-nitroethylene
(5) 1-[N-(2-Chloro-5-thiazolylmethyl)-N-formyl]amino-1-(N-formyl-N-methyl)amino-2-nitroethylene
(6) 1-[N-(6-Bromo-3-pyridylmethyl)-N-(2-fluoroethyl)]amino-1-methylamino-2-nitroethylene
(7) 1-[N-(6-Bromo-3-pyridylmethyl)-N-(2-fluoroethyl)]amino-1-dimethylamino-2-nitroethylene
(8) 1-[N-(2-Chloro-5-thiazolylmethyl)-N-(2-fluoroethyl)]amino-1-methylamino-2-nitroethylene
(9) 1-[N-(2-Chloro-5-thiazolylmethyl)-N-methyl]amino-1-dimethylamino-2-nitroethylene
(10) 1-[N-(2-Chloro-5-thiazolylmethyl)-N-ethyl]amino-1-dimethylamino-2-nitroethylene
(11) 1-(2-Bromo-5-thiazolylmethyl)amino-1-methylamino-2-nitroethylene
(12) 1-[N-(2-Bromo-5-thiazolylmethyl)-N-formyl]amino-1-methylamino-2-nitroethylene
(13) 1-[N-(2-Bromo-5-thiazolylmethyl)-N-methyl]amino-1-methylamino-2-nitroethylene
(14) 1-[N-(2-Bromo-5-thiazolylmethyl)-N-ethyl]amino-1-methylamino-2-nitroethylene
(15) 1-(2-Bromo-5-thiazolylmethyl)amino-1-N-formyl-N-methylamino-2-nitroethylene
(16) 1-[N-(2-Bromo-5-thiazolylmethyl)-N-formyl]amino-1-(N-formyl-N-methyl)amino-2-nitroethylene
(17) 1-[N-(2-Bromo-5-thiazolylmethyl)-N-methyl]amino-1-(N-formyl-N-methyl)amino-2-nitroethylene
(18) 1-[N-(2-Bromo-5-thiazolylmethyl)-N-ethyl]amino-1-(N-formyl-N-methyl)amino-2-nitroethylene
(19) 1-[N-(2-Chloro-5-thiazolylmethyl)-N-(2-fluoroethyl)]amino-1-dimethylamino-2-nitroethylene
(20) 1-[N-(2-Bromo-5-thiazolylmethyl)-N-formyl]amino-1-dimethylamino-2-nitroethylene
(21) 1-[N-(2-Bromo-5-thiazolylmethyl)-N-methyl]amino-1-dimethylamino-2-nitroethylene
(22) 1-[N-(2-Bromo-5-thiazolylmethyl)-N-ethyl]amino-1-dimethylamino-2-nitroethylene
(23) 1-[N-Chloromethyl-N-(6-chloro-3-pyridylmethyl)]amino-1-methylamino-2-nitroethylene
(24) 1-[N-(6-Bromo-3-pyridylmethyl)-N-chloromethyl]amino-1-methylamino-2-nitroethylene
(25) 1-[N-Chloromethyl-N-(2-chloro-5-thiazolylmethyl)]amino-1-methylamino-2-nitroethylene
(26) 1-[N-(6-Bromo-3-pyridylmethyl)-N-formyl]amino-1-(N-formyl-N-methyl)amino-2-nitroethylene
(27) 1-[N-(2-Bromo-5-thiazolylmethyl)-N-(2-fluoroethyl)]amino-1-methylamino-2-nitroethylene
(28) 1-[N-(2-Bromo-5-thiazolylmethyl)-N-(2-fluoroethyl)]amino-1-dimethylamino-2-nitroethylene
(29) 1-[N-(2-Chloro-5-thiazolylmethyl)-N-(2,2,2-trifluoroethyl)]amino-1-methylamino-2-nitroethylene
(30) 1-[N-(6-Bromo-3-pyridylmethyl)-N-(2,2,2-trifluoromethyl)]amino-1-dimethylamino-2-nitroethylene
(31) 1-[N-(6-Bromo-3-pyridylmethyl)-N-methyl]amino-1-dimethylamino-2-nitroethylene
(32) 1-[N-(6-Bromo-3-pyridylmethyl)-N-ethyl]amino-1-dimethylamino-2-nitroethylene
(33) 1-(6-Fluoro-3-pyridylmethyl)amino-1-methylamino-2-nitroethylene
(34) 1-[N-(6-Fluoro-3-pyridylmethyl)-N-formyl]amino-1-methylamino-2-nitroethylene
(35) 1-(6-Fluoro-3-pyridylmethyl)amino-1-(N-formyl-N-methyl)amino-2-nitroethylene
(36) 1-[N-(6-Fluoro-3-pyridylmethyl)-N-formyl]amino-1-(N-formyl-N-methyl)amino-2-nitroethylene
(37) 1-[N-(6-Fluoro-3-pyridylmethyl)-N-methyl]amino-1-(N-formyl-N-methyl)amino-2-nitroethylene
(38) 1-[N-(6-Fluoro-3-pyridylmethyl)-N-ethyl]amino-1-(N-formyl-N-methyl)amino-2-nitroethylene
(39) 1-Dimethylamino-1-(6-fluoro-3-pyridylmethyl)amino-2-nitroethylene
(40) 1-Dimethylamino-1-[N-(6-fluoro-3-pyridylmethyl)-N-formyl]amino-2-nitroethylene
(41) 1-Dimethylamino-1-[N-(6-fluoro-3-pyridylmethyl)-N-methyl]amino-2-nitroethylene
(42) 1-Dimethylamino-1-[N-(6-fluoro-3-pyridylmethyl)-N-ethyl]amino-2-nitroethylene Example 112
(Emulsifiable Concentrate)
An emulsifiable concentrate was manufactured by mixing the following ingredients.

| | |
|---|---|
| Compound 17 | 20 weight % |
| Xylene | 75 weight % |
| Polyoxyethylene glycol ether (Nonipol 85 ®) | 5 weight % |

Example 113
(Wettable Powder)
A wettable powder was manufactured by mixing the following ingredients.

| | |
|---|---|
| Compound 12 | 20 weight % |
| Sodium ligninsulfonate | 5 weight % |

-continued

| | |
|---|---|
| Polyoxyethylene glycol ether (Nonipol 85 ®) | 5 weight % |
| White carbon | 30 weight % |
| Clay | 40 weight % |

Example 114

(Dust)

A dust was manufactured by mixing the following ingredients.

| | |
|---|---|
| Compound 19 | 3 weight % |
| White carbon | 3 weight % |
| Clay | 94 weight % |

Example 115

(Granules)

A granular product was prepared by admixing and granulating the following components.

| | |
|---|---|
| Compound 25 | 2 weight % |
| Sodium ligninsulfonate | 5 weight % |
| Clay | 93 weight % |

What we claim is:

1. A method of combatting insects or mites, comprising administering an effective dose of a compound of the formula

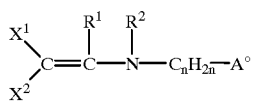

wherein one of $X^1$ and $X^2$ is an electron-attracting group with the other being a hydrogen atom or an electron-attracting group, the electron-attracting groups being cyano, nitro, $C_{1-4}$ alkoxycarbonyl, hydroxycarbonyl, phenoxycarbonyl, naphthyloxycarbonyl, $C_{1-4}$ alkylsulfonyl which can be substituted with halogen, aminosulfonyl, di-$C_{1-4}$ alkoxyphosphoryl, $C_{1-4}$ alkylcarbonyl which can be substituted with halogen, $C_{1-4}$ alkylsulfonylthiocarbamoyl, carbamoyl, or heterocycleoxycarbonyl wherein the heterocycle moiety is defined below as group D; or wherein one of $X^1$ and $X^2$ is a halogen atom; or wherein $X^1$ and $X^2$ can join together with the adjacent carbon atom to form a ring of the formula

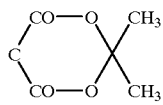

$R^1$ is —$NR^3R^4$ which is attached through its nitrogen atom;

$R^3$ is a hydrogen atom, a $C_{1-6}$ alkyl group, a phenyl group, a naphthyl group, a $C_{7-9}$ phenylalkyl group, a heterocyclic group defined below as the group D, a $C_{1-4}$ alkanoyl, a benzoyl group, a naphthoyl group, a $C_{1-4}$ alkoxy-carbonyl group, a phenoxycarbonyl group, a naphthoxycarbonyl group, a heterocycleoxycarbonyl group wherein the heterocycle moiety is defined below as the group D, a phenylsulfonyl group, a naphthylsulfonyl group, a $C_{1-4}$ alkylsulfonyl group, a di-$C_{1-4}$ alkoxyphosphoryl group, a $C_{1-4}$ alkoxy group, a hydroxy group, an amino group, a di-$C_{1-4}$ alkylamino group, a $C_{1-4}$ alkanoylamino group, a $C_{1-4}$ alkoxycarbonylamino group, a $C_{1-4}$ alkylsulfonylamino group, a di-$C_{1-4}$ alkoxyphosphorylamino group, a $C_{7-9}$ phenylalkyloxy group or a $C_{1-4}$ alkoxy-carbonyl-$C_{1-4}$ alkyl group;

$R^4$ is a hydrogen atom, or a $C_{1-4}$ alkyl, $C_{3-6}$ cycloalkyl, $C_{2-4}$ alkenyl $C_{3-6}$ cycloalkenyl or $C_{2-4}$ alkynyl group which can optionally be substituted by 1 to 3 substituents selected from hydroxyl, $C_{1-4}$ alkoxy, halogen, di-$C_{1-4}$ alkylamino, $C_{1-4}$ alkylthio, $C_{1-3}$ alkylcarbonylamino, $C_{1-4}$ alkylsulfonylamino, tri-$C_{1-4}$ alkylsilyl and pyridyl or thiazolyl which can be optionally substituted with a halogen atom, or $R^3$ and $R^4$ can, taken together with the adjacent nitrogen atom, constitute a pyrrolidino, methylpiperazino, morpholino, or piperidino group, $R^2$ is:

(i) a $C_{1-4}$ alkylcarbonyl, $C_{1-4}$ alkyl, $C_{2-4}$ alkenyl, $C_{3-6}$ cycloalkyl, phenyl, naphthyl, $C_{7-9}$ phenylalkyl or a heterocyclic group defined below as the group D, which can be substituted by 1 to 3 substituents selected from the group consisting of a $C_{1-4}$ alkylthio group, a $C_{1-4}$ alkoxy group, a mono-$C_{1-4}$ alkylamino group, a di-$C_{1-4}$ alkylamino group, a $C_{1-4}$ alkoxycarbonyl group, a $C_{1-4}$ -alkylsulfonyl group, a halogen atom and a $C_{1-4}$ alkanoyl group, or (ii) a $C_{1-4}$ alkoxy, $C_{3-6}$ cycloalkoxy, $C_{2-4}$ alkenyloxy, $C_{3-6}$ cycloalkenyloxy, ethynyloxy, phenoxy, naphthoxy, a heterocycleoxy group, wherein the heterocycle moiety is defined below as the group D, or hydroxyl group which can have 1 to 3 substituents selected from the group consisting of halogen and phenyl, or (iii) the group —$NR^3R^4$ which is attached through its nitrogen atom, or (iv) hydrogen;

n is an integer equal to 0, 1 or 2, and $A^0$ is a substituted or unsubstituted heterocyclic group defined below as group D, provided that $A^0$ is not a moiety selected from the group consisting of 2-, 3-, or 4-pyridyl and 2-, 4- or 5-thiazolyl;

wherein the group D is a moiety selected from the group consisting of 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxido-2-, 3- or 4-pyridyl, 2-, 4- or 5-pyrimidinyl, N-oxido-2-, 4- or 5-pyrimidinyl, 3- or 4-pyridazinyl, pyrazinyl, N-oxido-3- or 4-pyridazinyl, benzofuryl, benzothiazolyl, benzoxazolyl, triazinyl, oxotriazinyl, tetrazolo[1,5-b]pyridazinyl, triazolo[4,5-b]pyridazinyl, oxoimidazinyl, dioxotriazinyl, pyrrolidinyl, piperidinyl pyranyl, thiopyranyl, 1,4-oxazinyl, morpholinyl, 1,4-thiazinyl, 1,3-thiazinyl, piperazinyl, benzimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl and phenoxazinyl group, any of which can have 1 to 5 substituents selected from the group consisting of
(i) a $C_{1-4}$ alkyl,
(ii) $C_{3-6}$ cycloalkyl,
(iii) phenyl, naphthyl,
(iv) $C_{1-4}$ alkoxy,
(v) $C_{3-6}$ cycloalkyloxy,
(vi) phenoxy, naphthyloxy,
(vii) $C_{7-12}$ phenylalkyloxy,
(viii) $C_{1-4}$ alkylthio,
(ix) $C_{3-6}$ cycloalkylthio,
(x) phenylthio, naphthylthio,
(xi) $C_{7-12}$ phenylalkylthio,
(xii) mono-$C_{1-4}$ alkylamino,
(xiii) di-$C_{1-4}$ alkylamino,
(xiv) $C_{3-6}$ cycloalkylamino,
(xv) anilino,
(xvi) $C_{7-12}$ phenylalkylamino,
(xvii) halogen
(xviii) $C_{1-4}$ alkoxycarbonyl,
(xix) phenoxycarbonyl,
(xx) $C_{3-6}$ cycloalkyloxycarbonyl,
(xxi) $C_{7-12}$ phenylalkyloxycarbonyl,
(xxii) $C_{1-5}$ alkanoyl,
(xxiii) $C_{1-15}$ alkanoyloxy,
(xxiv) carbamoyl, N-methylcarbamoyl, N,N-dimethylcarbamoyl, N-ethylcarbamoyl, N,N-diethylcarbamoyl, N-phenylcarbamoyl, pyrrolidinocarbamoyl, piperidinocarbamoyl, piperazinocarbamoyl, morpholinocarbamoyl, N-benzylcarbamoyl,
(xxv) N-methylcarbamoyloxy, N,N-dimethylcarbamoyloxy, N-ethylcarbamoyloxy, N-benzylcarbamoyloxy, N,N-dibenzylcarbamoyloxy, N-phenylcarbamoyloxy,
(xxvi) $C_{1-4}$ alkanoylamino,
(xxvii) benzamido,
(xxviii) $C_{1-4}$ alkoxycarbonylamino,
(xxix) $C_{7-12}$ phenylalkyloxycarbonyl,
(xxx) methanesulfonylamino, ethanesulfonylamino, butanesulfonylamino, benzenesulfonylamino, toluenesulfonylamino, naphthalenesulfonylamino, trifluoromethanesulfonylamino, 2-chloroethanesulfonylamino, 2,2,2-trifluoromethanesulfonylamino,
(xxxi) pyrrolidinyl, pyrrolyl, pyrazolyl, imidazolyl, furyl, thienyl, oxazolyl isoxazolyl, isothiazolyl, thiazolyl, piperidinyl, pyridyl, piperazinyl, pyrimidinyl, pyranyl, tetrahydropyranyl, tetrahydrofuryl, indolyl, quinolyl, 1,3,4-oxadiazolyl, thieno[2,3-d]pyridyl, 1,2,3-thiadiazolyl, 1,3,4-thiadiazolyl, 1,2,3-triazolyl, 1,2,4-triazolyl, 1,3,4-triazolyl, tetrazolyl, 4,5-dihydro-1,3-dioxazolyl, tetrazolo[1,5-b]pyridazinyl, benzothiazolyl, benzoxazolyl, benzimidazolyl, benzothienyl,
(xxxii) heterocyclethio, heterocycleoxy, heterocycleamino or heterocyclecarbonylamino group which is derived by attachment of any of heterocyclic groups (xxxi) to the S, O, N atom or the carbonylamino group,
(xxxiii) di-$C_{1-4}$ alkylphosphinothioylamino,
(xxxiv) methoxyimino, ethoxyimino, 2-fluoroethoxyimino, carboxymethoxyimino, 1-carboxy-1-methylethoxyimino, 2,2,2-trichloroethoxycarbonylmethoxyimino, 1-(2,2,2-trichloroethoxycarbonyl)-1-methylethoxyimino, (2-aminothiazol-4-yl) methoxyimino, (1H-imidazol-4-yl)methoxyimino,
(xxxv) $C_{1-4}$ alkylsulfonyloxy,
(xxxvi) benzenesulfonyloxy, toluenesulfonyloxy,
(xxxvii) diphenylphosphinothioylamino,
(xxxviii) thiocarbamoylthio, N-methylthiocarbamoylthio, N,N-dimethylthiocarbamoylthio, N-ethylthiocarbamoylthio, N-benzylthiocarbamoylthio, N,N-dibenzylthiocarbamoylthio, N-phenylthiocarbamoylthio,
(xxxix) trimethylsilyloxy, t-butyldimethylsilyloxy, t-butyldiphenylsilyloxy, dimethylphenylsilyloxy,
(xL) trimethylsilyl, t-butyldinethylsilyl, t-butyldiphenylsilyl, dimethylphenylsilyl,
(xLi) $C_{1-4}$ alkylsulfinyl,
(xLii) phenylsulfinyl, naphthylsulfinyl,
(xLiii) $C_{1-4}$ alkylsulfonyl,
(xLiv) benzenesulfonyl, toluenesulfonyl,
(xLv) $C_{1-4}$ alkoxy-carbonyloxy,
(xLvi) halo-$C_{1-4}$ alkyl,
(xLvii) halo-$C_{1-4}$ alkoxy, halo-$C_{1-4}$ alkylthio, halo-$C_{1-4}$ alkylsulfinyl halo-$C_{1-4}$ alkylsulfonyl,
(xLviii) cyano, nitro, hydroxyl, carboxyl, sulfo, phosphono,
(xLix) $C_{1-4}$ alkyloxysulfonyl,
(L) phenoxysulfonyl, tolyloxysulfonyl,
(Li) $C_{7-12}$ phenylalkyloxysulfonyl and
(Lii) di-$C_{1-4}$ alkyloxyphosphoryl group, or a salt thereof.

2. A method according to claim 1, wherein $X^1$ is nitro;

$X^2$ is a hydrogen atom, $C_{1-2}$ alkoxycarbonyl or $C_{1-2}$ alkylsulfonylthiocarbamoyl;

$R^1$ is amino, mono- or di-$C_{1-4}$ alkylamino, halo-$C_{1-4}$ alkylamino, N-$C_{1-4}$ alkyl-N-$C_{1-2}$ alkanoylamino, N-halo-$C_{1-4}$ alkyl-N-$C_{1-2}$ alkanoylamino or $C_{1-2}$ alkanoylamino;

$R^2$ is a hydrogen atom, $C_{1-2}$ alkoxy, di-$C_{1-2}$ alkylamino, $C_{1-4}$ alkyl, halo-$C_{1-4}$ alkyl or $C_{1-2}$ alkanoyl;

n is an integer equal to 0 or 1; and $A^O$ is selected from the group consisting of 2- or 3-thienyl, 2- or 3-furyl, 2- or 3-pyrrolyl, 2-, 4- or 5-oxazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxido-2-, 3- or 4-pyridyl, 2-, 4- or 5-pyrimidinyl, N-oxido-2-, 4- or 5-pyrimidinyl, 3- or 4-pyridazinyl, pyrazinyl, N-oxido-3- or 4-pyridazinyl, benzofuryl, benzothiazolyl, benzoxazolyl, triazinyl, oxotriazinyl, tetrazolo[1,5-b]pyridazinyl, triazolo[4,5b]pyridazinyl, oxoimidazolyl, dioxotriazinyl, pyrrolidinyl, piperidinyl, pyranyl, thiopyranyl, 1,4-oxazinyl, morpholinyl, 1,4-thiazinyl, 1,3-thiazinyl, piperazinyl, benzimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl, and phenoxazinyl, any of which can be unsubstituted or substituted with halogen, $C_{1-4}$ alkyl, halo-$C_{1-4}$ alkyl, $C_{1-4}$ alkoxy, halo-$C_{1-4}$ alkoxy, $C_{1-4}$ alkylthio or halo-$C_{1-4}$ alkylthio.

3. A method according to claim 1, wherein $X^1$ is nitro;

$X^2$ is a hydrogen atom or $C_{1-2}$ alkylsulfonylthiocarbamoyl;

$R^1$ is amino, mono- or di-$C_{1-2}$ alkylamino, halo-$C_{1-2}$ alkylamino, N-$C_{1-2}$ alkyl-N-$C_{1-2}$ alkanoylamino, N-halo-$C_{1-2}$ alkyl-N-$C_{1-2}$ alkanoylamino or $C_{1-2}$ alkanoylamino;

$R^2$ is a hydrogen atom, $C_{1-2}$ alkoxy, di-$C_{1-2}$ alkylamino, $C_{1-4}$ alkyl, halo-$C_{1-4}$ alkyl or $C_{1-2}$ alkanoyl;

n is 1; and $A^O$ is pyrazinyl, which is unsubstituted or substituted with halogen, $C_{1-4}$ alkyl, halo-$C_{1-4}$ alkyl, $C_{1-4}$alkoxy, halo-$C_{1-4}$ alkoxy, $C_{1-4}$ alkylthio or halo-$C_{1-4}$ alkylthio.

4. The method according to claim 1, wherein $X^1$ is nitro;

$X^2$ is a hydrogen atom, $C_{1-4}$ alkoxycarbonyl or $C_{1-4}$ alkylsulfonylthiocarbamoyl;

$R^2$ is a hydrogen atom, $C_{1-3}$ alkanoyl, $C_{1-4}$ alkyl, mono- or di-$C_{1-4}$ alkoxy-$C_{1-4}$ alkyl, $C_{7-9}$ phenylalkyl, mono- or di-$C_{1-4}$ alkylamino or $C_{1-4}$ alkoxy; and $A^O$ is pyrazinyl which is unsubstituted or substituted with halogen, $C_{1-4}$ alkyl or $C_{1-4}$ alkoxy.

5. The method according to claim 1, wherein $X^1$ is nitro;

$X^2$ is a hydrogen atom, $C_{1-4}$ alkoxycarbonyl or $C_{1-4}$ alkylsulfonylthiocarbamoyl;

$R^1$ is amino, mono- or di-$C_{1-4}$ alkylamino, N-$C_{1-4}$ alkyl-N-$C_{1-3}$ alkanoylamino, $C_{7-9}$ phenylalkylamino, halogenothiazolyl-$C_{1-2}$ alkylamino or $C_{1-4}$ alkoxy-$C_{1-2}$ alkylamino;

$R^2$ is a hydrogen atom, $C_{1-3}$ alkanoyl, $C_{1-4}$ alkyl, mono- or di-$C_{1-4}$ alkoxy-$C_{1-4}$ alkyl, $C_{7-9}$ phenylalkyl, mono- or di-$C_{1-4}$ alkylamino or $C_{1-4}$ alkoxy; and, $A^O$ is pyrazinyl which is unsubstituted or substituted with halogen, $C_{1-4}$ alkyl or $C_{1-4}$ alkoxy.

\* \* \* \* \*